US012758631B2

(12) United States Patent
Avigan et al.

(10) Patent No.: US 12,758,631 B2
(45) Date of Patent: Oct. 13, 2026

(54) PERSONALIZED FUSION CELL VACCINES

(71) Applicants: Dana-Farber Cancer Institute, Inc., Boston, MA (US); Beth Israel Deaconess Medical Center, Boston, MA (US)

(72) Inventors: David Avigan, Sharon, MA (US); Jacalyn Rosenblatt, Newton, MA (US); Donald Kufe, Wellesley, MA (US)

(73) Assignees: Dana-Farber Cancer Institute, Inc., Boston, MA (US); Beth Israel Deaconess Medical Center, Boston, MA (US)

( * ) Notice: Subject to any disclaimer, the term of this patent is extended or adjusted under 35 U.S.C. 154(b) by 380 days.

(21) Appl. No.: 18/031,260

(22) PCT Filed: Nov. 12, 2021

(86) PCT No.: PCT/US2021/059199

§ 371 (c)(1),
(2) Date: Apr. 11, 2023

(87) PCT Pub. No.: WO2022/104104

PCT Pub. Date: May 19, 2022

(65) Prior Publication Data

US 2024/0024474 A1 Jan. 25, 2024

Related U.S. Application Data

(60) Provisional application No. 63/113,616, filed on Nov. 13, 2020.

(51) Int. Cl.

| | |
|---|---|
| ***A61K 40/11*** | (2025.01) |
| ***A61K 38/17*** | (2006.01) |
| ***A61K 38/19*** | (2006.01) |
| ***A61K 39/395*** | (2006.01) |
| ***A61K 40/19*** | (2025.01) |
| ***A61K 40/24*** | (2025.01) |
| ***A61K 40/31*** | (2025.01) |
| ***A61K 40/42*** | (2025.01) |
| ***A61K 47/36*** | (2006.01) |
| ***A61P 35/00*** | (2006.01) |
| ***A61P 35/02*** | (2006.01) |
| ***C12N 5/0783*** | (2010.01) |
| ***C12N 5/16*** | (2006.01) |

(52) U.S. Cl.

CPC .......... *A61K 40/11* (2025.01); *A61K 38/1709* (2013.01); *A61K 38/191* (2013.01); *A61K 39/3955* (2013.01); *A61K 40/19* (2025.01); *A61K 40/24* (2025.01); *A61K 40/31* (2025.01); *A61K 40/4211* (2025.01); *A61K 40/4215* (2025.01); *A61K 47/36* (2013.01); *A61P 35/00* (2018.01); *A61P 35/02* (2018.01); *C12N 5/0636* (2013.01); *C12N 5/0638* (2013.01); *C12N 5/16* (2013.01); *A61K 2239/31* (2023.05); *A61K 2239/38* (2023.05); *A61K 2239/48* (2023.05); *C12N 2501/998* (2013.01); *C12N 2502/99* (2013.01); *C12N 2533/74* (2013.01)

(58) Field of Classification Search

CPC .. A61K 40/11; A61K 38/1709; A61K 38/191; A61K 39/3955; A61K 40/19; A61K 40/24; A61K 40/31; A61K 40/4211; A61K 40/4215; A61K 47/36; A61P 35/00; A61P 35/02; C12N 5/0636; C12N 5/0638; C12N 5/16

See application file for complete search history.

(56) References Cited

U.S. PATENT DOCUMENTS

| | | | | |
|---|---|---|---|---|
| 4,045,176 A * | 8/1977 | Proksch | G01N 33/96 | 436/15 |
| 5,374,974 A * | 12/1994 | Rostoker | G03F 7/702 | 355/71 |
| 5,998,578 A * | 12/1999 | Auron | A61P 43/00 | 530/344 |
| 6,201,109 B1 * | 3/2001 | Avnur | C07K 16/40 | 530/388.26 |
| 2003/0175247 A1 * | 9/2003 | Salgaller | A61K 40/4276 | 424/185.1 |
| 2004/0115224 A1 * | 6/2004 | Ohno | A61K 40/11 | 424/277.1 |
| 2005/0013811 A1 * | 1/2005 | Chen | A61K 40/428 | 424/234.1 |
| 2005/0169898 A1 * | 8/2005 | Gong | A61K 40/4257 | 435/372 |

(Continued)

FOREIGN PATENT DOCUMENTS

| | | | |
|---|---|---|---|
| CN | 108148812 A | 6/2018 | |
| WO | WO-2020061203 A1 * | 3/2020 | A61K 31/716 |

(Continued)

OTHER PUBLICATIONS

Gheybi MK et al. "The correlation of CD19 + CD24 + CD38 + B cells and other clinicopathological variables with the proportion of circulating Tregs in breast cancer patients." Breast Cancer 24: 756-764. (Year: 2017).*
Avigan et al., "Vaccine therapy in hematologic malignancies", Blood, vol. 131(24): 2640-2650, Jun. 14, 2018.
Capelletti et al., "Potent Synergy between Combination of Chimeric Antigen Receptor (CAR) Therapy Targeting CD19 in Conjunction with Dendritic Cell (DC)/Tumor Fusion Vaccine in Hematological Malignancies", Biology of Blood and Marrow Transplantation, vol. 26, Issue 3, Supplemental, Mar. 2020, pp. S42-S43.
Capelletti et al., "Potent Synergy between Combination of Chimeric Antigen Receptor (CAR) Therapy Targeting CD19 in Conjunction with Dendritic Cell (DC)/Tumor Fusion Vaccine in Hematological Malignancies," Blood, 134(Supp. 1): 3227 (2019).

(Continued)

*Primary Examiner* — Lora E Barnhart Driscoll
(74) *Attorney, Agent, or Firm* — Foley Hoag LLP; DeAnn F. Smith; Philip S. Choi

(57) ABSTRACT

The present invention provides compositions and methods for treating cancer.

11 Claims, 38 Drawing Sheets

(56) References Cited

U.S. PATENT DOCUMENTS

| | | | | |
|---|---|---|---|---|
| 2009/0087450 | A1* | 4/2009 | Wagner | A61K 35/74 424/193.1 |
| 2012/0322862 | A1* | 12/2012 | Vaught | A61K 31/7115 536/23.1 |
| 2014/0227272 | A1* | 8/2014 | Kufer | A61K 31/10 514/706 |
| 2014/0271635 | A1* | 9/2014 | Brogdon | A61K 40/4211 536/23.53 |
| 2014/0294930 | A1* | 10/2014 | Nizet | A61K 39/092 424/193.1 |
| 2017/0044496 | A1* | 2/2017 | Sarnaik | A61K 40/4272 |
| 2018/0071340 | A1* | 3/2018 | Avigan | A61P 35/00 |
| 2018/0078650 | A1* | 3/2018 | Avigan | A61K 39/00 |
| 2019/0151361 | A1* | 5/2019 | Wiezorek | A61K 40/11 |
| 2019/0310251 | A1* | 10/2019 | Tovey | C12N 15/63 |
| 2019/0367880 | A1* | 12/2019 | Draganov | A61K 35/28 |
| 2020/0261540 | A1* | 8/2020 | He | A61K 38/2013 |

FOREIGN PATENT DOCUMENTS

| | | | |
|---|---|---|---|
| WO | WO-2022/104104 | A2 | 5/2022 |
| WO | WO-2022/104104 | A3 | 6/2022 |

OTHER PUBLICATIONS

International Search Report and Written Opinion for International Application No. PCT/US2021/059199 dated May 16, 2022.

Invitation to Pay Additional Fees for International Application No. PCT/US2021/059119 dated Mar. 14, 2022.

Liegel et al., "T Cells Educated By DC/AML Fusions in the Context of 4-1BB Costimulation As a Potent Strategy for Adoptive Cellular Therapy", Blood (2019), 134 (Supplement_1): 2673.

Munger et al., "Optimized adoptive T-cell therapy for the treatment of residual mantle cell lymphoma," Cancer Immunology, Immunotherapy, 61: 1819-1832 (2012).

Orr et al., "Development of Novel Second Generation DC/Tumor Fusion Vaccine in Lymphoma", Biology of Blood and Marrow Transplantation, vol. 26, Issue 3, Supplemental, S316, Mar. 1, 2020.

Orr et al., "Development of Novel Second Generation DC/Tumor Fusion Vaccine in Lymphoma", Blood (2019) 134 (Supplement_1): 392.

Shi et al., "A new PD-1-specific nanobody enhances the antitumor activity of T-cells in synergy with dendritic cell vaccine," Cancer Letters, 522: 184-197 (2021).

* cited by examiner

Clinical Trial of Vaccination and Nivolumab in Patients with Relapsed Multiple Myeloma

PERSONALIZED FUSION CELL VACCINES

CROSS-REFERENCE TO RELATED APPLICATIONS

This application is the U.S. national phase of International Patent Application No. PCT/US2021/059199, filed on 12 Nov. 2021, which claims the benefit of priority to U.S. Provisional Application Ser. No. 63/113,616, filed on 13 Nov. 2020; the entire contents of each of said applications is are incorporated herein in their entirety by this reference.

STATEMENT OF RIGHTS

This invention was made with government support under grant number P50 CA206963 awarded by The National Institutes of Health. The government has certain rights in the invention.

BACKGROUND OF THE INVENTION

CAR-T cell therapies have been particularly effective in targeting CD19-positive B cell malignancies. CAR-T cells are also showing activity against other hematologic malignancies, such as in the treatment of BCMA-expressing multiple myeloma (MM). One of the challenges for CAR-T cell therapy is loss of activity associated with exhaustion.

Various CAR generations have certain advantages. For example, they provide HLA independent antigen recognition, rapid generations of tumor specific CD4+ and CD8+ T cells, minimal risk of autoimmunity or GvHD, and a living drug that can be applied via a single infusion. However, various CAR generations also have certain disadvantages. For example, they have "on" target side effects such as cytokine release syndrome (CRS) (~Steroids, IL6 inhibitors), "off" target-side effects such as B cell aplasia (~immunoglobulin therapy), limited persistence, and escape mechanism of resistance through antigen loss.

On the other hand, fusion cell (FC) vaccines (e.g., for the treatment of patients with MM and AML) activate T-cells by presentation of tumor associated antigens in the context of the machinery of the dendritic cell (DC). These vaccines have certain advantages. For example, they provide rapid generations of tumor specific CD4+ AND CD8+ T cells, minimal risk of autoimmunity or GvHD, a living drug with multiple doses possible, broad antigenic repertoire, and prolonged persistence. However, they also have certain limitations, such as being active mainly in low tumor burden (e.g., after ASCT).

Therefore, there is a need in the field for improved cancer treatments, for example those that overcome the limitations of CAR-T approaches and fusion cell approaches.

SUMMARY OF THE INVENTION

The present invention is based, at least in part, on the discovery that a fusion cell vaccine can be used to improve cancer therapy, for example by further educating T cells by using a T-cell stimulator (e.g., agonistic 4-1BB antibody, biomatrix), and by combining fusion cell approaches with additional anti-cancer therapies (e.g., immune checkpoint therapy, CAR-T).

In an aspect, methods of producing a cancer therapeutic include fusing a dendritic cell with a tumor cell to obtain a fusion cell; contacting the fusion cell with a T cell to obtain an educated T cell; and obtaining the cancer therapeutic by combining the educated T cell with another anti-cancer therapy; and/or stimulating the T cell or the educated T cell with a T-cell stimulator during, before, or after said contacting step.

In an aspect, cancer therapeutics are disclosed, which are produced according to the disclosed methods of producing a cancer therapeutic.

In an aspect, methods of treating a cancer in a subject include administering to the subject a disclosed cancer therapeutic. In some embodiments, the method comprises said another anti-cancer therapy, and wherein said another anti-cancer therapy is administered before, after, or at the same time as the educated T cells. In some embodiments, the method comprises said another anti-cancer therapy, and wherein said another anti-cancer therapy is conjointly with the educated T cells.

Numerous embodiments are further provided that can be applied to any aspect encompassed by the present invention and/or combined with any other embodiment described herein. For example, with respect to methods of producing a cancer therapeutic, in some embodiments, the method comprises said another anti-cancer therapy, and wherein said another anti-cancer therapy is administered before, after, or at the same time as the educated T cells. In some embodiments, the method comprises said another anti-cancer therapy, and wherein said another anti-cancer therapy is conjointly with the educated T cells.

In some embodiments, the dendritic cell and the tumor cell are autologous. In some embodiments, the fusion cell and the T cell are syngeneic. In some embodiments, obtaining the cancer therapeutic comprises combining the educated T cell with said another anti-cancer therapy, and wherein said another anti-cancer therapy comprises immune checkpoint therapy. In some embodiments, the immune checkpoint therapy comprises an inhibitor of at least one selected from the group consisting of PD-1, PD-L1, PD-L2, TIM-3, LAG-3, CTLA-4, and combinations thereof. In some embodiments, the inhibitor comprises at least one antibody selected from the group consisting of anti-PD-1 antibodies, anti-CTLA4 antibodies, anti-PD-L1 antibodies, anti-PD-L2 antibodies, and combinations thereof. In some embodiments, the immune checkpoint therapy comprises an anti-PD-1 antibody.

In some embodiments, obtaining the cancer therapeutic comprises combining the educated T cell with said another anti-cancer therapy, and wherein said another anti-cancer therapy comprises natural killer cells. In some embodiments, obtaining the cancer therapeutic comprises combining the educated T cell with said another anti-cancer therapy, and wherein said another anti-cancer therapy comprises CAR-T cells. In some embodiments, said CAR-T cells comprise a chimeric antigen receptor directed against a target selected from CD-19 and BCMA. In some embodiments, obtaining the cancer therapeutic comprises stimulating the T cell or the educated T cell with a T-cell stimulator during said contacting step, and wherein said T-cell stimulator comprises a biomatrix that comprises alginate, RGD peptide, and 4-1BBL. In some embodiments, obtaining the cancer therapeutic comprises stimulating the T cell or the educated T cell with a T-cell stimulator before or after said contacting step, and wherein said T-cell stimulator comprises an agonistic 4-1BB antibody or an antigen-binding fragment thereof.

In some embodiments, the tumor cells are from a leukemia. In some embodiments, the leukemia comprises acute myelogenous leukemia. In some embodiments, the tumor cells are from a lymphoma. In some embodiments, the lymphoma comprises multiple myeloma. In some embodiments, the methods further comprise subjecting the fusion cell to gamma irradiation. In some embodiments, the method comprises a population of cells for each of said dendritic cell, tumor cell, fusion cell, T cell, and educated T cell.

In some aspects, methods of treating a cancer in a subject include administering to the subject a combination of a fusion component and a T-cell component, wherein the fusion component comprises either a fusion of a dendritic cell and a tumor cell, or a personalized molecular fusion cell; and the T-cell component is administered either before, during, or after the fusion component.

In some embodiments, the T-cell component comprises T cells. In some embodiments, the T-cell component further comprises an agonistic 4-1BB antibody or an antigen-binding fragment thereof. In some embodiments, the methods further comprise deploying a biomatrix in conjunction with the fusion component. In some embodiments, the biomatrix comprises alginate, RGD peptide, and 4-1BBL. In some embodiments, the T-cell component comprises CAR-T. In some embodiments, the CAR-T is directed against CD-19. In some embodiments, the CAR-T is directed against BCMA. In some embodiments, the cancer comprises a leukemia. In some embodiments, the leukemia comprises acute myelogenous leukemia. In some embodiments, the cancer is a lymphoma. In some embodiments, the lymphoma comprises multiple myeloma. In some embodiments, the cancer is pancreatic cancer.

BRIEF DESCRIPTION OF FIGURES

FIG. 35A shows percentage of GFP+ CAR T cells in culture immediately after T cell transduction with the m19BBz-GFP CAR (Li et al. (2017) *Blood* 130:843; Manuduri et al. (2020) *Exp. Rev. Hematol.* 13: DOI:10.1080/17474086.2020.1753501; Ghosh et al. (2017) *Nat. Med.* 23:242-249) (CAR T time 0) or after 3 days of co-culture in the presence (fusions-educated CAR T cells) or the absence (CAR T cells) of the DC/A20 vaccine. Non-transduced T cells were used as negative control. FIG. 35B shows percentage of CD4+ and CD8+ GFP+ CAR T cells in culture after 3 days of co-culture in the presence (fusions-educated CAR T cells) or the absence (CAR T cells) of the DC/A20 vaccine. FIG. 35C shows percentage of GFP+ CAR T cells in culture after 3 days of co-culture in the presence (fusions-educated CAR T cells) or the absence (CAR T cells) of the DC/A20 vaccine. Data are normalized to time 0. Data are mean±SD of 4 independent experiments. **=p<0.01.

FIG. 35A shows percentage of GFP+ CAR T cells in the bone marrow (BM). FIG. 35B shows percentage of GFP+ CAR T cells in the spleen. FIG. 35C shows percentage of spleen CD8+ T-cells specific for the A20 idiotype epitope. Vaccine-boosted animals show increased CAR T cells in the bone marrow (BM) and spleen. Increased CAR T cells with TCR restriction for the A20 IgG tetramer consistent with vaccine-educated TCR expansion of the CAR T population. Data are mean±SEM. *=$p<0.05$.

Figure 1:
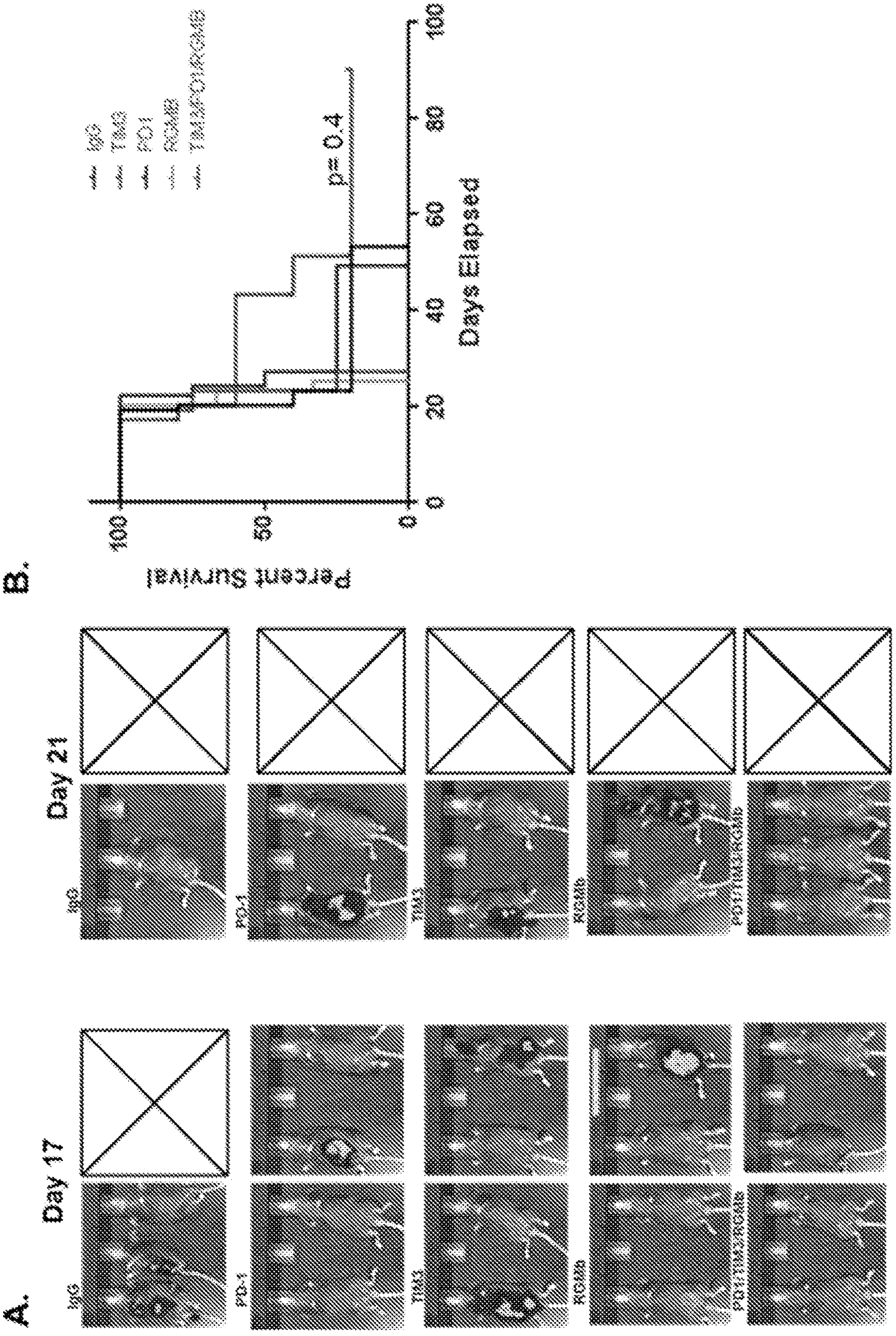
FIG. 1A and FIG. 1B show that checkpoint blockade does not significantly affect AML engraftment in-vivo. C57BL/6J mice were retro-orbitally inoculated with $50\times10^3$ syngeneic TIB-49 AML cells that were stably transduced with luciferase/m-cherry. The mice were then treated with six doses of 200 μg anti-PD1, anti-TIM3, anti-RGMb or combination of the three mAbs using IP injections every three days. The mice were treated with appropriate isotype control as a negative control. For AML progression, (A) BLI imaging was performed on days 17 and 21 post inoculation with tumor (n=5). (B) The mice were followed for survival for 90 days as demonstrated in a Kaplan Meier curve (n=5).

For any figure showing a bar histogram, curve, or other data associated with a legend, the bars, curve, or other data presented from left to right for each indication correspond directly and in order to the boxes from top to bottom, or from left to right, of the legend.

DETAILED DESCRIPTION OF THE INVENTION

The fusion cell (FC) approach is unique in that the FC vaccine induces CD8+ CTLs, as well as memory CD4+ T-cells, and as such can activate CAR-T cells and prolong that activation by maintaining memory. The use of FC vaccines to enhance CAR-T cell activity can be realized using the (i) personalized tumor cell/DC fusions and/or (ii) personalized molecular FC vaccine. In some embodiments, a "molecular FC vaccine" is one in which the transcriptome, or portion thereof, of the cancer cell, is expressed in DCs. The FC vaccines would be administered before, during and/or after infusion of the CAR-T cells. The personalized molecular FC vaccine would be modified to specifically stimulate responses to antigens targeted by the CAR-T, such as CD19, BCMA and others. In this way, the FC vaccine would be used to increase the extent and duration of CAR-T cell activity in settings of established effectiveness, as well as those in which CAR-T cells have not demonstrated efficacy, such as against solid tumors. The FC vaccine would also represent an approach to increase selectivity of CAR-T cells against tumor and not normal cells. Notably, the FC vaccine could also be used to improve effectiveness of TCRs and NK cell CARs.

I. Definitions

The articles "a" and "an" are used herein to refer to one or to more than one (i.e. to at least one) of the grammatical object of the article. By way of example, "an element" means one element or more than one element.

Unless otherwise specified here within, the terms "antibody" and "antibodies" broadly encompass naturally-occurring forms of antibodies (e.g. IgG, IgA, IgM, IgE) and recombinant antibodies such as single-chain antibodies, chimeric and humanized antibodies and multi-specific antibodies, as well as fragments and derivatives of all of the foregoing, which fragments and derivatives have at least an antigenic binding site. Antibody derivatives may comprise a protein or chemical moiety conjugated to an antibody.

The term "antibody" as used herein also includes an "antigen-binding portion" of an antibody (or simply "antibody portion"). The term "antigen-binding portion", as used herein, refers to one or more fragments of an antibody that retain the ability to specifically bind to an antigen (e.g., a polypeptide or fragment thereof). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the VL, VH, CL and CH1 domains; (ii) a $F(ab')_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al. (1989) Nature 341:544-546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent polypeptides (known as single chain Fv (scFv); see e.g., Bird et al. (1988) *Science* 242:423-426; and Huston et al. (1988) *Proc. Natl. Acad. Sci. USA* 85:5879-5883; and Osbourn et al. 1998, Nature Biotechnology 16: 778). Such single chain antibodies are also intended to be encompassed within the term "antigen-binding portion" of an antibody. Any V H and VL sequences of specific scFv can be linked to human immunoglobulin constant region cDNA or genomic sequences, in order to generate expression vectors encoding complete IgG polypeptides or other isotypes. VH and VL can also be used in the generation of Fab, Fv or other fragments of immunoglobulins using either protein chemistry or recombinant DNA technology. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al. (1993) *Proc. Natl. Acad. Sci. USA* 90:6444-6448; Poljak, R. J., et al. (1994) *Structure* 2:1121-1123).

Still further, an antibody or antigen-binding portion thereof may be part of larger immunoadhesion polypeptides, formed by covalent or noncovalent association of the antibody or antibody portion with one or more other proteins or peptides. Examples of such immunoadhesion polypeptides include use of the streptavidin core region to make a tetrameric scFv polypeptide (Kipriyanov, S. M., et al. (1995) *Human Antibodies and Hybridomas* 6:93-101) and use of a cysteine residue, peptide and a C-terminal polyhistidine tag to make bivalent and biotinylated scFv polypeptides (Kipriyanov, S. M., et al. (1994) *Mol. Immunol.* 31:1047-1058). Antibody portions, such as Fab and $F(ab')_2$ fragments, can be prepared from whole antibodies using conventional techniques, such as papain or pepsin digestion, respectively, of whole antibodies. Moreover, antibodies, antibody portions and immunoadhesion polypeptides can be obtained using standard recombinant DNA techniques, as described herein.

Antibodies may be polyclonal or monoclonal; xenogeneic, allogeneic, or syngeneic; or modified forms thereof (e.g. humanized, chimeric, etc.). Antibodies may also be fully human. Preferably, antibodies encompassed by the present invention bind specifically or substantially specifically to a polypeptide or fragment thereof. The terms "monoclonal antibodies" and "monoclonal antibody composition", as used herein, refer to a population of antibody polypeptides that contain only one species of an antigen binding site capable of immunoreacting with a particular epitope of an antigen, whereas the term "polyclonal antibodies" and "polyclonal antibody composition" refer to a population of antibody polypeptides that contain multiple species of antigen binding sites capable of interacting with a particular antigen. A monoclonal antibody composition typically displays a single binding affinity for a particular antigen with which it immunoreacts.

Antibodies may also be "humanized", which is intended to include antibodies made by a non-human cell having variable and constant regions which have been altered to more closely resemble antibodies that would be made by a human cell. For example, by altering the non-human antibody amino acid sequence to incorporate amino acids found in human germline immunoglobulin sequences. The humanized antibodies encompassed by the present invention may include amino acid residues not encoded by human germline immunoglobulin sequences (e.g., mutations introduced by random or site-specific mutagenesis in vitro or by somatic mutation in vivo), for example in the CDRs. The term "humanized antibody", as used herein, also includes antibodies in which CDR sequences derived from the germline of another mammalian species, such as a mouse, have been grafted onto human framework sequences.

A "blocking" antibody or an antibody "antagonist" is one which inhibits or reduces at least one biological activity of the antigen(s) it binds. In certain embodiments, the blocking antibodies or antagonist antibodies or fragments thereof described herein substantially or completely inhibit a given biological activity of the antigen(s). The term "body fluid" refers to fluids that are excreted or secreted from the body as well as fluids that are normally not (e.g. amniotic fluid, aqueous humor, bile, blood and blood plasma, cerebrospinal fluid, cerumen and earwax, cowper's fluid or pre-ejaculatory fluid, chyle, chyme, stool, female ejaculate, interstitial fluid, intracellular fluid, lymph, menses, breast milk, mucus, pleural fluid, pus, saliva, sebum, semen, serum, sweat, synovial fluid, tears, urine, vaginal lubrication, vitreous humor, vomit).

The terms "cancer" or "tumor" or "hyperproliferative" refer to the presence of cells possessing characteristics typical of cancer-causing cells, such as uncontrolled proliferation, immortality, metastatic potential, rapid growth and proliferation rate, and certain characteristic morphological features. In some embodiments, such cells exhibit such characteristics in part or in full due to the expression and activity of immune checkpoint proteins, such as PD-1, PD-L1, PD-L2, TIM, LAG, and/or CTLA-4. Cancer cells are often in the form of a tumor, but such cells may exist alone within an animal, or may be a non-tumorigenic cancer cell, such as a leukemia cell. As used herein, the term "cancer" includes premalignant as well as malignant cancers. Cancers include, but are not limited to, B cell cancer, e.g., multiple myeloma, Waldenström's macroglobulinemia, the heavy chain diseases, such as, for example, alpha chain disease, gamma chain disease, and mu chain disease, benign monoclonal gammopathy, and immunocytic amyloidosis, melanomas, breast cancer, lung cancer, bronchus cancer, colorectal cancer, prostate cancer, pancreatic cancer, stomach cancer, ovarian cancer, urinary bladder cancer, brain or central nervous system cancer, peripheral nervous system cancer, esophageal cancer, cervical cancer, uterine or endometrial cancer, cancer of the oral cavity or pharynx, liver cancer, kidney cancer, testicular cancer, biliary tract cancer, small bowel or appendix cancer, salivary gland cancer, thyroid gland cancer, adrenal gland cancer, osteosarcoma, chondrosarcoma, cancer of hematologic tissues, and the like. Other non-limiting examples of types of cancers applicable to the methods encompassed by the present invention include human sarcomas and carcinomas, e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, colorectal cancer, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, liver cancer, choriocarcinoma, seminoma, embryonal carcinoma, Wilms' tumor, cervical cancer, bone cancer, brain tumor, testicular cancer, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenstrom's macroglobulinemia, and heavy chain disease. In some embodiments, cancers are epithlelial in nature and include but are not limited to, bladder cancer, breast cancer, cervical cancer, colon cancer, gynecologic cancers, renal cancer, laryngeal cancer, lung cancer, oral cancer, head and neck cancer, ovarian cancer, pancreatic cancer, prostate cancer, or skin cancer. In other embodiments, the cancer is breast cancer, prostate cancer, lung cancer, or colon cancer. In still other embodiments, the epithelial cancer is non-small-cell lung cancer, nonpapillary renal cell carcinoma, cervical carcinoma, ovarian carcinoma (e.g., serous ovarian carcinoma), or breast carcinoma. The epithelial cancers may be characterized in various other ways including, but not limited to, serous, endometrioid, mucinous, clear cell, Brenner, or undifferentiated. In some embodiments, the cancer or tumor is melanoma and/or renal cell cancer (RCC).

The terms "conjoint therapy" and "combination therapy," as used herein, refer to the administration of two or more therapeutic substances, e.g., combinations of anti-immune checkpoint therapies, multiple inhibitors of an immune checkpoint of interest, combinations of immune checkpoint therapy with an inhibitor of PD-1, PD-L1, PD-L2, TIM, LAG, CTLA-4, and the like), and combinations thereof. The different agents comprising the combination therapy may be administered concomitant with, prior to, or following the administration of one or more therapeutic agents.

As used herein, the term "costimulate" with reference to activated immune cells includes the ability of a costimulatory molecule to provide a second, non-activating receptor mediated signal (a "costimulatory signal") that induces proliferation or effector function. For example, a costimulatory signal can result in cytokine secretion, e.g., in a T cell that has received a T cell-receptor-mediated signal. Immune cells that have received a cell-receptor mediated signal, e.g., via an activating receptor are referred to herein as "activated immune cells."

The term "determining a suitable treatment regimen for the subject" is taken to mean the determination of a treatment regimen (i.e., a single therapy or a combination of different therapies that are used for the prevention and/or treatment of the cancer in the subject) for a subject that is started, modified and/or ended based or essentially based or at least partially based on the results of the analysis according to the present invention. One example is determining whether to provide targeted therapy against a cancer to provide immunotherapy that generally increases immune responses against the cancer (e.g., immune checkpoint therapy). Another example is starting an adjuvant therapy after surgery whose purpose is to decrease the risk of recurrence, another would be to modify the dosage of a particular chemotherapy. The determination can, in addition to the results of the analysis according to the present invention, be based on personal characteristics of the subject to be treated. In most cases, the actual determination of the suitable treatment regimen for the subject will be performed by the attending physician or doctor.

The term "diagnosing cancer" includes the use of the methods, systems, and code encompassed by the present invention to determine the presence or absence of a cancer or subtype thereof in an individual. The term also includes methods, systems, and code for assessing the level of disease activity in an individual.

A molecule is "fixed" or "affixed" to a substrate if it is covalently or non-covalently associated with the substrate such that the substrate can be rinsed with a fluid (e.g. standard saline citrate, pH 7.4) without a substantial fraction of the molecule dissociating from the substrate.

The term "immune cell" refers to cells that play a role in the immune response. Immune cells are of hematopoietic origin, and include lymphocytes, such as B cells and T cells; natural killer cells; myeloid cells, such as monocytes, macrophages, eosinophils, mast cells, basophils, and granulocytes.

The term "immune checkpoint" refers to a group of molecules on the cell surface of CD4+ and/or CD8+ T cells that fine-tune immune responses by down-modulating or inhibiting an anti-tumor immune response. Immune checkpoint proteins are well known in the art and include, without limitation, CTLA-4, PD-1, VISTA, B7-H2, B7-H3, PD-L1, B7-H4, B7-H6, 2B4, ICOS, HVEM, PD-L2, CD160, gp49B, PIR-B, KIR family receptors, TIM-1, TIM-3, TIM-4, LAG-3, BTLA, SIRPalpha (CD47), CD48, 2B4 (CD244), B7.1, B7.2, ILT-2, ILT-4, TIGIT, and A2aR (see, for example, WO 2012/177624). The term further encompasses biologically active protein fragment, as well as nucleic acids encoding full-length immune checkpoint proteins and biologically active protein fragments thereof. In some embodiment, the term further encompasses any fragment according to homology descriptions provided herein.

"Immune checkpoint therapy" refers to the use of agents that inhibit immune checkpoint nucleic acids and/or proteins. Inhibition of one or more immune checkpoints can block or otherwise neutralize inhibitory signaling to thereby upregulate an immune response in order to more efficaciously treat cancer. Exemplary agents useful for inhibiting immune checkpoints include antibodies, small molecules, peptides, peptidomimetics, natural ligands, and derivatives of natural ligands, that can either bind and/or inactivate or inhibit immune checkpoint proteins, or fragments thereof; as well as RNA interference, antisense, nucleic acid aptamers, etc. that can downregulate the expression and/or activity of immune checkpoint nucleic acids, or fragments thereof. Exemplary agents for upregulating an immune response include antibodies against one or more immune checkpoint proteins block the interaction between the proteins and its natural receptor(s); a non-activating form of one or more immune checkpoint proteins (e.g., a dominant negative polypeptide); small molecules or peptides that block the interaction between one or more immune checkpoint proteins and its natural receptor(s); fusion proteins (e.g. the extracellular portion of an immune checkpoint inhibition protein fused to the Fc portion of an antibody or immunoglobulin) that bind to its natural receptor(s); nucleic acid molecules that block immune checkpoint nucleic acid transcription or translation; and the like. Such agents can directly block the interaction between the one or more immune checkpoints and its natural receptor(s) (e.g., antibodies) to prevent inhibitory signaling and upregulate an immune response. Alternatively, agents can indirectly block the interaction between one or more immune checkpoint proteins and its natural receptor(s) to prevent inhibitory signaling and upregulate an immune response. For example, a soluble version of an immune checkpoint protein ligand such as a stabilized extracellular domain can binding to its receptor to indirectly reduce the effective concentration of the receptor to bind to an appropriate ligand. In one embodiment, anti-PD-1 antibodies (e.g., Opdivo® (nivolumab) and Keytruda® (pembrolizumab)), anti-PD-L1 antibodies (e.g., Tecentriq® (atezolizumab)), anti-PD-L2 antibodies, and anti-CTLA-4 antibodies, either alone or in combination, are used to inhibit immune checkpoints.

"Ipilimumab" is a representative example of an immune checkpoint therapy. Ipilimumab (previously MDX-010; Medarex Inc., marketed by Bristol-Myers Squibb as YERVOY™) is a fully human anti-human CTLA-4 monoclonal antibody that blocks the binding of CTLA-4 to CD80 and CD86 expressed on antigen presenting cells, thereby, blocking the negative down-regulation of the immune responses elicited by the interaction of these molecules (see, for example, WO 2013/169971, U.S. Pat. Publ. 2002/0086014, and U.S. Pat. Publ. 2003/0086930.

"Nivolumab" is another representative example of an immune checkpoint therapy. Nivolumab (discovered by Medarex, developed by Medarex and Ono Pharmaceutical, and marketed by Bristol-Myers Squibb and Ono as Opdivo®) is a human IgG4 anti-PD-1 monoclonal antibody and works as a checkpoint inhibitor, blocking signals that would have prevented activated T cells from attacking the cancer, thus allowing the immune system to clear the cancer. It is used as a first line treatment for inoperable or metastatic melanoma in combination with ipilimumab if the cancer does not have a mutation in BRAF, as a second-line treatment following treatment with ipilimumab and if the cancer has a mutation in BRAF, with a BRAF inhibitor (Johnson et al. (2015) *Ther Adv Med Oncol.* 7:97-106), as a second-line treatment for squamous non-small cell lung cancer (Sundar et al. (2015) *Ther Adv Med Oncol.* 7:85-96), and as a second-line treatment for renal cell carcinoma. FDA has approved nivolumab for primary or metastatic urothelial carcinoma, the most common form of bladder cancer. It can be prescribed for locally advanced or metastatic form of the condition that experience disease progression during or following platinum-containing chemotherapy or have progression within 12 months of neoadjuvant or adjuvant treatment with platinum-containing chemotherapy.

The term "immune response" includes T cell mediated and/or B cell mediated immune responses. Exemplary immune responses include T cell responses, e.g., cytokine production and cellular cytotoxicity. In addition, the term immune response includes immune responses that are indirectly effected by T cell activation, e.g., antibody production (humoral responses) and activation of cytokine responsive cells, e.g., macrophages.

The term "immunotherapeutic agent" can include any molecule, peptide, antibody or other agent which can stimulate a host immune system to generate an immune response to a tumor or cancer in the subject. Various immunotherapeutic agents are useful in the compositions and methods described herein.

The term "inhibit" includes the decrease, limitation, or blockage, of, for example a particular action, function, or interaction. In some embodiments, cancer is "inhibited" if at least one symptom of the cancer is alleviated, terminated, slowed, or prevented. As used herein, cancer is also "inhibited" if recurrence or metastasis of the cancer is reduced, slowed, delayed, or prevented.

The term "interaction", when referring to an interaction between two molecules, refers to the physical contact (e.g., binding) of the molecules with one another. Generally, such an interaction results in an activity (which produces a biological effect) of one or both of said molecules.

An "isolated protein" refers to a protein that is substantially free of other proteins, cellular material, separation medium, and culture medium when isolated from cells or produced by recombinant DNA techniques, or chemical precursors or other chemicals when chemically synthesized. An "isolated" or "purified" protein or biologically active portion thereof is substantially free of cellular material or other contaminating proteins from the cell or tissue source from which the antibody, polypeptide, peptide or fusion protein is derived, or substantially free from chemical precursors or other chemicals when chemically synthesized.

The language "substantially free of cellular material" includes preparations of a polypeptide or fragment thereof, in which the protein is separated from cellular components of the cells from which it is isolated or recombinantly produced. In one embodiment, the language "substantially free of cellular material" includes preparations of a protein or fragment thereof, having less than about 30% (by dry weight) of other protein (also referred to herein as a "contaminating protein"), more preferably less than about 20% of other protein, still more preferably less than about 10% of other protein, and most preferably less than about 5% other protein. When antibody, polypeptide, peptide or fusion protein or fragment thereof, e.g., a biologically active fragment thereof, is recombinantly produced, it is also preferably substantially free of culture medium, i.e., culture medium represents less than about 20%, more preferably less than about 10%, and most preferably less than about 5% of the volume of the protein preparation.

A "kit" is any manufacture (e.g. a package or container) comprising at least one reagent, e.g. a probe or small molecule, for specifically detecting and/or affecting the expression of a marker encompassed by the present invention. The kit may be promoted, distributed, or sold as a unit for performing the methods encompassed by the present invention. The kit may comprise one or more reagents necessary to express a composition useful in the methods encompassed by the present invention. In certain embodiments, the kit may further comprise a reference standard, e.g., a nucleic acid encoding a protein that does not affect or regulate signaling pathways controlling cell growth, division, migration, survival or apoptosis. One skilled in the art can envision many such control proteins, including, but not limited to, common molecular tags (e.g., green fluorescent protein and beta-galactosidase), proteins not classified in any of pathway encompassing cell growth, division, migration, survival or apoptosis by GeneOntology reference, or ubiquitous housekeeping proteins. Reagents in the kit may be provided in individual containers or as mixtures of two or more reagents in a single container. In addition, instructional materials which describe the use of the compositions within the kit can be included.

The term "neoadjuvant therapy" refers to a treatment given before the primary treatment. Examples of neoadjuvant therapy can include chemotherapy, radiation therapy, and hormone therapy. For example, in treating breast cancer, neoadjuvant therapy can allows patients with large breast cancer to undergo breast-conserving surgery.

The terms "prevent," "preventing," "prevention," "prophylactic treatment," and the like refer to reducing the probability of developing a disease, disorder, or condition in a subject, who does not have, but is at risk of or susceptible to developing a disease, disorder, or condition.

The term "prognosis" includes a prediction of the probable course and outcome of cancer or the likelihood of recovery from the disease. In some embodiments, the use of statistical algorithms provides a prognosis of cancer in an individual. For example, the prognosis can be surgery, development of a clinical subtype of cancer (e.g., solid tumors, such as lung cancer, melanoma, and renal cell carcinoma), development of one or more clinical factors, development of intestinal cancer, or recovery from the disease.

The term "response to immune checkpoint therapy" or "response to therapy" relates to any response of the hyperproliferative disorder (e.g., cancer) to a therapy, such as an immune checkpoint therapy like immune checkpoint therapy, preferably to a change in tumor mass and/or volume after initiation of neoadjuvant or adjuvant chemotherapy. Hyperproliferative disorder response may be assessed, for example for efficacy or in a neoadjuvant or adjuvant situation, where the size of a tumor after systemic intervention can be compared to the initial size and dimensions as measured by CT, PET, mammogram, ultrasound or palpation. Responses may also be assessed by caliper measurement or pathological examination of the tumor after biopsy or surgical resection. Response may be recorded in a quantitative fashion like percentage change in tumor volume or in a qualitative fashion like "pathological complete response" (pCR), "clinical complete remission" (cCR), "clinical partial remission" (cPR), "clinical stable disease" (cSD), "clinical progressive disease" (cPD) or other qualitative criteria. Assessment of hyperproliferative disorder response may be done early after the onset of neoadjuvant or adjuvant therapy, e.g., after a few hours, days, weeks or preferably after a few months. A typical endpoint for response assessment is upon termination of neoadjuvant chemotherapy or upon surgical removal of residual tumor cells and/or the tumor bed. This is typically three months after initiation of neoadjuvant therapy. In some embodiments, clinical efficacy of the therapeutic treatments described herein may be determined by measuring the clinical benefit rate (CBR). The clinical benefit rate is measured by determining the sum of the percentage of patients who are in complete remission (CR), the number of patients who are in partial remission (PR) and the number of patients having stable disease (SD) at a time point at least 6 months out from the end of therapy. The shorthand for this formula is CBR=CR+PR+SD over 6 months. In some embodiments, the CBR for a particular cancer therapeutic regimen is at least 25%, 30%, 35%, 40%, 45%, 50%, 55%, 60%, 65%, 70%, 75%, 80%, 85%, or more. Additional criteria for evaluating the response to cancer therapies are related to "survival," which includes all of the following: survival until mortality, also known as overall survival (wherein said mortality may be either irrespective of cause or tumor related); "recurrence-free survival" (wherein the term recurrence shall include both localized and distant recurrence); metastasis free survival; disease free survival (wherein the term disease shall include cancer and diseases associated therewith). The length of said survival may be calculated by reference to a defined start point (e.g., time of diagnosis or start of treatment) and end point (e.g., death, recurrence or metastasis). In addition, criteria for efficacy of treatment can be expanded to include response to chemotherapy, probability of survival, probability of metastasis within a given time period, and probability of tumor recurrence. For example, in order to determine appropriate threshold values, a particular cancer therapeutic regimen can be administered to a population of subjects and the outcome can be correlated to measurements that were determined prior to administration of any cancer therapy. The outcome measurement may be pathologic response to therapy given in the neoadjuvant setting. Alternatively, outcome measures, such as overall survival and disease-free survival can be monitored over a period of time for subjects following cancer therapy for whom measurement values are known. In certain embodiments, the doses administered are standard doses known in the art for cancer therapeutic agents. The period of time for which subjects are monitored can vary. For example, subjects may be monitored for at least 1, 2, 3, 4, 5, 6, 7, 8, 9, 10, 11, 12, 13, 14, 16, 17, 18, 19, 20 weeks or longer, such as 2, 4, 6, 8, 10, 12, 14, 16, 18, 20, 25, 30, 35, 45, 50, 55, or 60 months. Measurement threshold values that correlate to outcome of a cancer therapy can be determined using well-known methods in the art, such as those described in the Examples section.

The term "resistance" refers to an acquired or natural resistance of a cancer sample or a mammal to a cancer therapy (i.e., being nonresponsive to or having reduced or limited response to the therapeutic treatment), such as having a reduced response to a therapeutic treatment by 25% or more, for example, 30%, 40%, 50%, 60%, 70%, 80%, or more, to 2-fold, 3-fold, 4-fold, 5-fold, 10-fold, 15-fold, 20-fold or more. The reduction in response can be measured by comparing with the same cancer sample or mammal before the resistance is acquired, or by comparing with a different cancer sample or a mammal who is known to have no resistance to the therapeutic treatment. A typical acquired resistance to chemotherapy is called "multidrug resistance." The multidrug resistance can be mediated by P-glycoprotein or can be mediated by other mechanisms, or it can occur when a mammal is infected with a multi-drug-resistant microorganism or a combination of microorganisms. The determination of resistance to a therapeutic treatment is routine in the art and within the skill of an ordinarily skilled clinician, for example, can be measured by cell proliferative assays and cell death assays as described herein as "sensitizing." In some embodiments, the term "reverses resistance" means that the use of a second agent in combination with a primary cancer therapy (e.g., chemotherapeutic or radiation therapy) is able to produce a significant decrease in tumor volume at a level of statistical significance (e.g., $p<0.05$) when compared to tumor volume of untreated tumor in the circumstance where the primary cancer therapy (e.g., chemotherapeutic or radiation therapy) alone is unable to produce a statistically significant decrease in tumor volume compared to tumor volume of untreated tumor. This generally applies to tumor volume measurements made at a time when the untreated tumor is growing log rhythmically.

The terms "response" or "responsiveness" refers to an anti-cancer response, e.g. in the sense of reduction of tumor size or inhibiting tumor growth. The terms can also refer to an improved prognosis, for example, as reflected by an increased time to recurrence, which is the period to first recurrence censoring for second primary cancer as a first event or death without evidence of recurrence, or an increased overall survival, which is the period from treatment to death from any cause. To respond or to have a response means there is a beneficial endpoint attained when exposed to a stimulus. Alternatively, a negative or detrimental symptom is minimized, mitigated or attenuated on exposure to a stimulus. It will be appreciated that evaluating the likelihood that a tumor or subject will exhibit a favorable response is equivalent to evaluating the likelihood that the tumor or subject will not exhibit favorable response (i.e., will exhibit a lack of response or be non-responsive). The term "sample" can be whole blood, plasma, serum, saliva, urine, stool (e.g., feces), tears, and any other bodily fluid (e.g., as described above under the definition of "body fluids"), or a tissue sample (e.g., biopsy) such as a small intestine, colon sample, or surgical resection tissue.

The term "sensitize" means to alter cancer cells or tumor cells in a way that allows for more effective treatment of the associated cancer with a cancer therapy (e.g., anti-immune checkpoint, chemotherapeutic, and/or radiation therapy). In some embodiments, normal cells are not affected to an extent that causes the normal cells to be unduly injured by the immune checkpoint therapy. An increased sensitivity or a reduced sensitivity to a therapeutic treatment is measured according to a known method in the art for the particular treatment and methods described herein below, including, but not limited to, cell proliferative assays (Tanigawa N, Kern D H, Kikasa Y, Morton D L, Cancer Res 1982; 42: 2159-2164), cell death assays (Weisenthal L M, Shoemaker R H, Marsden J A, Dill P L, Baker J A, Moran E M, Cancer Res 1984; 94: 161-173; Weisenthal L M, Lippman M E, Cancer Treat Rep 1985; 69: 615-632; Weisenthal L M, In: Kaspers G J L, Pieters R, Twentyman P R, Weisenthal L M, Veerman A J P, eds. Drug Resistance in Leukemia and Lymphoma. Langhorne, P A: Harwood Academic Publishers, 1993: 415-432; Weisenthal L M, Contrib Gynecol Obstet 1994; 19: 82-90). The sensitivity or resistance may also be measured in animal by measuring the tumor size reduction over a period of time, for example, 6 month for human and 4-6 weeks for mouse. A composition or a method sensitizes response to a therapeutic treatment if the increase in treatment sensitivity or the reduction in resistance is 25% or more, for example, 30%, 40%, 50%, 60%, 70%, 80%, or more, to 2-fold, 3-fold, 4-fold, 5-fold, 10-fold, 15-fold, 20-fold or more, compared to treatment sensitivity or resistance in the absence of such composition or method. The determination of sensitivity or resistance to a therapeutic treatment is routine in the art and within the skill of an ordinarily skilled clinician. It is to be understood that any method described herein for enhancing the efficacy of a cancer therapy can be equally applied to methods for sensitizing hyperproliferative or otherwise cancerous cells (e.g., resistant cells) to the cancer therapy.

The term "synergistic effect" refers to the combined effect of two or more anti-immune checkpoint agents can be greater than the sum of the separate effects of the anticancer agents alone.

The term "subject" refers to any healthy animal, mammal or human, or any animal, mammal or human afflicted with a cancer, e.g., lung, ovarian, pancreatic, liver, breast, prostate, and colon carcinomas, as well as melanoma and multiple myeloma. The term "subject" is interchangeable with "patient."

The term "survival" includes all of the following: survival until mortality, also known as overall survival (wherein said mortality may be either irrespective of cause or tumor related); "recurrence-free survival" (wherein the term recurrence shall include both localized and distant recurrence); metastasis free survival; disease free survival (wherein the term disease shall include cancer and diseases associated therewith). The length of said survival may be calculated by reference to a defined start point (e.g. time of diagnosis or start of treatment) and end point (e.g. death, recurrence or metastasis). In addition, criteria for efficacy of treatment can be expanded to include response to chemotherapy, probability of survival, probability of metastasis within a given time period, and probability of tumor recurrence.

The term "therapeutic effect" refers to a local or systemic effect in animals, particularly mammals, and more particularly humans, caused by a pharmacologically active substance. The term thus means any substance intended for use in the diagnosis, cure, mitigation, treatment or prevention of disease or in the enhancement of desirable physical or mental development and conditions in an animal or human. The phrase "therapeutically-effective amount" means that amount of such a substance that produces some desired local or systemic effect at a reasonable benefit/risk ratio applicable to any treatment. In certain embodiments, a therapeutically effective amount of a compound will depend on its therapeutic index, solubility, and the like. For example, certain compounds discovered by the methods encompassed by the present invention may be administered in a sufficient amount to produce a reasonable benefit/risk ratio applicable to such treatment.

The terms "therapeutically-effective amount" and "effective amount" as used herein means that amount of a compound, material, or composition comprising a compound encompassed by the present invention which is effective for producing some desired therapeutic effect in at least a sub-population of cells in an animal at a reasonable benefit/risk ratio applicable to any medical treatment. Toxicity and therapeutic efficacy of subject compounds may be determined by standard pharmaceutical procedures in cell cultures or experimental animals, e.g., for determining the $LD_{50}$ and the $ED_{50}$. Compositions that exhibit large therapeutic indices are preferred. In some embodiments, the $LD_{50}$ (lethal dosage) can be measured and can be, for example, at least 10%, 20%, 30%, 40%, 50%, 60%, 70%, 80%, 90%, 100%, 200%, 300%, 400%, 500%, 600%, 700%, 800%, 900%, 1000% or more reduced for the agent relative to no administration of the agent. Similarly, the $ED_{50}$ (i.e., the concentration which achieves a half-maximal inhibition of symptoms) can be measured and can be, for example, at least 10%, 20%, 30%, 40%, 50%, 60%, 70%, 80%, 90%, 100%, 200%, 300%, 400%, 500%, 600%, 700%, 800%, 900%, 1000% or more increased for the agent relative to no administration of the agent. Also, Similarly, the $IC_{50}$ (i.e., the concentration which achieves half-maximal cytotoxic or cytostatic effect on cancer cells) can be measured and can be, for example, at least 10%, 20%, 30%, 40%, 50%, 60%, 70%, 80%, 90%, 100%, 200%, 300%, 400%, 500%, 600%, 700%, 800%, 900%, 1000% or more increased for the agent relative to no administration of the agent. In some embodiments, cancer cell growth in an assay can be inhibited by at least about 10%, 15%, 20%, 25%, 30%, 35%, 40%, 45%, 50%, 55%, 60%, 65%, 70%, 75%, 80%, 85%, 90%, 95%, or even 100%. In another embodiment, at least about a 10%, 15%, 20%, 25%, 30%, 35%, 40%, 45%, 50%, 55%, 60%, 65%, 70%, 75%, 80%, 85%, 90%, 95%, or even 100% decrease in a solid malignancy can be achieved.

As used herein, the term "unresponsiveness" includes refractivity of immune cells to stimulation, e.g., stimulation via an activating receptor or a cytokine. Unresponsiveness can occur, e.g., because of exposure to immunosuppressants or exposure to high doses of antigen. As used herein, the term "anergy" or "tolerance" includes refractivity to activating receptor-mediated stimulation. Such refractivity is generally antigen-specific and persists after exposure to the tolerizing antigen has ceased. For example, anergy in T cells (as opposed to unresponsiveness) is characterized by lack of cytokine production, e.g., IL-2. T cell anergy occurs when T cells are exposed to antigen and receive a first signal (a T cell receptor or CD-3 mediated signal) in the absence of a second signal (a costimulatory signal). Under these conditions, reexposure of the cells to the same antigen (even if reexposure occurs in the presence of a costimulatory polypeptide) results in failure to produce cytokines and, thus, failure to proliferate. Anergic T cells can, however, proliferate if cultured with cytokines (e.g., IL-2). For example, T cell anergy can also be observed by the lack of IL-2 production by T lymphocytes as measured by ELISA or by a proliferation assay using an indicator cell line. Alternatively, a reporter gene construct can be used. For example, anergic T cells fail to initiate IL-2 gene transcription induced by a heterologous promoter under the control of the 5' IL-2 gene enhancer or by a multimer of the AP1 sequence that can be found within the enhancer (Kang et al. (1992) *Science* 257:1134). The terms "antigen presenting cells" or "APCs" include both intact whole cells as well as other molecules which are capable of inducing the presentation of one or more antigens, preferably with class I MEW molecules. Examples of suitable APCs are discussed in detail below and include, but are not limited to, whole cells, such as macrophages, dendritic cells, B cells; purified MEW class I molecules complexed to β2-microglobulin; and foster antigen presenting cells.

Dendritic cells (DCs) are potent APCs. DCs are minor constituents of various immune organs, such as spleen, thymus, lymph node, epidermis, and peripheral blood. For instance, DCs represent merely about 1% of crude spleen (see Steinman et al. (1979) J. Exp. Med 149: 1) or epidermal cell suspensions (see Schuler et al. (1985) J. Exp. Med 161:526; Romani et al. J Invest. Dermatol (1989) 93: 600) and 0.1-1% of mononuclear cells in peripheral blood (see Freudenthal et al. Proc. Natl Acad Sci USA (1990) 87: 7698). Methods for isolating DCs from peripheral blood or bone marrow progenitors are known in the art (see Inaba et al. (1992) J. Exp. Med 175:1157; Inaba et al. (1992) J. Exp, Med 176: 1693-1702; Romani et al. (1994) J. Exp. Med. 180: 83-93; Sallusto et al. (1994) J. Exp. Med 179: 11 09-1118). Preferred methods for isolation and culturing of DCs are described in Bender et al. (1996) J. Immun. Meth. 196:121-135 and Romani et al. (1996) J. Immun. Meth 196:137-151.

Dendritic cells (DCs) represent a complex network of antigen presenting cells that are primarily responsible for initiation of primary immunity and the modulation of immune response (see Avigan, Blood Rev. 13:51-64 (1999); Banchereau et al. Nature 392:245-52 (1998)). Partially mature DCs are located at sites of antigen capture and excel at the internalization and processing of exogenous antigens, but are poor stimulators of T cell responses. Presentation of antigen by immature DCs may induce T cell tolerance (see Dhodapkar et al. J Exp Med. 193:233-38 (2001)). Upon activation, DCs undergo maturation characterized by the increased expression of costimulatory molecules and CCR7, the chemokine receptor which promotes migration to sites of T cell traffic in the draining lymph nodes. Tumor or cancer cells inhibit DC development through the secretion of IL-10, TGF-β), and VEGF resulting in the accumulation of immature DCs in the tumor bed that potentially suppress anti-tumor responses (see Allavena et al, Eur. J. Immunol. 28:359-69 (1998); Gabrilovich et al. Clin Cancer Res. 3:483-90 (1997); Gabrilovich et al. Blood 92:4150-66 (1998); Gabrilovich, Nat Rev Immunol 4:941-52 (2004)). Conversely, activated DCs can be generated by cytokine-mediated differentiation of DC progenitors ex vivo. DC maturation and function can be further enhanced by exposure to the toll-like receptor 9 agonist, CPG ODN. Moreover, DCs can be manipulated to present tumor antigens potently stimulate anti-tumor immunity (see Asavaroenhchai et al. Proc Natl Acad Sci USA 99:931-36 (2002); Ashley et al. J Exp Med 186:1177-82 (1997)).

The term "autogeneic" or "autologous," as used herein, indicates the origin of a cell. Thus, a cell being administered to an individual (the "recipient") is autogeneic if the cell was derived from that individual (the "donor") or a genetically identical individual (i.e., an identical twin of the individual). An autogeneic cell can also be a progeny of an autogeneic cell. The term also indicates that cells of different cell types are derived from the same donor or genetically identical donors. Thus, an effector cell and an antigen presenting cell are said to be autogeneic if they were derived from the same donor or from an individual genetically identical to the donor, or if they are progeny of cells derived from the same donor or from an individual genetically identical to the donor.

II. Subjects, Tumor Cells, and Dendritic Cells

In one embodiment, the subject who is treated with the disclosed methods is a mammal (e.g., mouse, rat, primate, non-human mammal, domestic animal, such as a dog, cat, cow, horse, and the like), and is preferably a human.

In another embodiment of the methods encompassed by the present invention, the subject has not undergone treatment, such as chemotherapy, radiation therapy, targeted therapy, and/or immune checkpoint therapy. In still another embodiment, the subject has undergone treatment, such as chemotherapy, radiation therapy, targeted therapy, and/or immune checkpoint therapy.

In certain embodiments, the subject has had surgery to remove cancerous or precancerous tissue. In other embodiments, the cancerous tissue has not been removed, e.g., the cancerous tissue may be located in an inoperable region of the body, such as in a tissue that is essential for life, or in a region where a surgical procedure would cause considerable risk of harm to the patient.

The methods encompassed by the present invention can be used to treat a subject who has cancer. In one embodiment, the cancer is one for which an immune checkpoint therapy (e.g., anti-PD-1 blocking antibody, anti-PD-L1 blocking antibody, CTLA-4 blocking antibody, and the like) is FDA-approved for treatment, such as those described in the Examples. In one embodiment, the cancers are solid tumors, such as lung cancer such as non-small cell lung cancer, bladder cancer, melanoma such as metastatic melanoma, and/or renal cell carcinoma. In another embodiment, the cancer is an epithelial cancer such as, but not limited to, brain cancer (e.g., glioblastomas) bladder cancer, breast cancer, cervical cancer, colon cancer, gynecologic cancers, renal cancer, laryngeal cancer, lung cancer, oral cancer, head and neck cancer, ovarian cancer, pancreatic cancer, prostate cancer, or skin cancer. In still other embodiments, the cancer is breast cancer, prostate cancer, lung cancer, or colon cancer. In still other embodiments, the epithelial cancer is non-small-cell lung cancer, nonpapillary renal cell carcinoma, cervical carcinoma, ovarian carcinoma (e.g., serous ovarian carcinoma), or breast carcinoma. The epithelial cancers may be characterized in various other ways including, but not limited to, serous, endometrioid, mucinous, clear cell, brenner, or undifferentiated. In yet other embodiments, the cancer is a mesenchymal cancer, such as sarcoma.

The tumor cells contemplated for use in connection with the present invention include, but are not limited to, tumor cells from breast cancer cells, ovarian cancer cells, pancreatic cancer cells, prostate gland cancer cells, renal cancer cells, lung cancer cells, urothelial cancer cells, colon cancer cells, rectal cancer cells, or hematological cancer cells. For example, hematological cancer cells include, but are not limited to, acute myeloid leukemia cells, acute lymphoid leukemia cells, multiple myeloma cells, and non-Hodgkin's lymphoma cells. Moreover, those skilled in the art would recognize that any tumor cell may be used in any of the methods encompassed by the present invention.

DCs can be obtained from bone marrow cultures, peripheral blood, spleen, or any other appropriate tissue of a mammal using protocols known in the art. Bone marrow contains DC progenitors, which, upon treatment with cytokines, such as granulocyte-macrophage colony-stimulating factor ("'GM-CSF") and interleukin 4 ("IL-4"), proliferate and differentiate into DCs. Tumor necrosis cell factor (TNF) is optionally used alone or in conjunction with GM-CSF and/or IL-4 to promote maturation of DCs. DCs obtained from bone marrow are relatively immature (as compared to, for instance, spleen DCs). GMCSF/IL-4 stimulated DC express MEW class I and class II molecules, B7-1, B7-2, ICAM, CD40 and variable levels of CD83. These immature DCs are more amenable to fusion (or antigen uptake) than the more mature DCs found in spleen, whereas more mature DCs are relatively more effective antigen presenting cells. Peripheral blood also contains relatively immature DCs or DC progenitors, which can propagate and differentiate in the presence of appropriate cytokines such as GM-CSF and—which can also be used in fusions.

Preferably, the DCs are obtained from peripheral blood. For example, the DCs are obtained from the patients' peripheral blood after it has been documented that the patient is in complete remission.

The DC can be made hyperactive prior to fusion or after fusion. DCs can be made hyperactive by any method know in the art. For example, DCs are made hyperactive by contacting the DC or DC fusion with a priming agent followed by an activating agent. Exemplary priming agents include CpG DNA or LPS. Activating agents include for example oxidized phospholipids.

In some embodiments, DCs have sufficient viability prior to fusion, such as at least 70%, at least 75%, at least 80%, or greater.

Prior to fusion, the population of the DCs are generally free of components used during the production, e.g., cell culture components and substantially free of mycoplasm, endotoxin, and microbial contamination. Preferably, the population of DCs has less than 5, 3, 2, or 1 CFU/swab. Most preferably, the population of DCs has 0 CFU/swab.

The fusion product can be used directly after the fusion process (e.g., in antigen discovery screening methods or in therapeutic methods) or after a short culture period.

The hyperactive cell fusions can be irradiated prior to clinical use. Irradiation induces expression of cytokines, which promotes immune effector cell activity. Irradiation also prevents the cells from replicating, thereby reducing or eliminating any risk of oncogenesis.

In the event that the fused DCs lose certain DC characteristics, such as expression of the APC-specific T-cell stimulating molecules, primary fused cells can be re-fused with dendritic cells to restore the DC phenotype. The re-fused cells (i.e., secondary fused cells) are found to be highly potent APCs. The fused cells can be re-fused with the dendritic or non-dendritic parental cells as many times as desired.

Cell fusions that express WIC class II molecules, B7, or other desired T-cell stimulating molecules can also be selected by panning or fluorescence-activated cell sorting with antibodies against these molecules.

Fusion can be carried out with well-known methods, such as those using polyethylene glycol ("PEG") or electrofusion. Alternatively, the cDNA-NC/NPs or cDNA vesicles or tumor organoids or spheroids can fuse with DCs in the absence of PEG or electrofusion. DCs are autologous or allogeneic (see. e.g., U.S. Pat. No. 6,653,848, which is herein incorporated by reference in its entirety).

After fusion, unfused DCs usually die off in a few days in culture, and the fused cells can be separated from the unfused, parental, non-dendritic cells by the following two methods, both of which yield fused cells of approximately 50% or higher purity, i.e., the fused cell preparations contain less than 50%, and often less than 30%, unfused cells.

Specifically, one method of separating unfused cells/vehicles from fused cells is based on the different adherence properties between the fused cells and the vehicles or WIC I/II null cells expressing tumor antigens. It has been found that the fused cells are generally lightly adherent to tissue culture containers. Thus, if the cells expressing tumor antigens are much more adherent, the post-fusion cell mixtures can be cultured in an appropriate medium for a short period of time (e.g., 5-10 days).

Subsequently, cell fusions can be gently dislodged and aspirated off while the WIC I/II null cells expressing tumor antigens or are firmly attached to the tissue culture containers. Conversely, if the cells expressing tumor antigens are in suspension, after the culture period, they can be gently aspirated off while leaving the DC fusions loosely attached to the containers. Alternatively, the hybrids are used directly without an in vitro cell culturing step.

The cell fusions obtained by the above-described methods typically retain the phenotypic characteristics of DCs. For instance, these fusions express T-cell stimulating molecules such as MHC class II protein, B7-L B7-2, and adhesion molecules characteristic of APCs such as ICAM-I. The fusions also continue to express cell-surface antigens of the tumor cells such as MUCI, and are therefore useful for inducing immunity against the cell surface antigens.

In the event that the fusions lose certain DC characteristics such as expression of the APC-specific T-cell stimulating molecules, they (i.e., primary fusions) can be re-fused with dendritic cells to restore the DC phenotype. The re-fused cells (i.e., secondary fusions) are found to be highly potent APCs, and in some cases, have even less tumorigenicity than primary fusions. The fusions can be re-fused with the dendritic cell as many times as desired. The DCs can be made hyperactive prior to or after re-fusion.

The cell fusions can be frozen before administration. The fusions can be frozen in a solution containing 10% DMSO in 90% heat inactivated autologous plasma.

III. Anti-Cancer Therapies

In some embodiments, therapies including fusion cells, CAR-T cells, NK cells, educated T cells, and or immune checkpoint therapies can be used. Combination therapies are also contemplated and can comprise, for example, one or more chemotherapeutic agents and radiation, one or more chemotherapeutic agents and immunotherapy, or one or more chemotherapeutic agents, radiation and chemotherapy, each combination of which can be with immune checkpoint therapy.

In some embodiments, the immune checkpoint therapy includes a PD-1 and/or a PD-L1 inhibitor. In some examples, the at least one anti-PD-1 agent is selected from the group consisting of cemiplimab (REGN2810), nivolumab (BMS-936558, MDX-1106, ONO-4538), pembrolizumab (MK-3475, SCH 900475), SHR1210, sintilimab (IBI308), spartalizumab (PDR001), tislelizumab (BGB-A317), pidilizumab, BCD-100, toripalimab (JS001), PF-06801591, AB122, AK105, AMG 404, BCD-100, BI 754091, F520, HLX10, HX008, JTX-4014, LZM009, MEDI0680, MGA012, Sym021, TSR-042, PSB205, MGD019, MGD013, AK104, XmAb20717, RO7121661, and CX-188. In some examples, the list of anti-PD-L1 agents is selected from the group consisting of atezolizumab (MPDL3280A, RG7446, RO5541267), durvalumab (MEDI4736, MEDI-4736), avelumab (MSB0010718C), FS118, BCD-135, BGB-A333, CBT-502, CK-301, CS1001, FAZ053, HLX20, KN035, MDX-1105, MSB2311, SHR-1316, TG-1501, ZKAB001, INBRX-105, MCLA-145, KN046, M7824, and LY3415244.

The term "targeted therapy" refers to administration of agents that selectively interact with a chosen biomolecule to thereby treat cancer.

Immunotherapy is one form of targeted therapy that may comprise, for example, the use of cancer vaccines and/or sensitized antigen presenting cells. For example, an oncolytic virus is a virus that is able to infect and lyse cancer cells, while leaving normal cells unharmed, making them potentially useful in cancer therapy. Replication of oncolytic viruses both facilitates tumor cell destruction and also produces dose amplification at the tumor site. They may also act as vectors for anticancer genes, allowing them to be specifically delivered to the tumor site. The immunotherapy can involve passive immunity for short-term protection of a host, achieved by the administration of pre-formed antibody directed against a cancer antigen or disease antigen (e.g., administration of a monoclonal antibody, optionally linked to a chemotherapeutic agent or toxin, to a tumor antigen). Immunotherapy can also focus on using the cytotoxic lymphocyte-recognized epitopes of cancer cell lines. Alternatively, antisense polynucleotides, ribozymes, RNA interference molecules, triple helix polynucleotides and the like, can be used to selectively modulate biomolecules that are linked to the initiation, progression, and/or pathology of a tumor or cancer. In one embodiment, agents that modulate adenosine, adenosine precursors, and/or adenosine metabolites are useful immunotherapeutic agents according to the present invention and are well-known in the art, as described below, such as adenosine receptor antagonists, agents that impair adenosine production, agents that metabolize adenosine, and the like.

The term "untargeted therapy" refers to administration of agents that do not selectively interact with a chosen biomolecule yet treat cancer. Representative examples of untargeted therapies include, without limitation, chemotherapy, gene therapy, and radiation therapy.

In one embodiment, chemotherapy is used. Chemotherapy includes the administration of a chemotherapeutic agent. Such a chemotherapeutic agent may be, but is not limited to, those selected from among the following groups of compounds: platinum compounds, cytotoxic antibiotics, antimetabolites, anti-mitotic agents, alkylating agents, arsenic compounds, DNA topoisomerase inhibitors, taxanes, nucleoside analogues, plant alkaloids, and toxins; and synthetic derivatives thereof. Exemplary compounds include, but are not limited to, alkylating agents: cisplatin, treosulfan, and trofosfamide; plant alkaloids: vinblastine, paclitaxel, docetaxol; DNA topoisomerase inhibitors: teniposide, crisnatol, and mitomycin; anti-folates: methotrexate, mycophenolic acid, and hydroxyurea; pyrimidine analogs: 5-fluorouracil, doxifluridine, and cytosine arabinoside; purine analogs: mercaptopurine and thioguanine; DNA antimetabolites: 2'-deoxy-5-fluorouridine, aphidicolin glycinate, and pyrazoloimidazole; and antimitotic agents: halichondrin, colchicine, and rhizoxin. Compositions comprising one or more chemotherapeutic agents (e.g., FLAG, CHOP) may also be used. FLAG comprises fludarabine, cytosine arabinoside (Ara-C) and G-CSF. CHOP comprises cyclophosphamide, vincristine, doxorubicin, and prednisone. In another embodiments, PARP (e.g., PARP-1 and/or PARP-2) inhibitors are used and such inhibitors are well known in the art (e.g., Olaparib, ABT-888, BSI-201, BGP-15 (N-Gene Research Laboratories, Inc.); INO-1001 (Inotek Pharmaceuticals Inc.); PJ34 (Soriano et al., 2001; Pacher et al., 2002b); 3-aminobenzamide (Trevigen); 4-amino-1, 8-naphthalimide; (Trevigen); 6(5H)-phenanthridinone (Trevigen); benzamide (U.S. Pat. No. Re. 36,397); and NU1025 (Bowman et al.). The mechanism of action is generally related to the ability of PARP inhibitors to bind PARP and decrease its activity. PARP catalyzes the conversion of .beta.-nicotinamide adenine dinucleotide (NAD+) into nicotinamide and poly-ADP-ribose (PAR). Both poly (ADP-ribose) and PARP have been linked to regulation of transcription, cell proliferation, genomic stability, and carcinogenesis (Bouchard V. J. et. al. Experimental Hematology, Volume 31, Number 6, June 2003, pp. 446-454(9); Herceg Z.; Wang Z.-Q. Mutation Research/Fundamental and Molecular Mechanisms of Mutagenesis, Volume 477, Number 1, 2 Jun. 2001, pp. 97-110(14)). Poly(ADP-ribose) polymerase 1 (PARP1) is a key molecule in the repair of DNA single-strand breaks (SSBs) (de Murcia J. et al. 1997. Proc Natl Acad Sci USA 94:7303-7307; Schreiber V, Dantzer F, Ame J C, de Murcia G (2006) Nat Rev Mol Cell Biol 7:517-528; Wang Z Q, et al. (1997) Genes Dev 11:2347-2358). Knockout of SSB repair by inhibition of PARP1 function induces DNA double-strand breaks (DSBs) that can trigger synthetic lethality in cancer cells with defective homology-directed DSB repair (Bryant H E, et al. (2005) Nature 434:913-917; Farmer H, et al. (2005) Nature 434:917-921). The foregoing examples of chemotherapeutic agents are illustrative, and are not intended to be limiting.

In another embodiment, radiation therapy is used. The radiation used in radiation therapy can be ionizing radiation. Radiation therapy can also be gamma rays, X-rays, or proton beams. Examples of radiation therapy include, but are not limited to, external-beam radiation therapy, interstitial implantation of radioisotopes (I-125, palladium, iridium), radioisotopes such as strontium-89, thoracic radiation therapy, intraperitoneal P-32 radiation therapy, and/or total abdominal and pelvic radiation therapy. For a general overview of radiation therapy, see Hellman, Chapter 16: Principles of Cancer Management: Radiation Therapy, 6th edition, 2001, DeVita et al., eds., J. B. Lippencott Company, Philadelphia. The radiation therapy can be administered as external beam radiation or teletherapy wherein the radiation is directed from a remote source. The radiation treatment can also be administered as internal therapy or brachytherapy wherein a radioactive source is placed inside the body close to cancer cells or a tumor mass. Also encompassed is the use of photodynamic therapy comprising the administration of photosensitizers, such as hematoporphyrin and its derivatives, Vertoporfin (BPD-MA), phthalocyanine, photosensitizer Pc4, demethoxy-hypocrellin A; and 2BA-2-DMHA.

In another embodiment, hormone therapy is used. Hormonal therapeutic treatments can comprise, for example, hormonal agonists, hormonal antagonists (e.g., flutamide, bicalutamide, tamoxifen, raloxifene, leuprolide acetate (LUPRON), LH-RH antagonists), inhibitors of hormone biosynthesis and processing, and steroids (e.g., dexamethasone, retinoids, deltoids, betamethasone, cortisol, cortisone, prednisone, dehydrotestosterone, glucocorticoids, mineralocorticoids, estrogen, testosterone, progestins), vitamin A derivatives (e.g., all-trans retinoic acid (ATRA)); vitamin D3 analogs; antigestagens (e.g., mifepristone, onapristone), or antiandrogens (e.g., cyproterone acetate).

In another embodiment, hyperthermia, a procedure in which body tissue is exposed to high temperatures (up to 106° F.) is used. Heat may help shrink tumors by damaging cells or depriving them of substances they need to live. Hyperthermia therapy can be local, regional, and whole-body hyperthermia, using external and internal heating devices. Hyperthermia is almost always used with other forms of therapy (e.g., radiation therapy, chemotherapy, and biological therapy) to try to increase their effectiveness. Local hyperthermia refers to heat that is applied to a very small area, such as a tumor. The area may be heated externally with high-frequency waves aimed at a tumor from a device outside the body. To achieve internal heating, one of several types of sterile probes may be used, including thin, heated wires or hollow tubes filled with warm water; implanted microwave antennae; and radiofrequency electrodes. In regional hyperthermia, an organ or a limb is heated. Magnets and devices that produce high energy are placed over the region to be heated. In another approach, called perfusion, some of the patient's blood is removed, heated, and then pumped (perfused) into the region that is to be heated internally. Whole-body heating is used to treat metastatic cancer that has spread throughout the body. It can be accomplished using warm-water blankets, hot wax, inductive coils (like those in electric blankets), or thermal chambers (similar to large incubators). Hyperthermia does not cause any marked increase in radiation side effects or complications. Heat applied directly to the skin, however, can cause discomfort or even significant local pain in about half the patients treated. It can also cause blisters, which generally heal rapidly.

In still another embodiment, photodynamic therapy (also called PDT, photoradiation therapy, phototherapy, or photochemotherapy) is used for the treatment of some types of cancer. It is based on the discovery that certain chemicals known as photosensitizing agents can kill one-celled organisms when the organisms are exposed to a particular type of light. PDT destroys cancer cells through the use of a fixed-frequency laser light in combination with a photosensitizing agent. In PDT, the photosensitizing agent is injected into the bloodstream and absorbed by cells all over the body. The agent remains in cancer cells for a longer time than it does in normal cells. When the treated cancer cells are exposed to laser light, the photosensitizing agent absorbs the light and produces an active form of oxygen that destroys the treated cancer cells. Light exposure must be timed carefully so that it occurs when most of the photosensitizing agent has left healthy cells but is still present in the cancer cells. The laser light used in PDT can be directed through a fiber-optic (a very thin glass strand). The fiber-optic is placed close to the cancer to deliver the proper amount of light. The fiber-optic can be directed through a bronchoscope into the lungs for the treatment of lung cancer or through an endoscope into the esophagus for the treatment of esophageal cancer. An advantage of PDT is that it causes minimal damage to healthy tissue. However, because the laser light currently in use cannot pass through more than about 3 centimeters of tissue (a little more than one and an eighth inch), PDT is mainly used to treat tumors on or just under the skin or on the lining of internal organs. Photodynamic therapy makes the skin and eyes sensitive to light for 6 weeks or more after treatment. Patients are advised to avoid direct sunlight and bright indoor light for at least 6 weeks. If patients must go outdoors, they need to wear protective clothing, including sunglasses. Other temporary side effects of PDT are related to the treatment of specific areas and can include coughing, trouble swallowing, abdominal pain, and painful breathing or shortness of breath. In December 1995, the U.S. Food and Drug Administration (FDA) approved a photosensitizing agent called porfimer sodium, or Photofrin®, to relieve symptoms of esophageal cancer that is causing an obstruction and for esophageal cancer that cannot be satisfactorily treated with lasers alone. In January 1998, the FDA approved porfimer sodium for the treatment of early nonsmall cell lung cancer in patients for whom the usual treatments for lung cancer are not appropriate. The National Cancer Institute and other institutions are supporting clinical trials (research studies) to evaluate the use of photodynamic therapy for several types of cancer, including cancers of the bladder, brain, larynx, and oral cavity.

In yet another embodiment, laser therapy is used to harness high-intensity light to destroy cancer cells. This technique is often used to relieve symptoms of cancer such as bleeding or obstruction, especially when the cancer cannot be cured by other treatments. It may also be used to treat cancer by shrinking or destroying tumors. The term "laser" stands for light amplification by stimulated emission of radiation. Ordinary light, such as that from a light bulb, has many wavelengths and spreads in all directions. Laser light, on the other hand, has a specific wavelength and is focused in a narrow beam. This type of high-intensity light contains a lot of energy. Lasers are very powerful and may be used to cut through steel or to shape diamonds. Lasers also can be used for very precise surgical work, such as repairing a damaged retina in the eye or cutting through tissue (in place of a scalpel). Although there are several different kinds of lasers, only three kinds have gained wide use in medicine: Carbon dioxide ($CO_2$) laser—This type of laser can remove thin layers from the skin's surface without penetrating the deeper layers. This technique is particularly useful in treating tumors that have not spread deep into the skin and certain precancerous conditions. As an alternative to traditional scalpel surgery, the $CO_2$ laser is also able to cut the skin. The laser is used in this way to remove skin cancers. Neodymium:yttrium-aluminum-garnet (Nd:YAG) laser—Light from this laser can penetrate deeper into tissue than light from the other types of lasers, and it can cause blood to clot quickly. It can be carried through optical fibers to less accessible parts of the body. This type of laser is sometimes used to treat throat cancers. Argon laser—This laser can pass through only superficial layers of tissue and is therefore useful in dermatology and in eye surgery. It also is used with light-sensitive dyes to treat tumors in a procedure known as photodynamic therapy (PDT). Lasers have several advantages over standard surgical tools, including: Lasers are more precise than scalpels. Tissue near an incision is protected, since there is little contact with surrounding skin or other tissue. The heat produced by lasers sterilizes the surgery site, thus reducing the risk of infection. Less operating time may be needed because the precision of the laser allows for a smaller incision. Healing time is often shortened; since laser heat seals blood vessels, there is less bleeding, swelling, or scarring. Laser surgery may be less complicated. For example, with fiber optics, laser light can be directed to parts of the body without making a large incision. More procedures may be done on an outpatient basis. Lasers can be used in two ways to treat cancer: by shrinking or destroying a tumor with heat, or by activating a chemical—known as a photosensitizing agent—that destroys cancer cells. In PDT, a photosensitizing agent is retained in cancer cells and can be stimulated by light to cause a reaction that kills cancer cells. $CO_2$ and Nd:YAG lasers are used to shrink or destroy tumors. They may be used with endoscopes, tubes that allow physicians to see into certain areas of the body, such as the bladder. The light from some lasers can be transmitted through a flexible endoscope fitted with fiber optics. This allows physicians to see and work in parts of the body that could not otherwise be reached except by surgery and therefore allows very precise aiming of the laser beam. Lasers also may be used with low-power microscopes, giving the doctor a clear view of the site being treated. Used with other instruments, laser systems can produce a cutting area as small as 200 microns in diameter—less than the width of a very fine thread. Lasers are used to treat many types of cancer. Laser surgery is a standard treatment for certain stages of glottis (vocal cord), cervical, skin, lung, vaginal, vulvar, and penile cancers. In addition to its use to destroy the cancer, laser surgery is also used to help relieve symptoms caused by cancer (palliative care). For example, lasers may be used to shrink or destroy a tumor that is blocking a patient's trachea (windpipe), making it easier to breathe. It is also sometimes used for palliation in colorectal and anal cancer. Laser-induced interstitial thermotherapy (LITT) is one of the most recent developments in laser therapy. LITT uses the same idea as a cancer treatment called hyperthermia; that heat may help shrink tumors by damaging cells or depriving them of substances they need to live. In this treatment, lasers are directed to interstitial areas (areas between organs) in the body. The laser light then raises the temperature of the tumor, which damages or destroys cancer cells.

The duration and/or dose of treatment with anti-immune checkpoint therapies may vary according to the particular anti-immune checkpoint agent or combination thereof. An appropriate treatment time for a particular cancer therapeutic agent will be appreciated by the skilled artisan. The present invention contemplates the continued assessment of optimal treatment schedules for each cancer therapeutic agent, where the phenotype of the cancer of the subject as determined by the methods encompassed by the present invention is a factor in determining optimal treatment doses and schedules.

Any means for the introduction of a polynucleotide into mammals, human or non-human, or cells thereof may be adapted to the practice of aspects and embodiments encompassed by the present invention for the delivery of the various constructs encompassed by the present invention into the intended recipient. In one embodiment encompassed by the present invention, the DNA constructs are delivered to cells by transfection, i.e., by delivery of "naked" DNA or in a complex with a colloidal dispersion system. A colloidal system includes macromolecule complexes, nanocapsules, microspheres, beads, and lipid-based systems including oil-in-water emulsions, micelles, mixed micelles, and liposomes. The preferred colloidal system encompassed by the present invention is a lipid-complexed or liposome-formulated DNA. In the former approach, prior to formulation of DNA, e.g., with lipid, a plasmid containing a transgene bearing the desired DNA constructs may first be experimentally optimized for expression (e.g., inclusion of an intron in the 5' untranslated region and elimination of unnecessary sequences (Felgner, et al., Ann NY Acad Sci 126-139, 1995). Formulation of DNA, e.g. with various lipid or liposome materials, may then be effected using known methods and materials and delivered to the recipient mammal. See, e.g., Canonico et al, Am J Respir Cell Mol Biol 10:24-29, 1994; Tsan et al, Am J Physiol 268; Alton et al., Nat Genet. 5:135-142, 1993 and U.S. Pat. No. 5,679,647 by Carson et al.

The targeting of liposomes can be classified based on anatomical and mechanistic factors. Anatomical classification is based on the level of selectivity, for example, organ-specific, cell-specific, and organelle-specific. Mechanistic targeting can be distinguished based upon whether it is passive or active. Passive targeting utilizes the natural tendency of liposomes to distribute to cells of the reticulo-endothelial system (RES) in organs, which contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

The surface of the targeted delivery system may be modified in a variety of ways. In the case of a liposomal targeted delivery system, lipid groups can be incorporated into the lipid bilayer of the liposome in order to maintain the targeting ligand in stable association with the liposomal bilayer. Various linking groups can be used for joining the lipid chains to the targeting ligand. Naked DNA or DNA associated with a delivery vehicle, e.g., liposomes, can be administered to several sites in a subject (see below).

Nucleic acids can be delivered in any desired vector. These include viral or non-viral vectors, including adenovirus vectors, adeno-associated virus vectors, retrovirus vectors, lentivirus vectors, and plasmid vectors. Exemplary types of viruses include HSV (herpes simplex virus), AAV (adeno associated virus), HIV (human immunodeficiency virus), BIV (bovine immunodeficiency virus), and MLV (murine leukemia virus). Nucleic acids can be administered in any desired format that provides sufficiently efficient delivery levels, including in virus particles, in liposomes, in nanoparticles, and complexed to polymers.

The nucleic acids encoding a protein or nucleic acid of interest may be in a plasmid or viral vector, or other vector as is known in the art. Such vectors are well known and any can be selected for a particular application. In one embodiment encompassed by the present invention, the gene delivery vehicle comprises a promoter and a demethylase coding sequence. Preferred promoters are tissue-specific promoters and promoters which are activated by cellular proliferation, such as the thymidine kinase and thymidylate synthase promoters. Other preferred promoters include promoters which are activatable by infection with a virus, such as the α- and β-interferon promoters, and promoters which are activatable by a hormone, such as estrogen. Other promoters which can be used include the Moloney virus LTR, the CMV promoter, and the mouse albumin promoter. A promoter may be constitutive or inducible.

In another embodiment, naked polynucleotide molecules are used as gene delivery vehicles, as described in WO 90/11092 and U.S. Pat. No. 5,580,859. Such gene delivery vehicles can be either growth factor DNA or RNA and, in certain embodiments, are linked to killed adenovirus. Curiel et al., Hum. Gene. Ther. 3:147-154, 1992. Other vehicles which can optionally be used include DNA-ligand (Wu et al., J. Biol. Chem. 264:16985-16987, 1989), lipid-DNA combinations (Felgner et al., Proc. Natl. Acad. Sci. USA 84:7413 7417, 1989), liposomes (Wang et al., Proc. Natl. Acad. Sci. 84:7851-7855, 1987) and microprojectiles (Williams et al., Proc. Natl. Acad. Sci. 88:2726-2730, 1991).

A gene delivery vehicle can optionally comprise viral sequences such as a viral origin of replication or packaging signal. These viral sequences can be selected from viruses such as astrovirus, coronavirus, orthomyxovirus, papovavirus, paramyxovirus, parvovirus, picornavirus, poxvirus, retrovirus, togavirus or adenovirus. In a preferred embodiment, the growth factor gene delivery vehicle is a recombinant retroviral vector. Recombinant retroviruses and various uses thereof have been described in numerous references including, for example, Mann et al., Cell 33:153, 1983, Cane and Mulligan, Proc. Nat'l. Acad. Sci. USA 81:6349, 1984, Miller et al., Human Gene Therapy 1:5-14, 1990, U.S. Pat. Nos. 4,405,712, 4,861,719, and 4,980,289, and PCT Application Nos. WO 89/02,468, WO 89/05,349, and WO 90/02,806. Numerous retroviral gene delivery vehicles can be utilized in the present invention, including for example those described in EP 0,415,731; WO 90/07936; WO 94/03622; WO 93/25698; WO 93/25234; U.S. Pat. No. 5,219,740; WO 9311230; WO 9310218; Vile and Hart, Cancer Res. 53:3860-3864, 1993; Vile and Hart, Cancer Res. 53:962-967, 1993; Ram et al., Cancer Res. 53:83-88, 1993; Takamiya et al., J. Neurosci. Res. 33:493-503, 1992; Baba et al., J. Neurosurg. 79:729-735, 1993 (U.S. Pat. No. 4,777,127, GB 2,200,651, EP 0,345,242 and WO91/02805).

Other viral vector systems that can be used to deliver a polynucleotide encompassed by the present invention have been derived from herpes virus, e.g., Herpes Simplex Virus (U.S. Pat. No. 5,631,236 by Woo et al., issued May 20, 1997 and WO 00/08191 by Neurovex), vaccinia virus (Ridgeway (1988) Ridgeway, "Mammalian expression vectors," In: Rodriguez R L, Denhardt D T, ed. Vectors: A survey of molecular cloning vectors and their uses. Stoneham: Butterworth; Baichwal and Sugden (1986) "Vectors for gene transfer derived from animal DNA viruses: Transient and stable expression of transferred genes," In: Kucherlapati R, ed. Gene transfer. New York: Plenum Press; Coupar et al. (1988) Gene, 68:1-10), and several RNA viruses. Preferred viruses include an alphavirus, a poxivirus, an arena virus, a vaccinia virus, a polio virus, and the like. They offer several attractive features for various mammalian cells (Friedmann (1989) Science, 244:1275-1281; Ridgeway, 1988, supra; Baichwal and Sugden, 1986, supra; Coupar et al., 1988; Horwich et al. (1990) J. Virol., 64:642-650).

In other embodiments, target DNA in the genome can be manipulated using well-known methods in the art. For example, the target DNA in the genome can be manipulated by deletion, insertion, and/or mutation are retroviral insertion, artificial chromosome techniques, gene insertion, random insertion with tissue specific promoters, gene targeting, transposable elements and/or any other method for introducing foreign DNA or producing modified DNA/modified nuclear DNA. Other modification techniques include deleting DNA sequences from a genome and/or altering nuclear DNA sequences. Nuclear DNA sequences, for example, may be altered by site-directed mutagenesis.

IV. Clinical Efficacy

Clinical efficacy can be measured by any method known in the art. For example, the response to a therapy, such as anti-immune checkpoint therapies, relates to any response of the cancer, e.g., a tumor, to the therapy, preferably to a change in tumor mass and/or volume after initiation of neoadjuvant or adjuvant chemotherapy. Tumor response may be assessed in a neoadjuvant or adjuvant situation where the size of a tumor after systemic intervention can be compared to the initial size and dimensions as measured by CT, PET, mammogram, ultrasound or palpation and the cellularity of a tumor can be estimated histologically and compared to the cellularity of a tumor biopsy taken before initiation of treatment. Response may also be assessed by caliper measurement or pathological examination of the tumor after biopsy or surgical resection. Response may be recorded in a quantitative fashion like percentage change in tumor volume or cellularity or using a semi-quantitative scoring system such as residual cancer burden (Symmans et al., *J. Clin. Oncol.* (2007) 25:4414-4422) or Miller-Payne score (Ogston et al., (2003) *Breast* (Edinburgh, Scotland) 12:320-327) in a qualitative fashion like "pathological complete response" (pCR), "clinical complete remission" (cCR), "clinical partial remission" (cPR), "clinical stable disease" (cSD), "clinical progressive disease" (cPD) or other qualitative criteria.

Assessment of tumor response may be performed early after the onset of neoadjuvant or adjuvant therapy, e.g., after a few hours, days, weeks or preferably after a few months. A typical endpoint for response assessment is upon termination of neoadjuvant chemotherapy or upon surgical removal of residual tumor cells and/or the tumor bed.

In some embodiments, clinical efficacy of the therapeutic treatments described herein may be determined by measuring the clinical benefit rate (CBR). The clinical benefit rate is measured by determining the sum of the percentage of patients who are in complete remission (CR), the number of patients who are in partial remission (PR) and the number of patients having stable disease (SD) at a time point at least 6 months out from the end of therapy. The shorthand for this formula is CBR=CR+PR+SD over 6 months. In some embodiments, the CBR for a particular anti-immune checkpoint therapeutic regimen is at least 25%, 30%, 35%, 40%, 45%, 50%, 55%, 60%, 65%, 70%, 75%, 80%, 85%, or more.

Additional criteria for evaluating the response to anti-immune checkpoint therapies are related to "survival," which includes all of the following: survival until mortality, also known as overall survival (wherein said mortality may be either irrespective of cause or tumor related); "recurrence-free survival" (wherein the term recurrence shall include both localized and distant recurrence); metastasis free survival; disease free survival (wherein the term disease shall include cancer and diseases associated therewith). The length of said survival may be calculated by reference to a defined start point (e.g., time of diagnosis or start of treatment) and end point (e.g., death, recurrence or metastasis). In addition, criteria for efficacy of treatment can be expanded to include response to chemotherapy, probability of survival, probability of metastasis within a given time period, and probability of tumor recurrence.

For example, in order to determine appropriate threshold values, a particular anti-immune checkpoint therapeutic regimen can be administered to a population of subjects and the outcome can be correlated to measurements that were determined prior to administration of any immune checkpoint therapy. The outcome measurement may be pathologic response to therapy given in the neoadjuvant setting. Alternatively, outcome measures, such as overall survival and disease-free survival can be monitored over a period of time for subjects following immune checkpoint therapy for whom measurement values are known. In certain embodiments, the same doses of anti-immune checkpoint agents are administered to each subject. In related embodiments, the doses administered are standard doses known in the art for anti-immune checkpoint agents. The period of time for which subjects are monitored can vary. For example, subjects may be monitored for at least 2, 4, 6, 8, 10, 12, 14, 16, 18, 20, 25, 30, 35, 40, 45, 50, 55, or 60 months. Measurement threshold values that correlate to outcome of an immune checkpoint therapy can be determined using methods such as those described in the Examples section.

V. Further Uses and Methods Encompassed by the Present Invention

The methods described herein can be used in a variety of therapeutic applications. In any method described herein, such as a diagnostic method, prognostic method, therapeutic method, or combination thereof, all steps of the method can be performed by a single actor or, alternatively, by more than one actor. For example, diagnosis can be performed directly by the actor providing therapeutic treatment. Alternatively, a person providing a therapeutic agent can request that a diagnostic assay be performed. The diagnostician and/or the therapeutic interventionist can interpret the diagnostic assay results to determine a therapeutic strategy. Similarly, such alternative processes can apply to other assays, such as prognostic assays. Moreover, any method of diagnosis, prognosis, prevention, and the like described herein can be applied to a therapy or test agent of interest, such as immune checkpoint therapies, anti-adenosine therapies, anti-cancer therapies, and the like.

The compositions described herein (including dual binding antibodies and derivatives and conjugates thereof) can be used in a variety of in vitro and in vivo therapeutic applications using the formulations and/or combinations described herein. In one embodiment, anti-immune checkpoint agents can be used to treat cancers determined to be responsive thereto. For example, antibodies that block the interaction between PD-L1, PD-L2, and/or CTLA-4 and their receptors (e.g., PD-L1 binding to PD-1, PD-L2 binding to PD-1, and the like) can be used to treat cancer in subjects identified as likely responding thereto.

VI. Kits

The present invention also encompasses kits. A kit encompassed by the present invention may also include instructional materials disclosing or describing the use of the kit or an antibody of the disclosed invention in a method of the disclosed invention as provided herein. A kit may also include additional components to facilitate the particular application for which the kit is designed. For example, a kit may additionally contain means of detecting the label (e.g., enzyme substrates for enzymatic labels, filter sets to detect fluorescent labels, appropriate secondary labels such as a sheep anti-mouse-HRP, etc.) and reagents necessary for controls (e.g., control biological samples or standards). A kit may additionally include buffers and other reagents recognized for use in a method of the disclosed invention. Non-limiting examples include agents to reduce non-specific binding, such as a carrier protein or a detergent.

EXEMPLIFICATION

This invention is further illustrated by the following examples, which should not be construed as limiting.

Example 1: Leukemia Vaccine Overcomes Limitations of Checkpoint Blockade by Evoking Clonal T Cell Responses in a Murine AML Model A personalized vaccine was developed whereby patient derived leukemia cells are fused to autologous dendritic cells, evoking a polyclonal T cell response against shared and neo-antigens. It was postulated that the dendritic cell (DC)/AML, fusion vaccine would demonstrate synergy with checkpoint blockade by expanding tumor antigen specific lymphocytes that would provide a critical substrate for checkpoint blockade mediated activation.

Using an immunocompetent murine leukemia model, we examined the immunologic response and therapeutic efficacy of vaccination in conjunction with checkpoint blockade with respect to leukemia engraftment, disease burden, survival and the induction of tumor specific immunity.

Mice treated with checkpoint blockade alone had rapid leukemia progression and demonstrated only a modest extension of survival. Vaccination with DC/AML fusions resulted in the expansion of tumor specific lymphocytes and disease eradication in a subset of animals, while the combination of vaccination and checkpoint blockade induced a fully protective tumor specific immune response in all treated animals. Vaccination followed by checkpoint blockade resulted in upregulation of genes regulating activation and proliferation in memory and effector T cells. Long term survivors exhibited increased T cell clonal diversity and were resistant to subsequent tumor challenge.

The combined DC/AML fusion vaccine and checkpoint blockade treatment offers unique synergy inducing the durable activation of leukemia specific immunity, protection from lethal tumor challenge and the selective expansion of tumor reactive clones.

Introduction

While acute myeloid leukemia (AML) often demonstrates initial sensitivity to cytotoxic therapy, responses are typically transient due to the presence of clonal populations with intrinsic chemotherapy resistance[1]. In contrast, the potency of cell-based immunotherapy for patients with AML is supported by the observation that allogeneic transplantation is uniquely curative for a subset of patients mediated by alloreactive lymphocytes 2. However, therapeutic efficacy is limited by associated toxicity of graft versus host disease arising from the lack of specificity of the immune response[3]. A major area of investigation is the development of immunotherapeutic strategies to more selectively induce disease regression while providing durable protection from relapse through the establishment of memory responses.

We have developed a personalized tumor vaccine in which patient derived tumor cells are fused with autologous dendritic cells (DCs) such that a broad array of tumor derived antigens including neoantigens is presented in the context of DC-mediated co-stimulation effectively capturing tumor heterogeneity[4,5]. In a phase I/II clinical trial, vaccination of AML patients who achieved chemotherapy induced remission induced the durable expansion of leukemia specific T cells in the peripheral blood and bone marrow. Remarkably, despite a median age of 63, 71% of vaccinated patients remained in remission at a median of 5 years of follow up[6]. These results were in stark contrast to historical data suggesting a 3-year progression free survival of 10-15% in this age population[7].

A potential challenge for therapeutic efficacy of active vaccination is the dysfunction of the T cell repertoire characterized by upregulation of pathways that promote exhaustion and senescence, particularly in the microenvironment of advanced disease[4]. A transformative advance in the field of immunotherapy is the finding that therapeutic blockade of the PD-1/PD-L1 negative costimulatory pathway has resulted in dramatic disease response in a subset of solid tumors such as melanoma, characterized by a high mutational burden and the presence of neoantigens and an associated intrinsic T cell response[5]. In contrast, checkpoint blockade has exhibited minimal therapeutic efficacy for patients with hematological malignancies such as AML[6], potentially due to the relative low mutational burden and lack of a significant population of tumor reactive lymphocytes within the tumor microenvironment.

We postulated that combination of vaccine and checkpoint inhibitor therapy would demonstrate unique synergy in which vaccination would provide functionally competent leukemia specific T cell populations while the introduction of checkpoint blockade would enhance their effectiveness and persistence. Because an exhausted T cell phenotype can be due to several immunoinhibitory signals working in concert[7], we hypothesize simultaneous checkpoint blockade may be advantageous.

In the present study in an aggressive immunocompetent murine leukemia model, we interrogated the immunologic response and therapeutic efficacy of fusion cell vaccination in conjunction with blockade of negative costimulatory pathways using antibodies targeting PD-1 and TIM-3, critical mediators of the immune suppressive milieu of the bone marrow[8-10]. We also targeted Repulsive Guidance Molecule b (RGMb), a co-receptor for bone morphogenetic proteins which play a role in maintenance of hematopoietic progenitors including support for AML cells in the marrow niche[11,12] and also may mediate immune tolerance via binding to PD-L2 on myeloid cells[17].

We demonstrated that the combination of DC/AML vaccine and checkpoint blockade was uniquely effective in preventing disease progression and inducing a memory response as manifested by protection from tumor re-challenge. Vaccination followed by checkpoint blockade resulted in upregulation of genes regulating activation and proliferation of memory and effector T cells as well as enhanced T cell clonal diversity.

Materials and Methods

Cell Lines: The murine AML cell line TIB-49 was purchased from ATCC. Cells were tested for *Mycoplasma* contamination (Myco-Alert *Mycoplasma* Detection Kit, LT07-318, Lonza). For all experiments, cell lines were transduced with luciferase/Mcherry using a lentiviral vector (pCDH-EF-eFFLy-T2A-mCherry) kindly provided by Prof. Irmela Jeremias from Helmholtz Zentrum München, Germany and then sorted to obtain a greater than 99% positive population. Cells were cultured at 37° C. in a humidified 5% $CO_2$ incubator in RPMI 1640 media (Cellgro, Manassas, VA) supplemented with heat-inactivated 10% fetal bovine serum (Atlanta Biologicals, Flower Branch, GA), 100 IU/ml penicillin, and 100 μg/ml streptomycin (Cellgro).

Flow cytometry: Cells were analyzed for mCherry, CD62L, CD44, CD4, CD8, CD86 and CD25 expression by multichannel flow cytometry. Cells were incubated with FcR blocking reagent (Miltenyi, Bergisch Gladbach, Germany) for 10 min at room temperature followed by anti-CD62L APC (BD Pharmingen), anti-44-PE (BD Pharmingen), anti-CD4-BV (BioLegend, San Diego, CA), anti-CD8-APC-cy7 (BioLegend, San Diego, CA) or appropriate isotype control. Analysis was performed using FACS Aria (BD Biosciences, San Jose, CA) and Kaluza software (Beckman Coulter, Brea, CA).

For intracellular IFN-γ expression, T cells were pulsed with GolgiStop (1 μg/ml; BD Pharmingen) for 4-6 h at 37° C. then labeled with CD4-BV and CD8-APC-Cy7. Permeabilization with Cytofix/Cytoperm (BD Pharmingen) containing formaldehyde and saponin was performed for 30 min at 4° C. Cells were washed twice in Perm/Wash solution and incubated with PE-conjugated IFN-γ (Invitrogen, Camarillo, CA) or a matched isotype control for 30 min. Cells were washed in 1× Perm/Wash solution prior to analysis.

Murine survivin expression in TIB-49 cells was assessed using intracellular flow cytometric analysis using survivin (60.11) [Alexa Fluor® 647] mAbs (Novus, USA). Alexa Fluor® 647 Mouse IgG2a, κ was used as isotype control.

Vaccination with DC/AML fusions and/or treatment with checkpoint inhibitors in vivo: Murine syngeneic DC/AML fusion cells were generated as previously described[13].

Briefly D Cs were generated from bone marrow mononuclear cells harvested from the femurs of C57BL/6J mice cultured in the presence of IL-4 and GM-CSF for 5-7 days. DCs were fused with TIB-49 mCherry AML cells in the presence of PEG and exposed to 30Gy gamma irradiation. DC/AML fusion cells were quantified by determining the percentage of cells with co-expression of DC (anti-CD86-Alexa-647) and tumor (Mcherry) markers by flow cytometric analysis. C57BL/6J mice were inoculated retro-orbitally with $5\times10^4$ luciferase/mcherry TIB-49 murine leukemia cells (1mTIB). Cohorts of mice were assigned to treatment with $100\times10^3$ DC/TIB-49 fusion cells via subcutaneous injection 24 hours after AML challenge; intraperitoneally with 200 μg each of rat anti-mouse PD-1 (29F.1A10); mouse anti-mouse TIM3 (T3A.1A10); rat anti-mouse RGMb (307.9D1) or all three mAbs starting 4 days after AML challenge and continued every 3 days for 6 doses; or the combination of DC/AML fusion vaccine and mAbs treatment.

Assessment of Leukemia-specific immunity: Leukemia specific immunity was assessed in peripheral blood of a subset of cohorts of animals inoculated with TIB-49 cells and then treated with DC/AML vaccine, anti-PD 1/anti-TIM 3/anti-RGMb checkpoint inhibitors, or the combination of both. On day 14 following tumor challenge, peripheral blood T cells were isolated, exposed to syngeneic TIB-49 tumor lysate for 3 days, and expression of intracellular IFN-γ expression was quantified by intracellular flow cytometric analysis as a measure of leukemia specific recognition. Similar analysis was perfumed using spleen derived T cells harvested from euthanized animals 17 days after tumor challenge and following treatment as described above.

To assess antigen specific anti-tumor immunity the spleenocytes underwent flowcytometric analysis using H-2 db pentamers. Cells were stained with anti-CD8APC-Cy7 and murine survivin specific APC-conjugated pentamers ATFKNWPFL (ProImmune, Inc; Sarasota, FL, USA). CMV specific PE—conjugated pentamers HGIRNASFI (ProImmune, Inc; Sarasota, FL, USA) were used as control. Percent of pentamer positive CD8 T cells was assessed using multichannel flow cytometry.

Bioluminescent imaging: BLI was performed using a Xenogen IVIS-50™ camera and analyzed with Living Image software (Caliper LifeSciences).

TCR diversity analysis: Targeted T CR diversity analysis was interrogated using SMARTer human α/β profiling kit (Takara, CA, USA). Initially total RNA was extracted and purified from mouse blood using RNeasy mini kit (Qiagen, Germantown, MD). RNA quality was assessed using the RNA pico chip (Agilent 2100 bioanalyzer). Targeted T CR libraries were prepared from the high-quality RNA using the 5'-SMART (Switching Mechanism At the 5' end of RNA Template) approach. The TCR library quality was verified using HS DNA chips (Agilent 2100 Bioanalyzer). The high quality TCR libraries were sequenced on Illumina MiSeq Sequencer using the 600-cycle MiSeq Reagent kit v3 (Illumina, San Diego, CA) with paired end (2×300 base pair reads).

The sequencing data was checked for quality control to remove low quality reads and aligned against TCR sequences from GenBank and IMGT database[19] using MiXCR software[20]. The aligned reads were assembled into TCR clones and their frequency or abundance was estimated. After normalization, the assembled clonotypes were analyzed to determine overall diversity of each sample using Inverse Simpson index and rarefaction analysis. The diversity patterns of samples (i.e., Control, vaccine, and vaccine+checkpoint point inhibitors) were compared to gauge the overall variation in TCR repertoire that is associated with different groups. Comparative analysis between the treatment groups also involved identification of dominant clones and specific tracking analysis to identify TCR clones that are stimulated by vaccine treatment and further enhanced or maintained by combined vaccine and checkpoint-based therapy.

Single Cell RNA Sequencing: scRNA-Seq was performed on peripheral blood mononuclear cells isolated from control or cohorts treated with the DC/AML fusion vaccine, or vaccine+checkpoint point inhibitors. 10X Genomics chromium system was employed for capturing single cells in the context of uniquely barcoded primer beads together in tiny droplets enabling large-scale parallel single-cell transcriptome studies. The single cell suspensions were generated using a 10X Chromium Controller Instrument[21]. The libraries were prepared using the Chromium single cell 3' GEM, library and gel bead kit V3 (10X Genomics, Pleasanton, CA) and sequencing was performed using the massively parallel sequencing NextSeq 500 platform. Approximately 30,000-40,000 reads per cell were performed capturing the expression of approximately 500-1,000 transcripts.

Analysis for single cell RNA sequencing data: RNA sequencing data was analyzed using standard statistical algorithms after quality control filtering, alignment to the reference genome (mm10) to generate raw counts for transcripts from each cell type. The data was preprocessed by removing the outlier cells with very low or high number of features (i.e. <200 & >2500 transcripts) or high UMI mapping to mitochondrial genes (i.e. >15%). Genes that were detected in less than three cells were removed. The preprocessed raw count data was log normalized using Seurat R package (version 3.0) for unsupervised and supervised analysis[23]. The scRNA-Seq samples from control, vaccine and combo groups were merged using Find Integration Anchors and integration functions in Seurat to generate an integrated matrix of normalized data[14]. Normalized and preprocessed data was subjected to unsupervised analysis using PCA to identify the principal components with significant variation applied for uniform manifold approximation projection (UMAP) analysis to determine overall relationship among cells[23]. Transcriptome profiles were clustered and annotated to different cell types including T cells (CD3+), B cells (CD19+, CD79+) and other immune cells based on expression of specific transcripts. Comparative analysis of the various cell types or subtypes in each cluster from control, vaccine and combination vaccine and checkpoint blockade cohorts. The distribution of various cell specific marker transcriptome profile was determined using feature plot function in the Seurat R package[24]. The significance of the differentially expressed transcripts was determined using t-stats ($P<0.05$) and fold change (≥1.2).

Pathway, Functions and Systems Biology Analysis: Pathways, functions and systems biology analysis was performed using the Ingenuity Pathway Analysis software package (IPA 9.0) (Qiagen-detailed description available at http//www.ingenuity.com). The significance of effect on pathways and functional categories was determined using one-tailed Fisher's Exact test. The pathways, functions with a P value<0.01 were considered statistically significant. The pathways, and functions with positive Z-score≥2 and ≤−2 were considered significantly activated and inhibited respectively.

Results

Treatment with Checkpoint Inhibitors Alone Was Ineffective to Prevent Disease Progression.

The effect of checkpoint inhibition alone on AML engraftment, progression and survival was interrogated in an immunocompetent murine AML model using TIB-49 murine AML cell line. These leukemia cells originated spontaneously in a C57BL/6 mouse and grow aggressively in syngeneic models. As a means of monitoring disease burden, TIB-49 AML cells were genetically manipulated to express luciferase and mCherry (ImTIB-49) via lentiviral transduction and selection. C57BL/6J mice underwent retro-orbital inoculation with $50\times10^3$ ImTIB-49 AML. The mice were then treated with 6 doses of isotype control, anti-PD1, anti-TIM3, anti-RGMb or combination of all three mAbs starting three days post tumor challenge. The treatments doses were administered IP every three days. Animals were monitored for disease bulk by serial bioluminescence imaging (BLI) analysis and survival. Untreated animals rapidly developed AML with symptomatic disease requiring euthanasia. Treatment with single agent anti-PD1, anti-TIM3 or anti-RGMb did not affect AML progression as compared to isotope control, with all animals euthanized by day 53 after tumor challenge whereas the combination of the three mAbs modestly delayed the onset of demonstrable leukemia with mildly improved survival (FIG. 1A,B).

Checkpoint Inhibition in Combination with DC/AML Fusion Vaccine (FV) Leads to Prolonged Survival.

Figure 2:
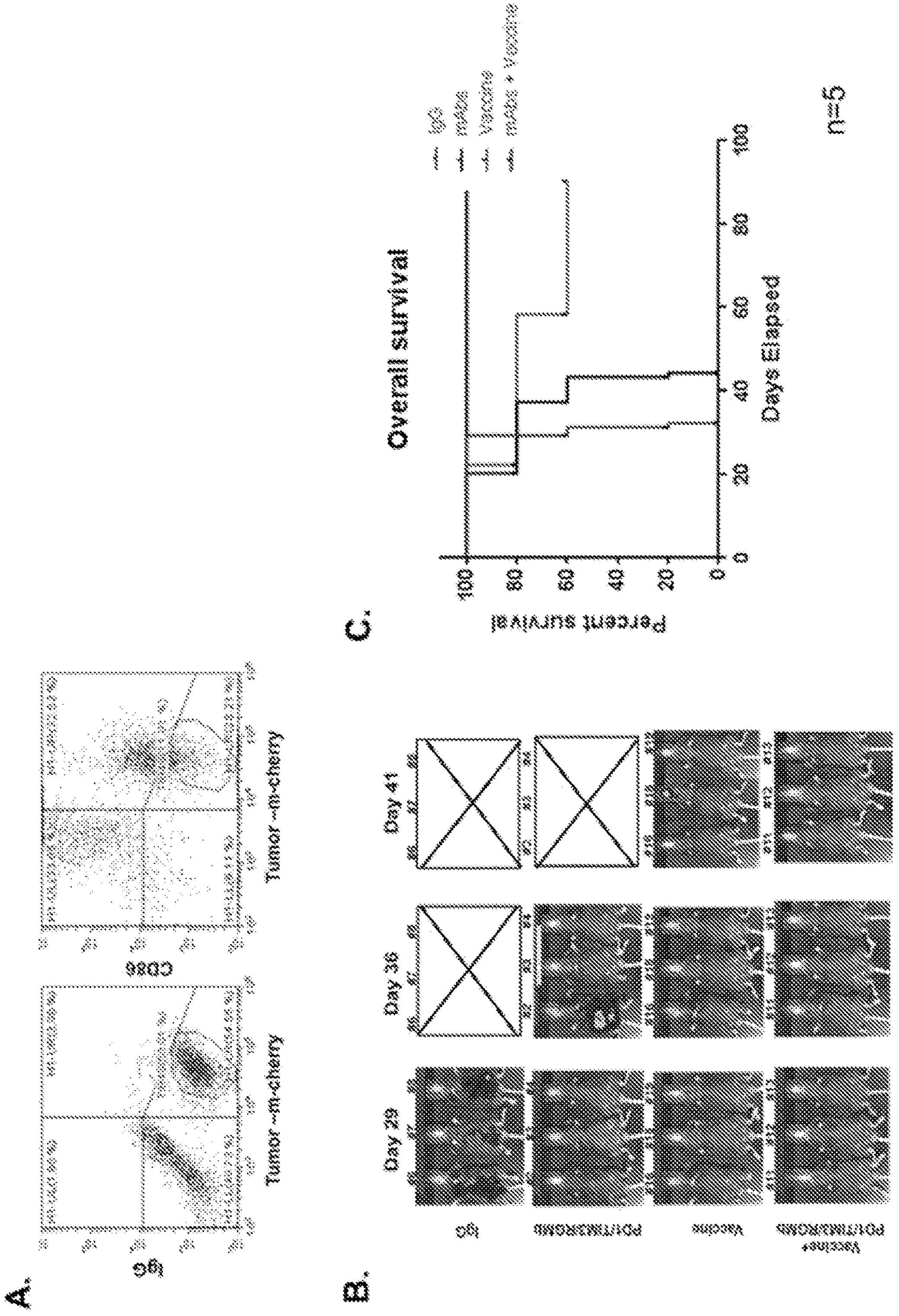
FIG. 2A-FIG. 2C shows that combination treatment with DC/AML fusion vaccine and PD1/TIM3/RGMb blockade prevents establishment of AML in-vivo. C57BL/6J mice were retro-orbitally inoculated with $50\times10^3$ syngeneic TIB-49 AML cells that were stably transduced with luciferase/m-cherry. (A) Syngeneic D C/AML fusion cells were generated as described and evaluated for co-expression of tumor (m-cherry) and DC (CD86) markers using flow cytometry. The mice were then treated with either vaccine alone, anti-PD1/TIM3/RGMb or combination of anti-PD1/TIM3/RGMb and the fusion vaccine. The mice were treated with appropriate isotype control as a negative control. (B) BLI imaging was performed serially starting Day 29 post inoculation (three representative mice are shown) and (C) the mice were followed for survival for 90 days as demonstrated in a Kaplan Meier curve (n=5).

We subsequently assessed the effect of checkpoint inhibition in conjunction with DC/AML fusion vaccination. Syngeneic D C/TIB-49 fusion cells were generated as described and confirmed to co-express both DC and tumor markers (FIG. 2A). C57BL/6J mice underwent retro-orbital inoculation with $50\times10^3$ lmTIB cells. 24 hours after tumor challenge, cohorts of mice were treated with a single dose of $100\times10^3$ syngeneic fusion cells, 6 doses of anti-PD1/TIM3/RGMb mAbs administered IP every 3 days, or the combination of the fusion vaccine and either isotype control or anti-PD1/TIM3/RGMb mAbs. Serial quantification of disease burden was assessed via BLI analysis beginning approximately 1 month after tumor challenge. All control mice demonstrated rapid evidence of AML engraftment, progressive disease by day 29 and required euthanasia by day 36 after initial tumor challenge (FIG. 2B). Mice treated with anti-PD1/TIM3/RGMb mAbs alone demonstrated a modest improvement in survival compared to control animals but all required euthanasia by day 44. Mice treated with the vaccine alone showed prevention of leukemic engraftment in a majority of animals with 2 of 5 mice remaining disease free at 90 days. Remarkably, the entire cohort of mice treated with vaccination and checkpoint blockade remained alive and disease free in this aggressive AML model 90 days post inoculation (FIG. 2C).

Checkpoint Inhibition in Conjunction with DC/AML Fusion Vaccine Leads to Increase in Tumor Specific Immunity.

Figure 3:
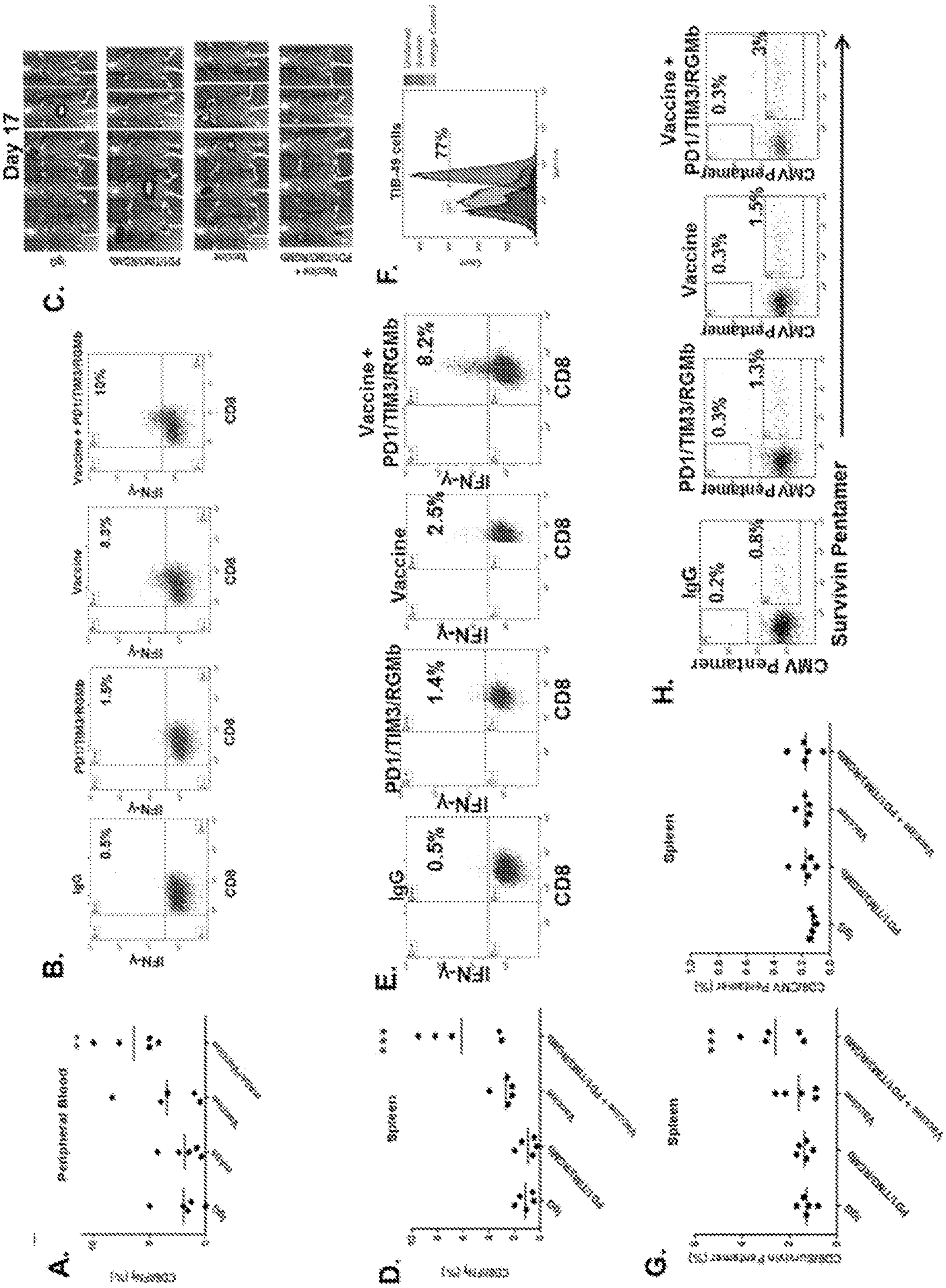
FIG. 3A-FIG. 3H show an increase in tumor specific T cells following combination treatment with fusion vaccine and PD1/TIM3/RGMb blockade. C57BL/6J mice were treated as described above. On day 14 peripheral blood (PB) was collected and CD8+ T cells were assessed for intracellular IFNγ expression using multichannel flow cytometry following exposure to autologous tumor lysate for three days. Results are presented as (A) summary of 5 analyzed mice (n=5; $p<0.05$) and (B) representative dot plots. (C) In a similar independent experiment on day 17 pot tumor challenge, the mice underwent BLI analysis. The mice were then euthanized; spleenocytes were harvested and assessed for IFNγ expression using multichannel flow cytometry following exposure to autologous tumor lysate. Results are presented as (D) summary of 5 analyzed mice (n=5; $p<0.05$) and (E) representative dot plots. Spleen derived CD8+ T cells were also assessed for frequency of tumor antigen specific T cells with multichannel flow cytometry using pentamer analysis. (F) TIB-49 AML cells were confirmed to express survivin using intracellular flow cytometric analysis, unstained cells and cells incubated with appropriate isotype control were used as negative control. Binding of APC labeled multimeric MI-IC/survivin peptide complexes to T cell receptors was examined to determine the frequency of the survivin specific T cells. Frequency of survivin specific T cells is presented in gated CD8+ T cells as a (G) summary of 5 analyzed mice (n=5; $p<0.05$) and (H) representative dot plots. Frequency of CMV specific T cells was analyzed as a control.

We subsequently examined whether the combination of vaccination with checkpoint inhibition would result in enhanced AML-specific immunity in-vivo. To measure tumor-specific T cell responses, peripheral blood (PB) cells were collected from mice 14 days after inoculation and tumor recognition was assessed in a modified EliSPOT in which the percent of CD8 T cells exhibiting intracellular IFN-γ expression following 3 days of stimulation with autologous TIB-49 tumor lysate was quantified. Mice treated with checkpoint inhibitors alone showed no expansion of T cells expressing IFN-γ following exposure to autologous tumor lysate as compared to control animals with mean percentages of 1.9% for both groups (n=5). Mice treated with the fusion vaccine showed variable expansion of tumor reactive T cells with mean levels IFN-γ expression of 3.4% (n=5; p=ns). This mean expansion did not meet statistical significance due to variability in tumor specific T cells in responding and non-responding animals. However, mice treated with both fusion vaccine (FV) and checkpoint inhibition showed a significant expansion of circulating tumor specific CD8+ Tcells with mean values of IFN-γ expressing cells of 6.4% (n=5; p=0.01) (FIG. 3A,B).

In a subsequent experiment, the enhanced expansion of tumor specific T cells following vaccination and checkpoint inhibition was confirmed in splenocytes populations in animals euthanized 17 days after tumor challenge. Consistent with our prior study, combinatorial therapy resulted in the most pronounced induction of tumor specific immunity associated with the prevention of leukemia engraftment in all of the treated animals (FIG. 3C,D,E).

To further elucidate the capacity of fusion cell vaccination and checkpoint blockade to elicit tumor specific immunity in-vivo, we quantified antigen specific T cells targeting survivin following treatment with check point inhibitor, vaccination or combination therapy. Survivin is a member of the Inhibitor of apoptosis (IAP) family, known to be overexpressed in AML. We demonstrated high levels of survivin expression by TIB-49 cells by intracellular flow cytometric analysis (FIG. 3F). Expansion of survivin specific T cells was quantified by MHC Class I pentamer analysis. Vaccination in combination with anti-PD1/TIM3/RGMb mAbs treatment resulted in a statistically significant 1.8 fold expansion of spleen derived T cells recognizing murine survivin in spleen CD8+ T cells compared to single agent treatment (FIG. 3G,H). Consistent with the tumor specificity of this response, vaccination and checkpoint inhibition did not result in increased frequency of CMV specific CD8+ T cells.

To assess whether combinatorial therapy with the fusion vaccine and checkpoint inhibition induces a memory response consistent with a durable protection, we next interrogated the T cell repertoire in the PB from surviving animals at day 36 after AML challenge. Combination treatment with FV and anti-PD1/TIM3/RGMb mAbs led to a statistically significant increase in CD4/CD44+/CD62L− memory T cells as compared to single agent treatments. Furthermore, a statistically significant decrease in CD4+ CD25+FOXP3+ Tregs was detected after combination treatment compared to the vaccine treatment group.

Treatment with DC/AML Fusion Vaccine and Checkpoint Inhibition is Protective Upon Re-Challenge with AML.

Having demonstrated that animals treated with the combination of vaccination and checkpoint blockade develop leukemia specific immunity with a memory phenotype and durable disease response, we subsequently assessed whether combination vaccine and checkpoint inhibitor therapy provided long-term protection from disease re-challenge.

Figure 4:
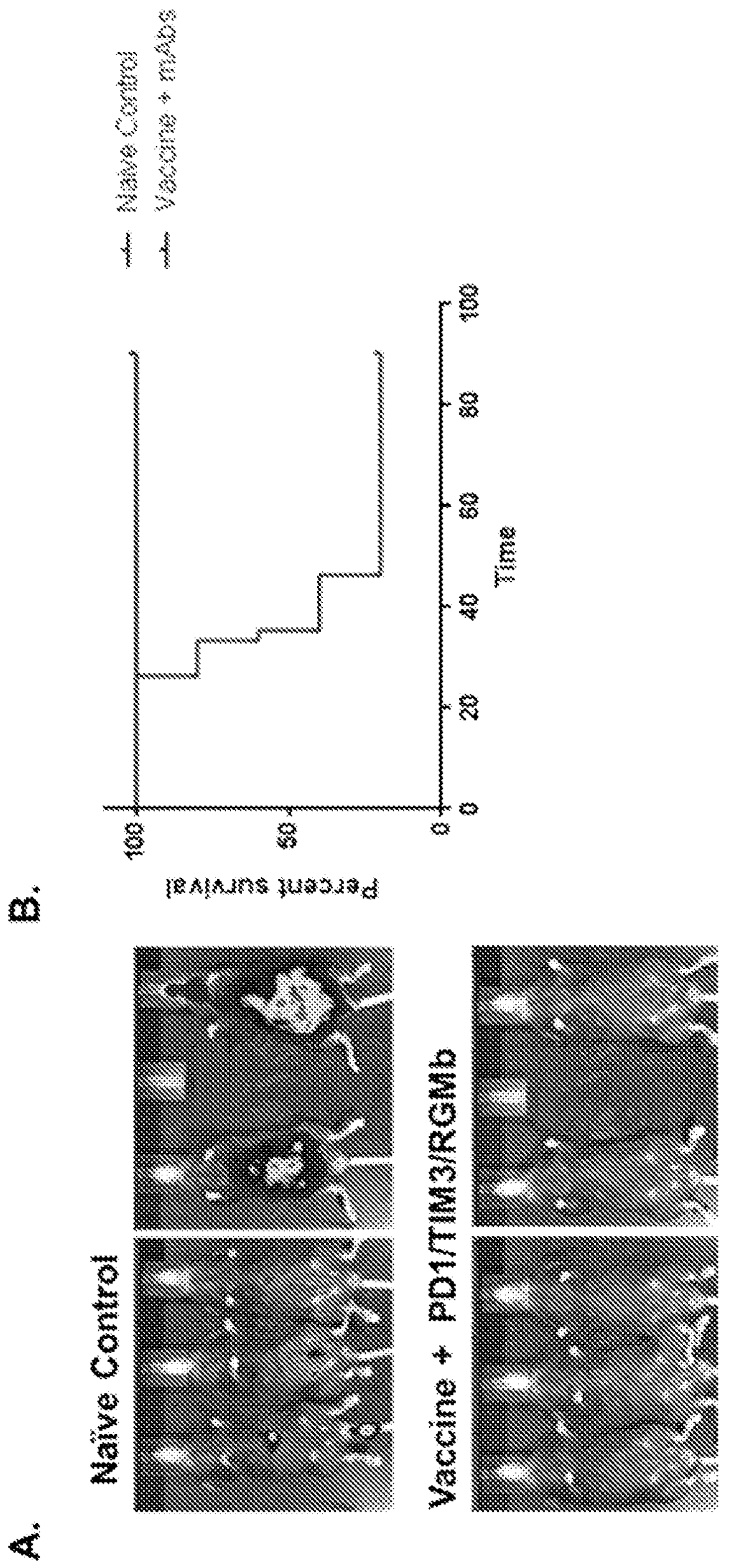
FIG. 4A and FIG. 4B show that treatment with DC/AML fusion vaccine in combination with PD1/TIM3/RGMb blockade prevents establishment of AML upon re-challenge with tumor cells. 90 days following the initial tumor challenge and treatment with six doses of anti-PD1/TIM3/RGMb, C57BL/6J mice were challenged with addition dose of 50,000 luciferase/mCherry transduced syngeneic TIB-49 cells. Naïve, age matched mice were inoculated with the same dose as control. For AML burden assessment, (A) BLI imaging was performed after re-challenge (B) the mice were followed for survival for 90 days as demonstrated in a Kaplan Meier curve (n=5).

Mice that had initially been challenged with tumor inoculation and rendered disease free from combined vaccine and checkpoint inhibitor therapy were subsequently re-challenged via retro-orbital inoculation with a lethal dose ($5\times10^3$) lmTIB at day 90. Age-matched naïve C57BL/6J control mice were challenged with $5\times10^3$ lmTIB as control. Mice were followed for survival and disease progression with BLI. In contrast to control animals, mice that were previously treated with the combination of vaccination and checkpoint inhibition were uniformly protected from disease and showed no evidence of leukemic engraftment (FIG. 4A,B).

Figure 5:
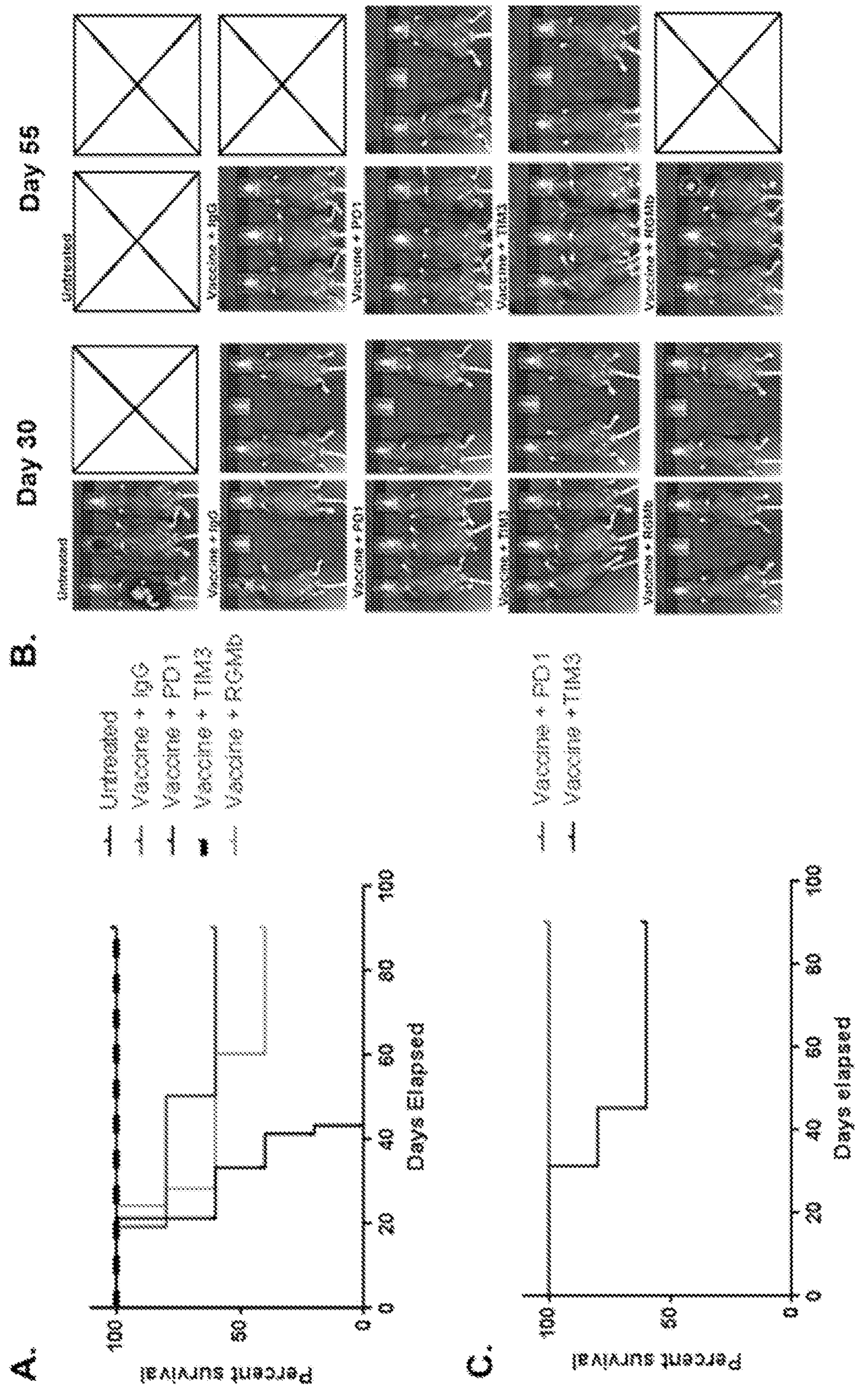
FIG. 5A-FIG. 5C show that combination treatment with DC/AML fusion vaccine and anti-PD1 or fusion vaccine and anti-TIM3 prevents establishment of AML in-vivo. C57BL/6J mice were retro-orbitally inoculated with $50\times10^3$ syngeneic TIB-49 AML cells that were stably transduced with luciferase/m-cherry. Syngeneic D C/AML fusion cells were generated as described. The mice were then treated with either vaccine alone, or with fusion vaccine in combination with anti-PD1; anti-TIM3 or anti-RGMb. Control mice were treated with the appropriate isotype control. For AML progression assessment, (A) BLI imaging was performed starting Day 30 post inoculation (B) the mice were followed for survival as demonstrated in a Kaplan Meier curve (n=5). At 90 days post initial tumor challenge, mice treated with vaccine+TIM3; and vaccine+PD1 were challenged with additional dose of $50\times10^3$ syngeneic TIB-49 AML. (C) The mice were followed for survival for additional 90 days as demonstrated in a Kaplan Meier curve (n=5)

We subsequently examined the relative contribution of each individual checkpoint inhibitor on vaccine efficacy. C57BL/6J mice were treated with syngeneic FV in combination with anti-PD-1, anti-TIM-3 or anti-RGMb MAbs as described above. At day post tumor challenge, 3 out of 5 mice treated with FV alone were free of disease, replicating our previous findings. The addition of anti-RGMb showed efficacy equivalent to FV alone, with 2 out of 5 animals surviving. However, vaccination in conjunction with PD-1 blockade or TIM-3 blockade alone resulted in 100% of animals surviving without evidence of disease (FIG. 5A,B).

Amongst these cohorts with complete treatment response, FV plus either anti-PD-1 (n=5) or anti-TIM-3 (n=5), mice were rechallenged with $50\times10^3$ lmTIB cells to evaluate long-term anti-leukemia immunity. Mice were followed for an additional 90 days, resulting in 5 of 5 mice remaining disease free in the FV plus PD-1 cohort post re-challenge while 2 of 5 mice in the TIM-3 cohort succumbed to disease (FIG. 5C).

Vaccination in Conjunction with PD-1 Blockade Leads to an Increase in Inflammatory Signaling Pathways and Blunts Apoptosis in Memory T Cells.

Figure 6:
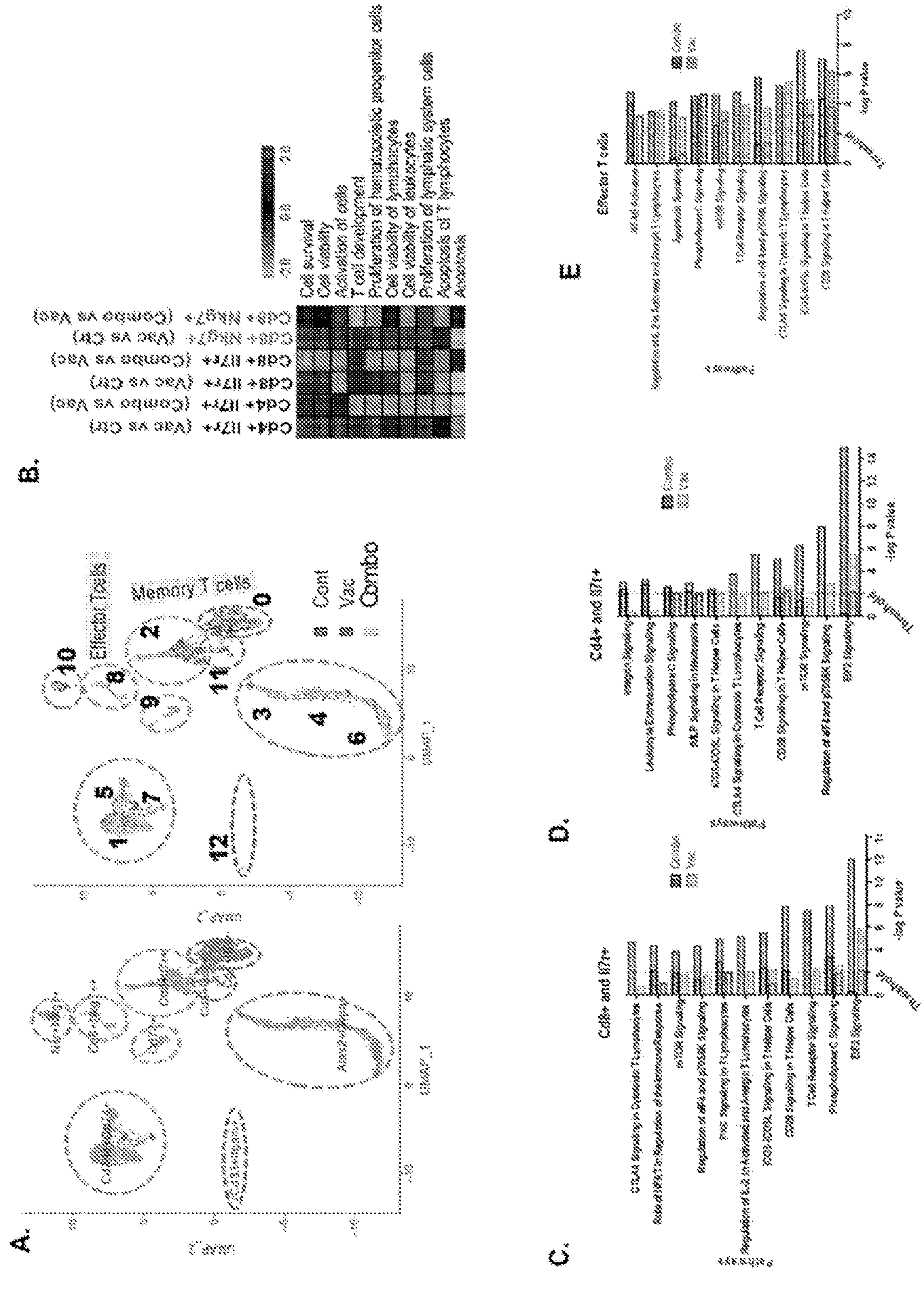
FIG. 6A-FIG. 6E show that scRNA-seq analysis demonstrates that vaccination alone and in combination with check-point inhibitor impacted T cell landscape. (A) scRNA-seq analysis on PBMCs cells isolated from control, DC/AML fusion vaccine treated, and vaccine+checkpoint point inhibitors treated mice. n=3 mice/group. Visualization of single cell clusters were generated using the UMAP approach from normalized data of 710 control, 884 vaccine-treated and 1,489 combination treated PBMCs. Cell clusters were annotated based on expression of established immune cell markers (e.g., T cells (CD3+), B cells (CD19+), memory T cell (Il7r+), effector cells (Sell+, CD62L−) (Left Panel). Relative proportions of cells in the clusters from each cohort are depicted with distinct colors (Right Panel). (B) Functional enrichment heatmap depicting increased (red) or decreased (green) functional categories in the vaccine alone and in combination treated samples. Heatmap was prepared based on z-scores calculated using ingenuity pathways analysis systems. Pathways that are significantly effected in various subsets of memory T cells: CD8a and Il7r+ T cells (C), CD4 and Il7r+ T cells (D), and effector T cells (E). Black and Grey bars represent significance of impact of vaccine alone and in combination with check-point inhibitor on selected signaling pathways. The extent of activation/increase of various significantly impacted pathways was shown using overlapping orange color bars.

The nature of immune response was further characterized by interrogation of the immune transcriptome following vaccination in the context of PD-1 blockade as compared to checkpoint inhibition or vaccination alone. Unsupervised analysis by scRNA-Seq identified comparable number of single cell clusters in all three cohorts of mice (FIG. 6A). Supervised analysis of CD4/IL7R and CD8/IL7R memory T cells demonstrated activation/upregulation in signaling pathways regulating T cell viability, proliferation and survival after vaccination that were further enhanced after treatment with both FV and checkpoint blockade. Consistent with these findings, there was a significant downregulation in apoptosis regulating genes (FIG. 6B). Similar findings were observed in CD8/Nkg7 expressing effector T cells with increase in viability, activation and proliferation and down-regulation of apoptosis genes (FIG. 6B).

Furthermore, signaling pathway analysis in the CD8/CDIL7R and CD4/CDIL7R memory compartment demonstrated significant effect on mTOR, CD28 and T cell receptor (TCR) signaling following vaccination compared to untreated controls. Interestingly, these signaling pathways were further upregulated following the addition of checkpoint blockade (FIG. 6C, D). Analysis of signaling in effector CD8/Nkg7 cells showed significant upregulation of NFkB, mTOR, CD28 and ICOS signaling after vaccination consistent with induction of inflammatory phenotype. Combination vaccine and anti-PD-1 treatment further enhanced the activation of these signaling pathways (FIG. 6E). These CD8/Nkg7+ effector T cells also depicted significant impact on T cell receptor signaling pathways (−log P value=3.9), this effect was further enhanced (−log P value=4.7) by addition of checkpoint blockade (FIG. 6E).

Figure 7:
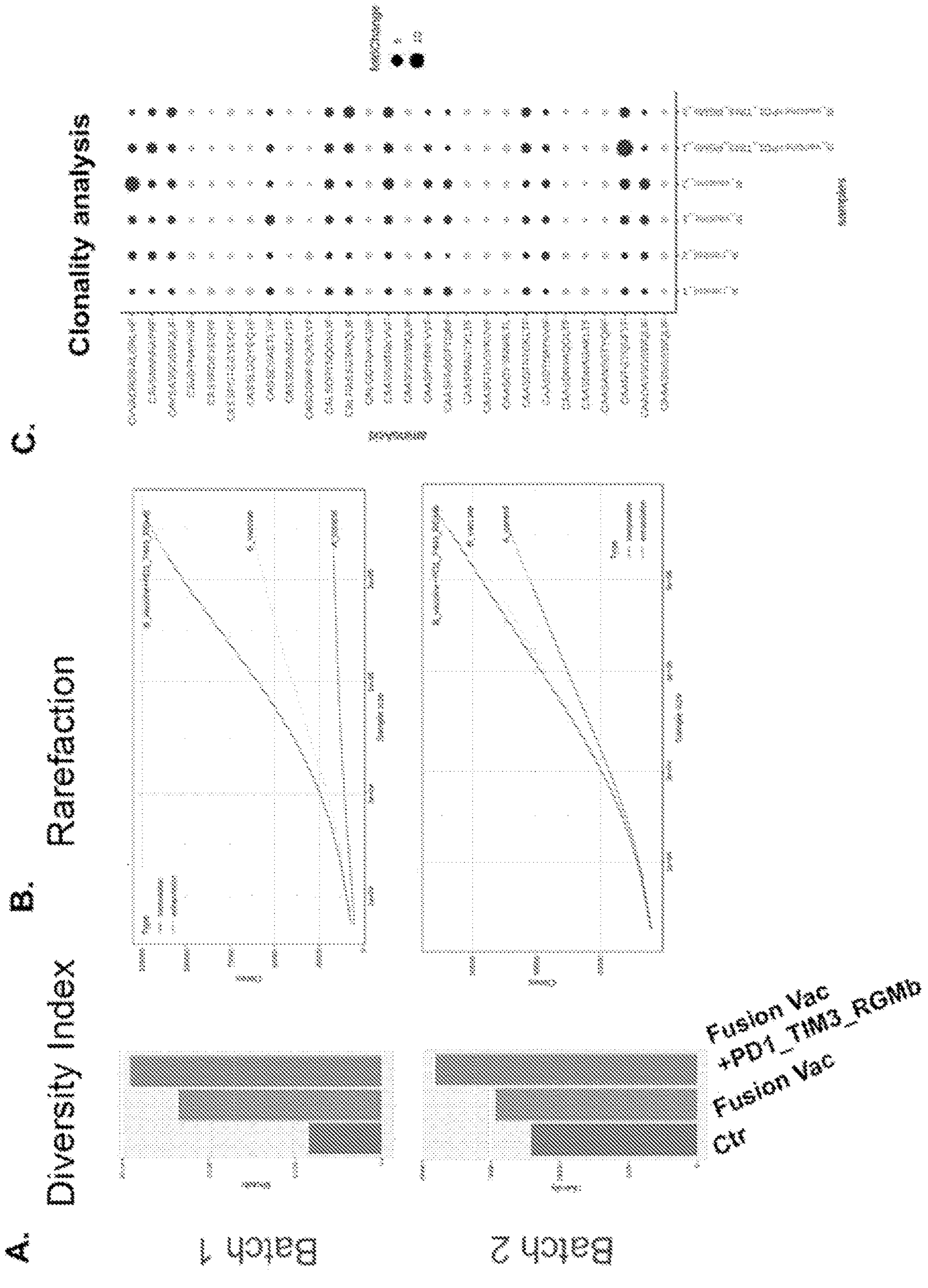
FIG. 7A-FIG. 7C shows that vaccination with DC/AML fusion vaccine leads to greater clonal T cell diversity, which is further enhanced following checkpoint blockade. C57BL/6J mice were treated as described above. Peripheral blood (PB) was then collected and assessed for T cell diversity using targeted TCR profiling. (A) Inverse Simpson diversity index indicating that vaccine alone and in combination with checkpoint enhance T. (B) Refraction diversity analysis. (C) Bubble plot of top TCR clone's expression after vaccination alone or in combination with checkpoint inhibitors. Columns represent samples and rows represent amino acid sequence of different TCR clones. The TCR clones with significant increase and decrease are shown with red and green colors respectively. Fold change of top 10 TCR clones for each sample is calculated compared to the untreated control samples.
Figure 8:
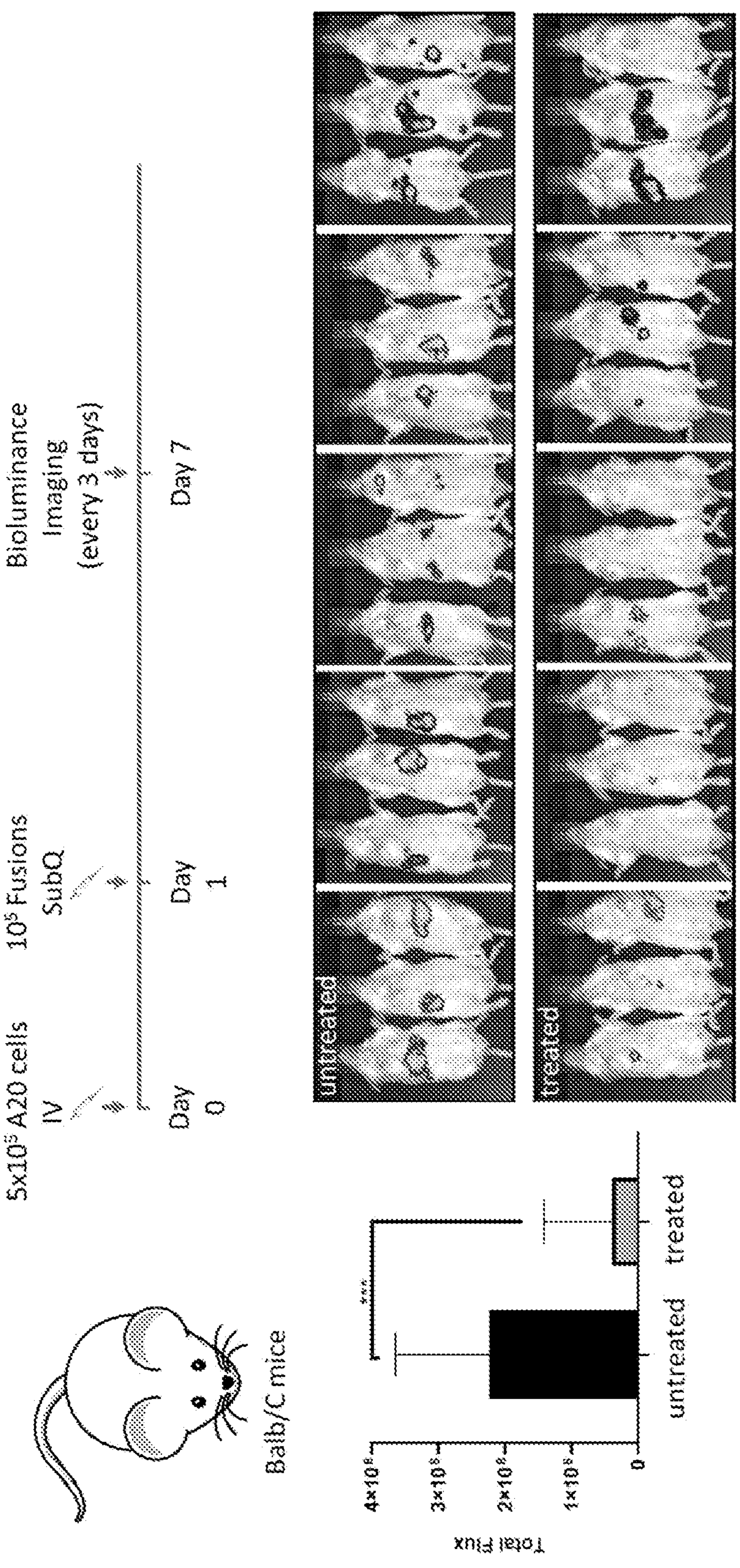
FIG. 8 shows Lymphoma Immunocompetent Murine Model. An initial in vivo experiment in which fusions within alginate and 41BBL show similar results to the regular fusions or even better. Can prove that we have the capability of inserting the scaffold sub Q in vivo and suggests that although the fusions are located in the scaffold an immune response is present.
Figure 9:
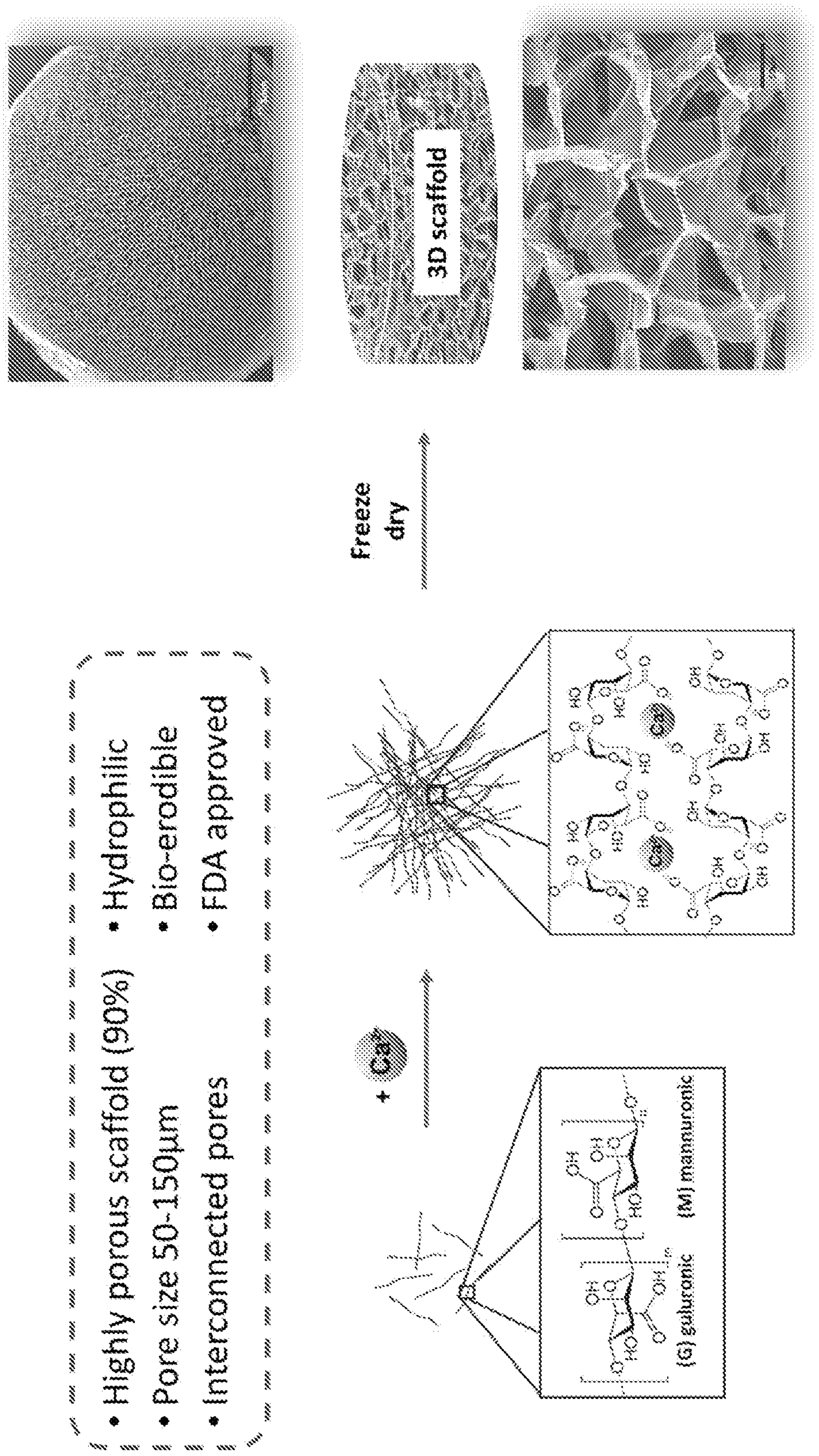
FIG. 9 shows Alginate Based Biomatrix. Alginate, a sugar polymer, is crosslinked using calcium ions to form a hydrogel that can be freeze dried to get a 3D scaffold with connected pores that fit in size to cell plating. By carbodiimide chemistry we can covalently bind costimulatory molecules and following cross linking and freeze dry receive a scaffold that is embedded with molecules that promote T cell activation when introduced to antigens in the context of MHC. In confocal picture is shown mature DC within an Alginate scaffold. On the right: The Alg/RGD/41BBL scaffold can serve as a supporting microenvironment for the co-culture of T cells and fusion vaccine in vitro or in vivo when T cells enter the scaffold.
Figure 10:
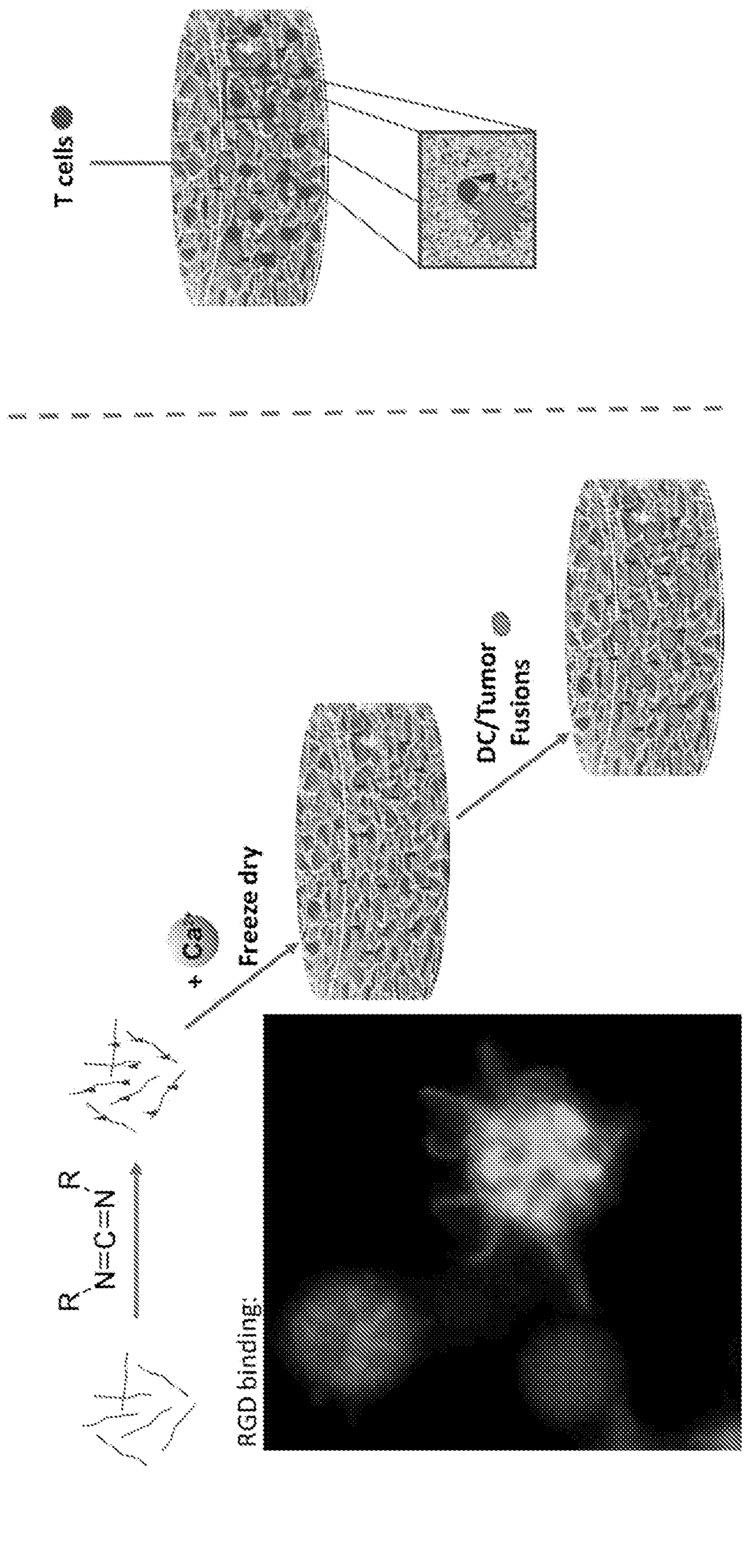
FIG. 10 shows Covalent Binding of Costimulatory Molecules.
Figure 11:
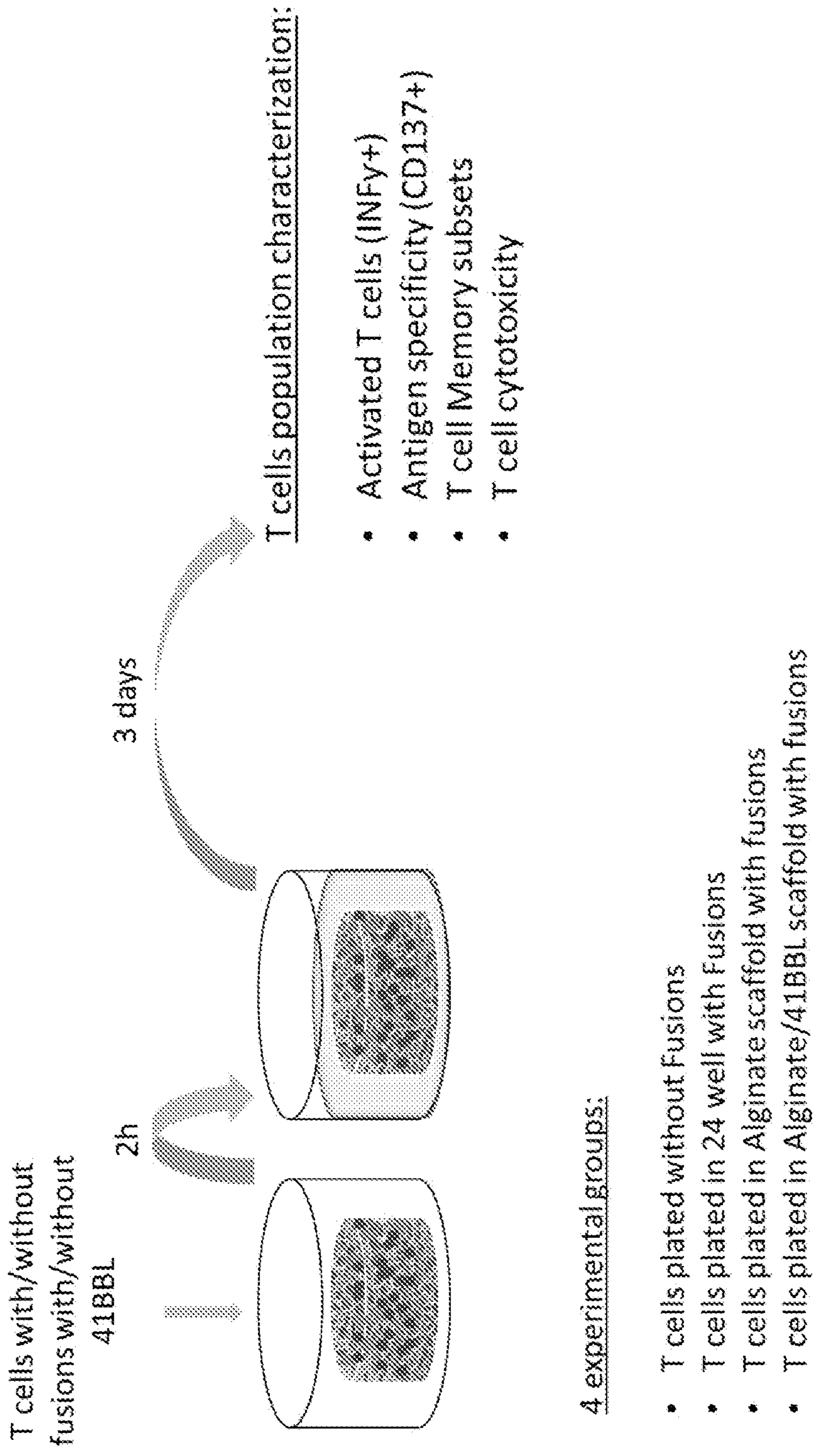
FIG. 11 shows In vitro Experiment Design (A20 Lymphoma model). We cultured syngeneic T cells with DC/A20 fusion vaccine within a scaffold with or without bound 41BBL and examined the T cells cytotoxicity by a CTL assay. A second CTL assay comparing the cytotoxicity of T cells after co-culture with fusions within alginate scaffold with IL15 and IL7. Also showing repeat of the initial result regarding the 41BBL scaffold. An initial in vivo experiment in which fusions within alginate and 41BBL show similar results to the regular fusions or even better. Can prove that we have the capability of inserting the scaffold sub Q in vivo and suggests that although the fusions are located in the scaffold an immune response is present.
Figure 12:
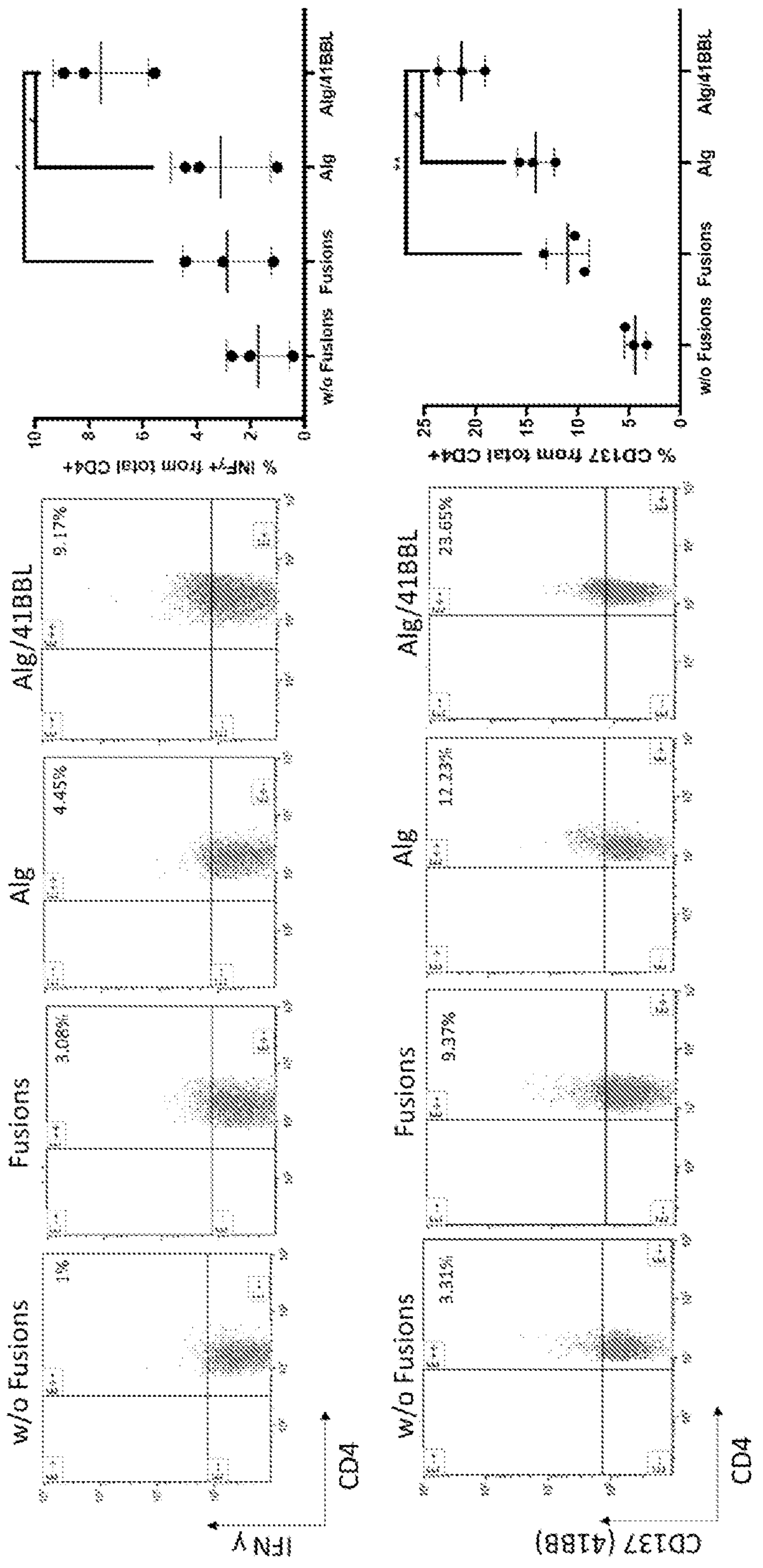
FIG. 12 shows CD4+ T Cells Activation and Antigen Specificity.
Figure 13:
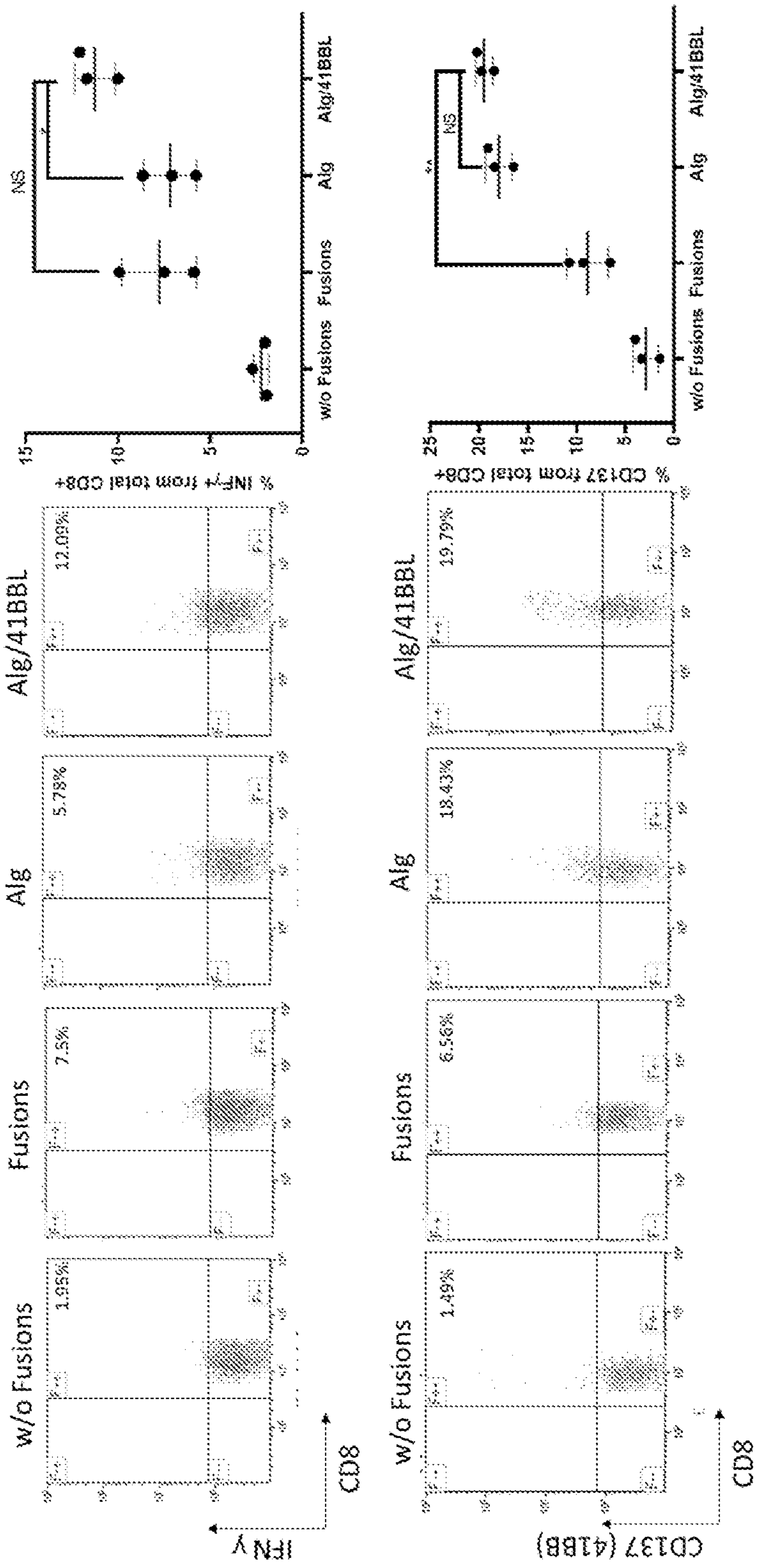
FIG. 13 shows—CD8+ T Cells Activation and Antigen Specificity.
Figure 14:
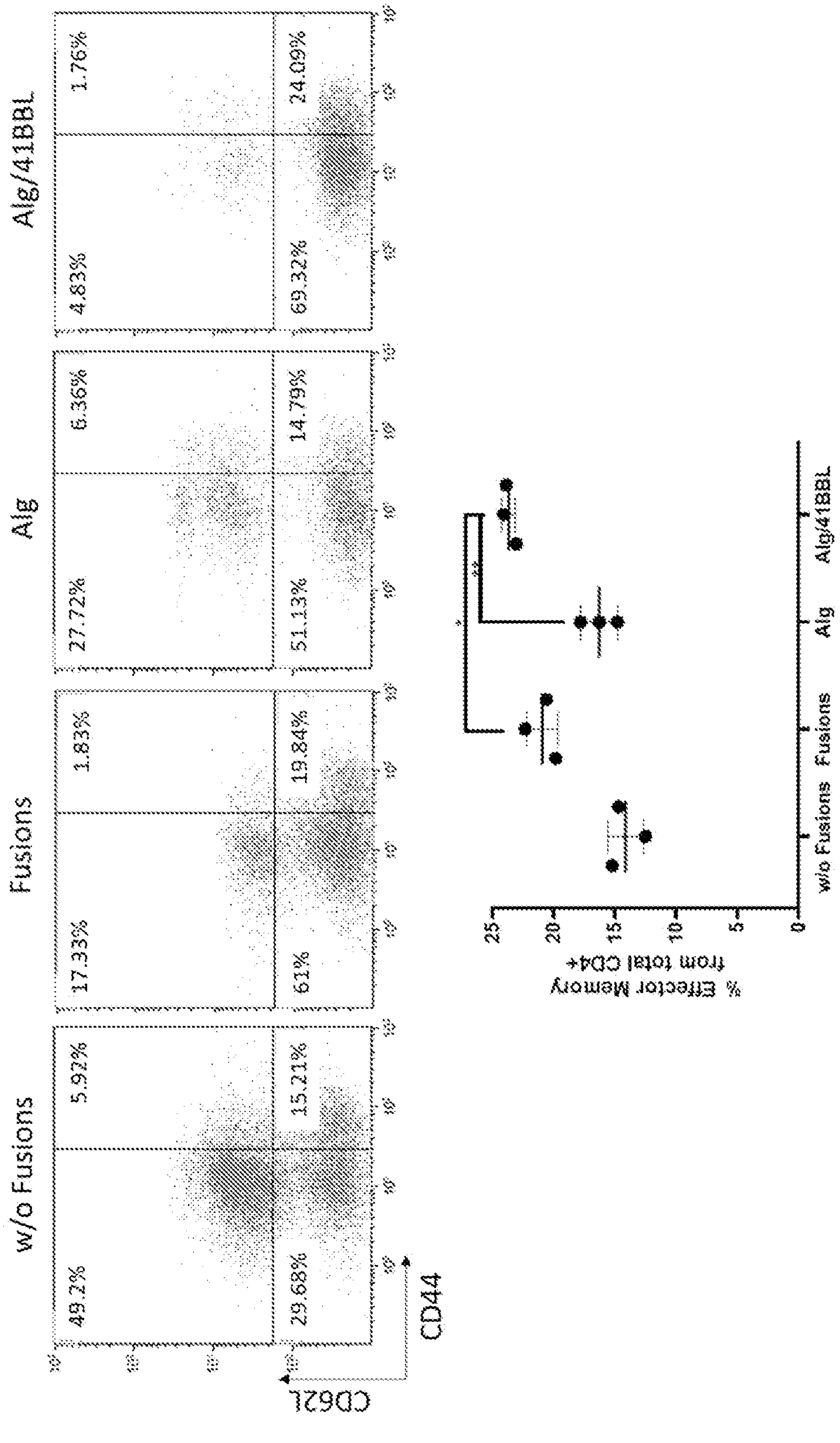
FIG. 14 shows CD4+ T Cells Memory Subsets.
Figure 15:
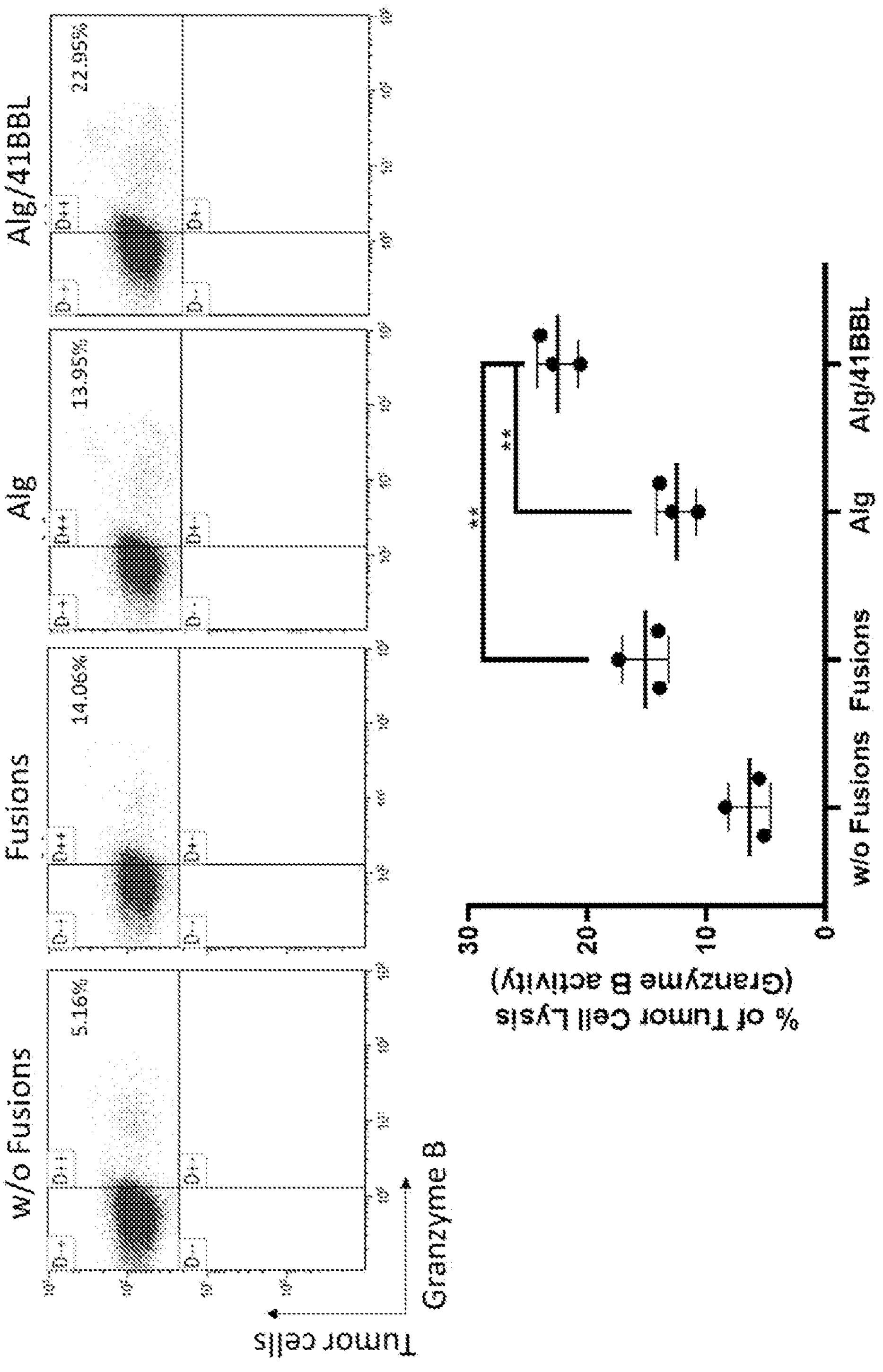
FIG. 15 shows T Cells Cytotoxicity to Tumor Cells.
Figure 16:
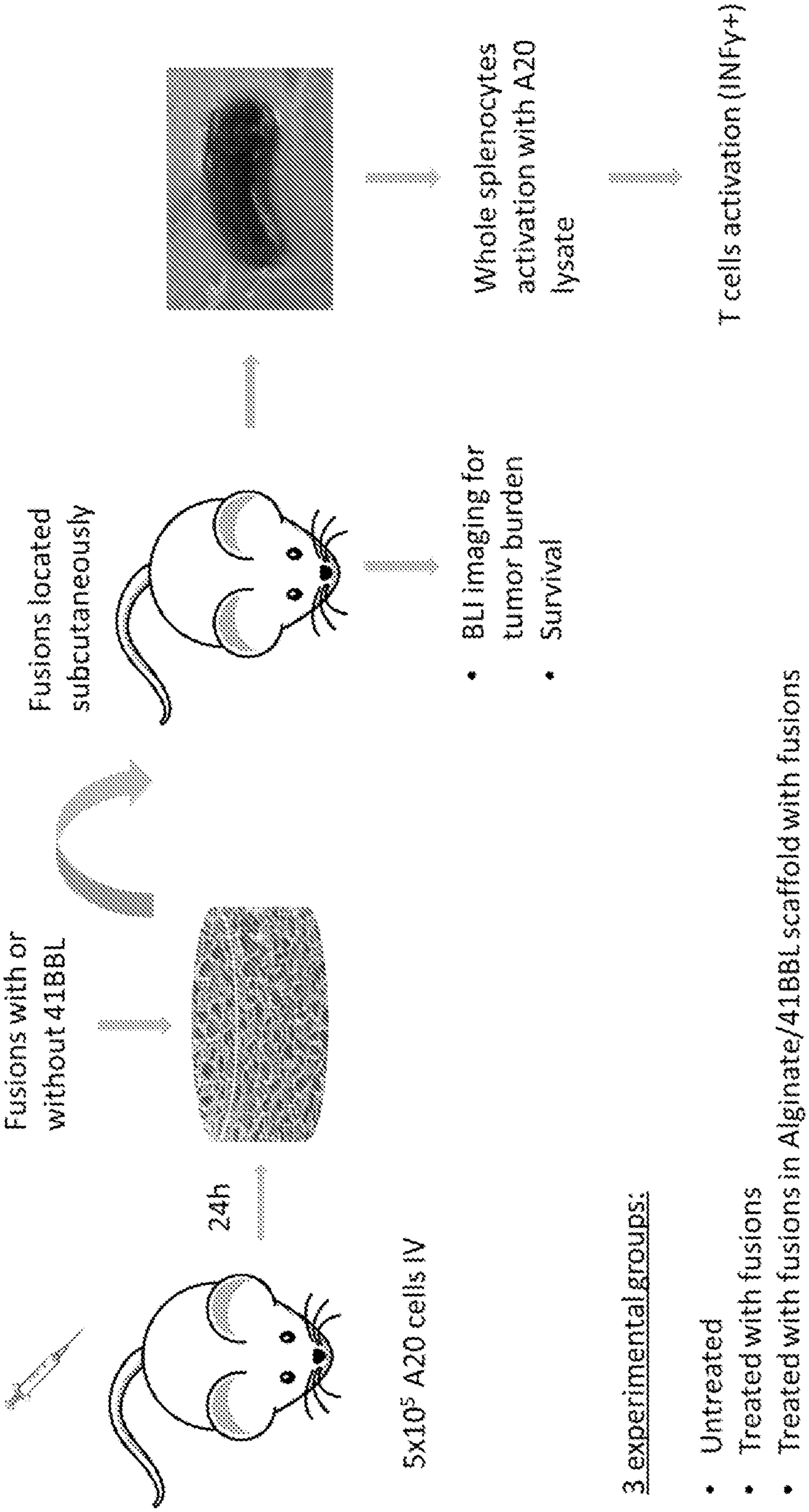
FIG. 16 shows In vivo Experiment Design.
Figure 17:
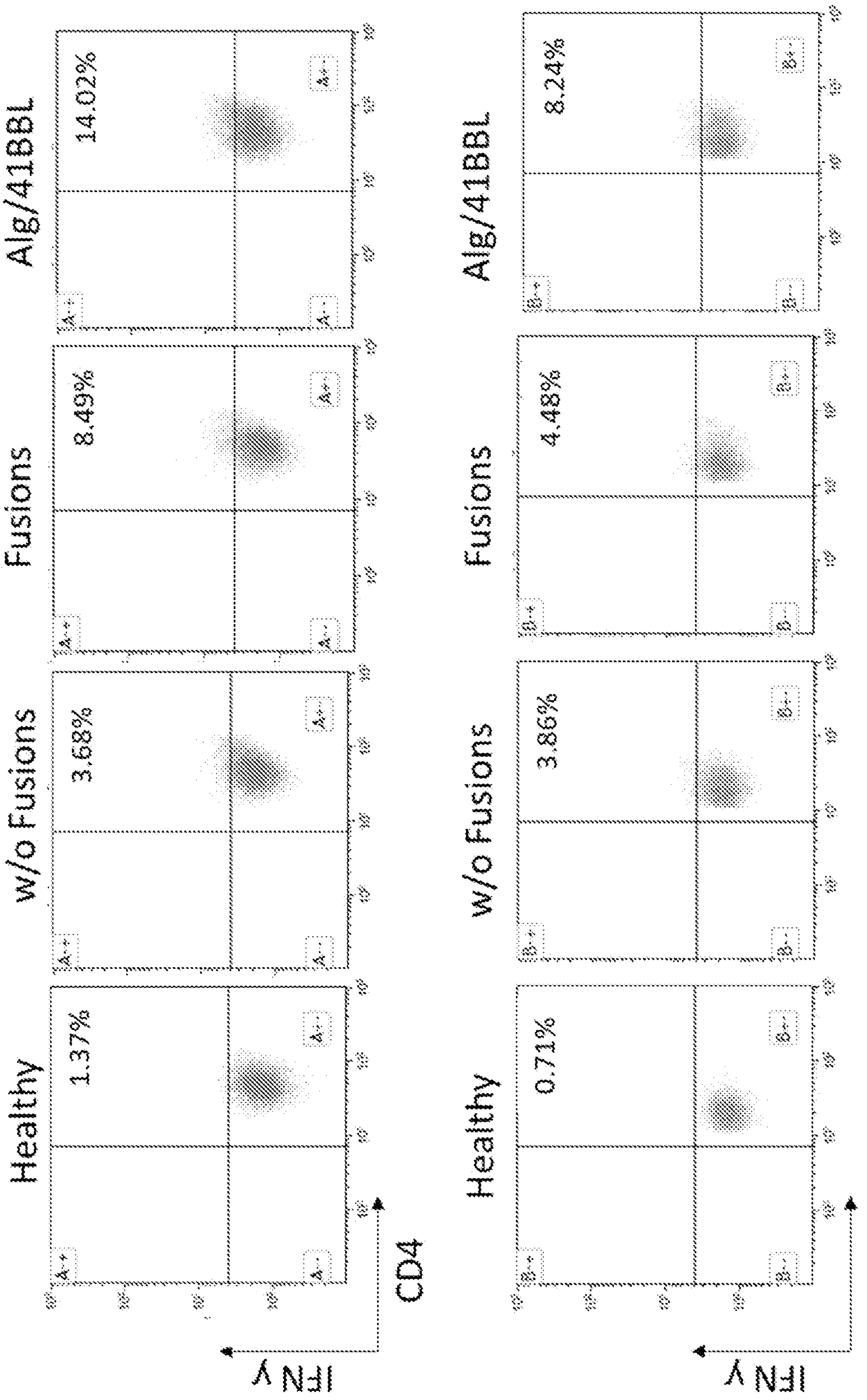
FIG. 17 shows Activation by Tumor Lysate.
Figure 18:
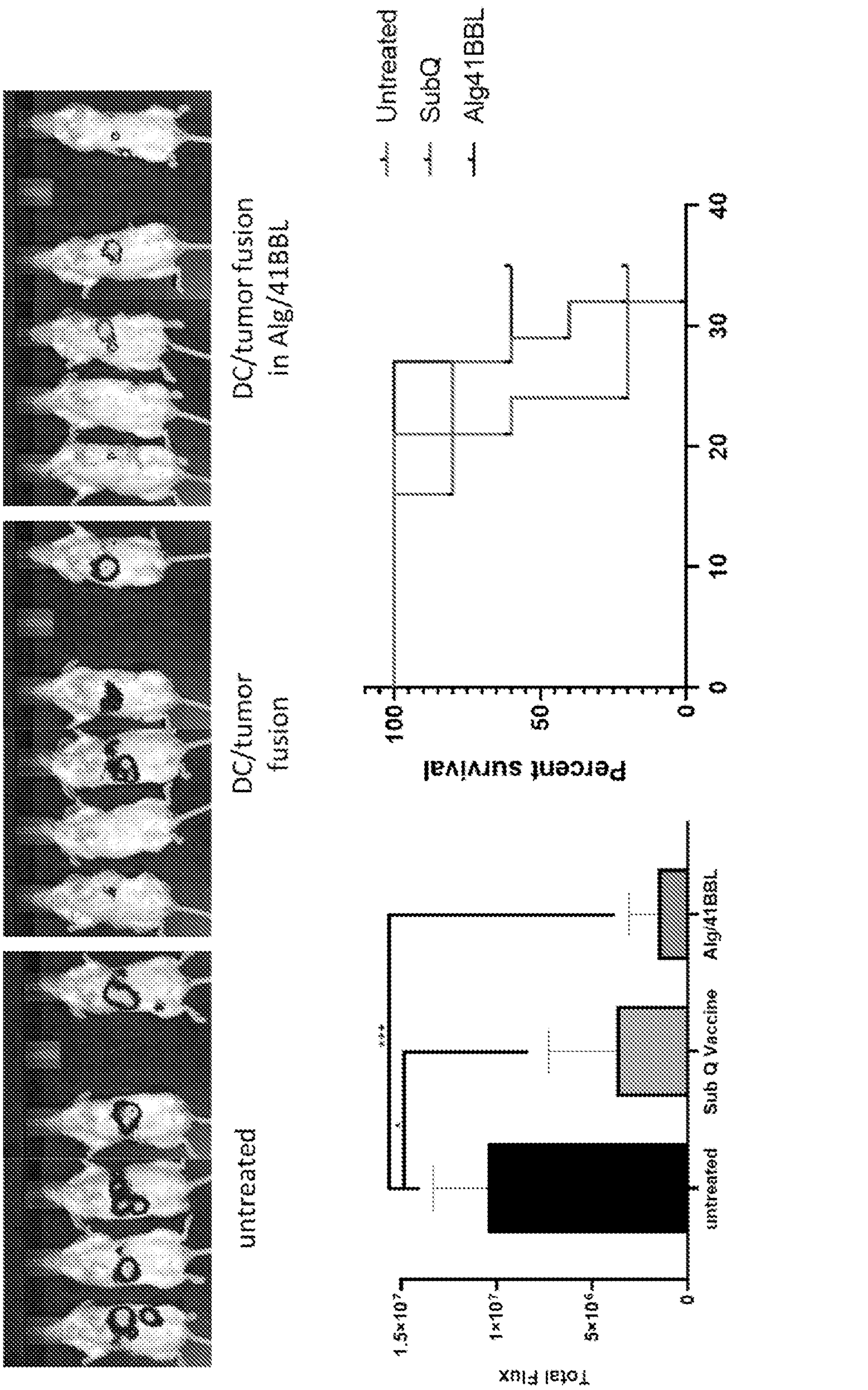
FIG. 18 shows Tumor Burden and Survival.
Figure 19:
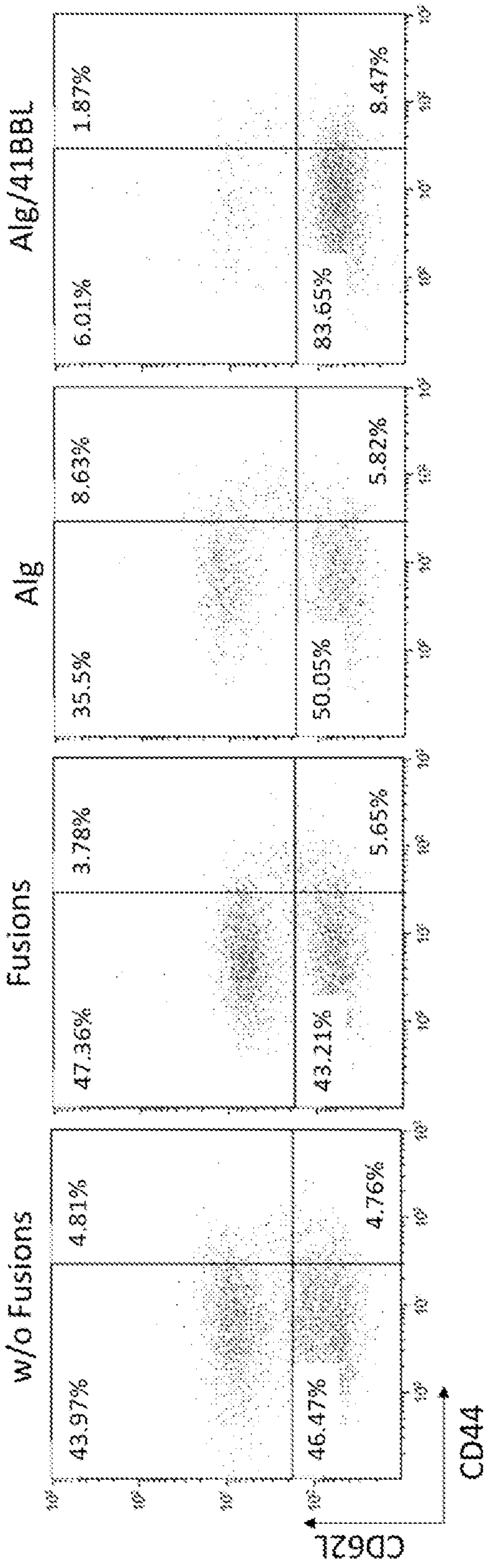
FIG. 19 shows CD8 FC results.
Figure 20:
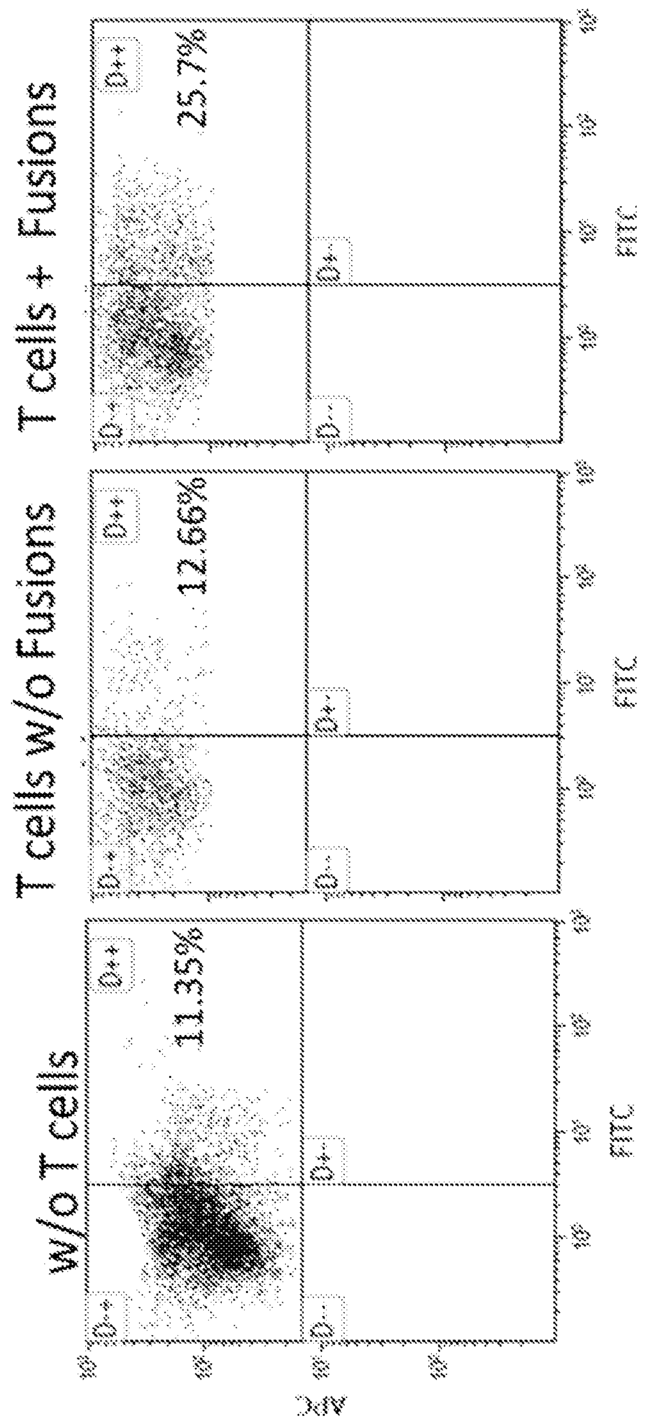
FIG. 20 shows CTL for Lymphoma Patient Fusions.
Figure 21:
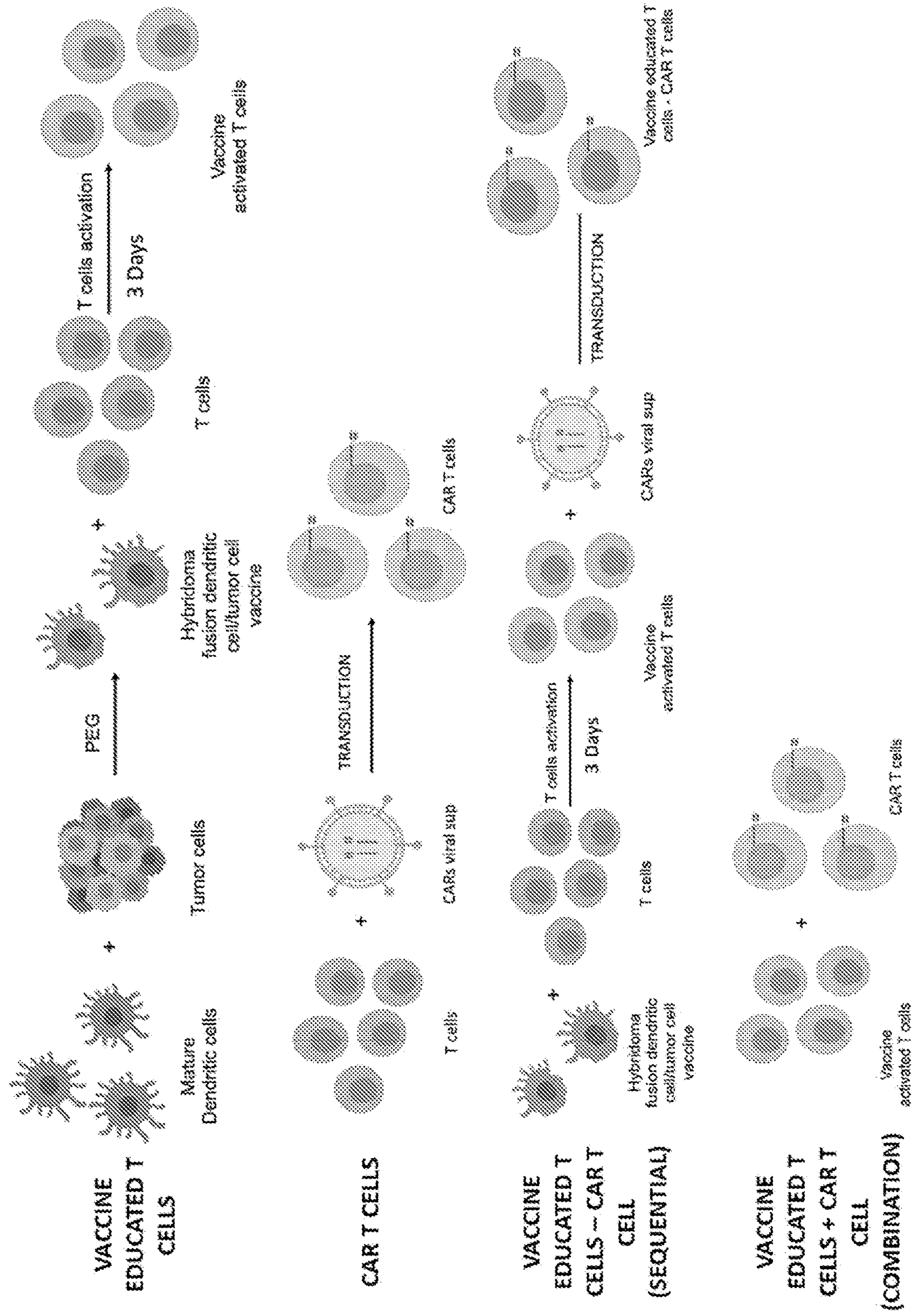
FIG. 21 shows T cells education ex vivo modalities.
Figure 22:
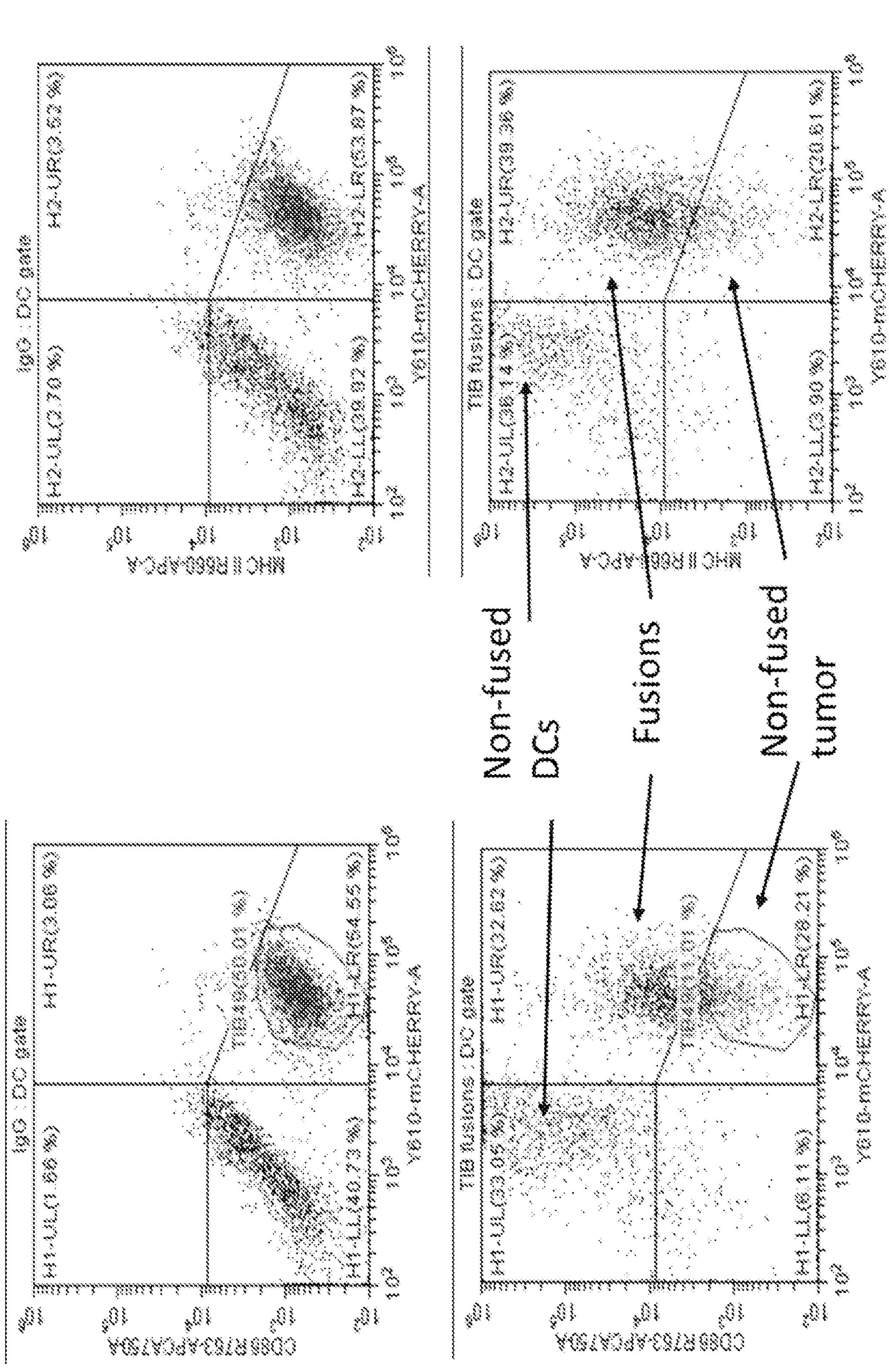
FIG. 22 shows generation of murine dc/tumor fusions
Figure 23:
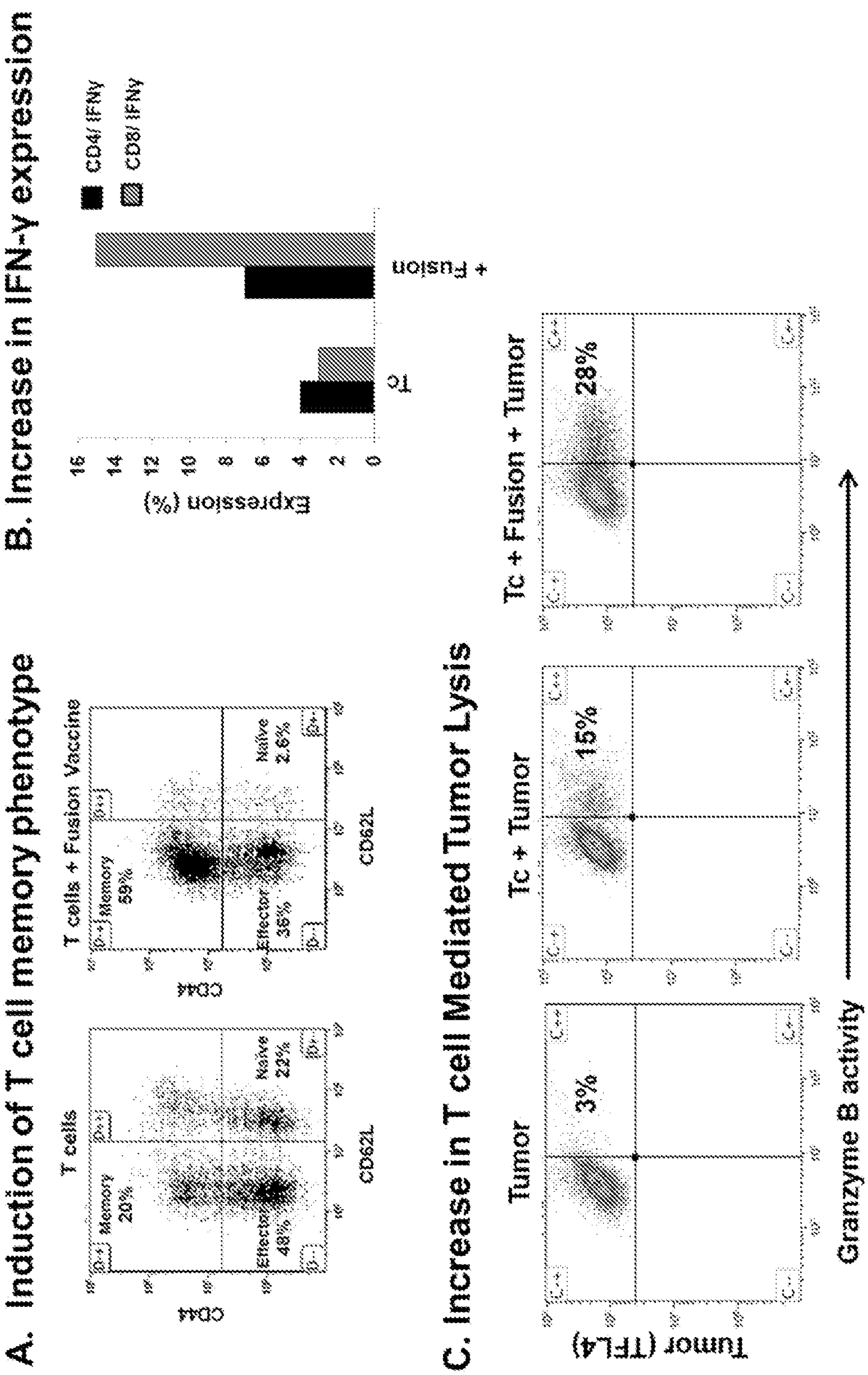
FIG. 23A-FIG. 23C show ex vivo generation of vaccine educated T cells
Figure 24:
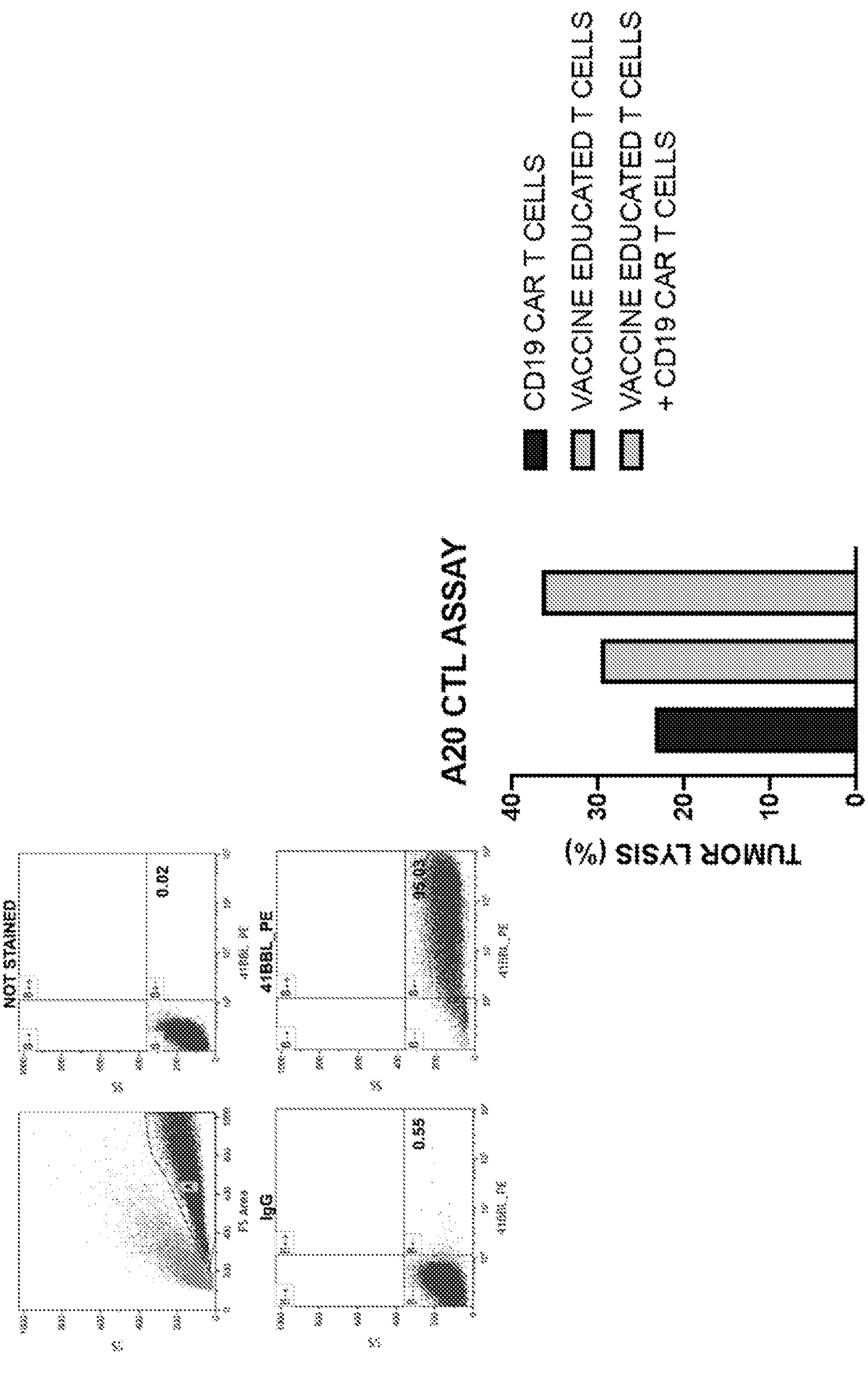
FIG. 24 shows cytotoxic killing capability of CD19 CAR-T cells and vaccine educated T cells alone and in combination.
Figure 25:
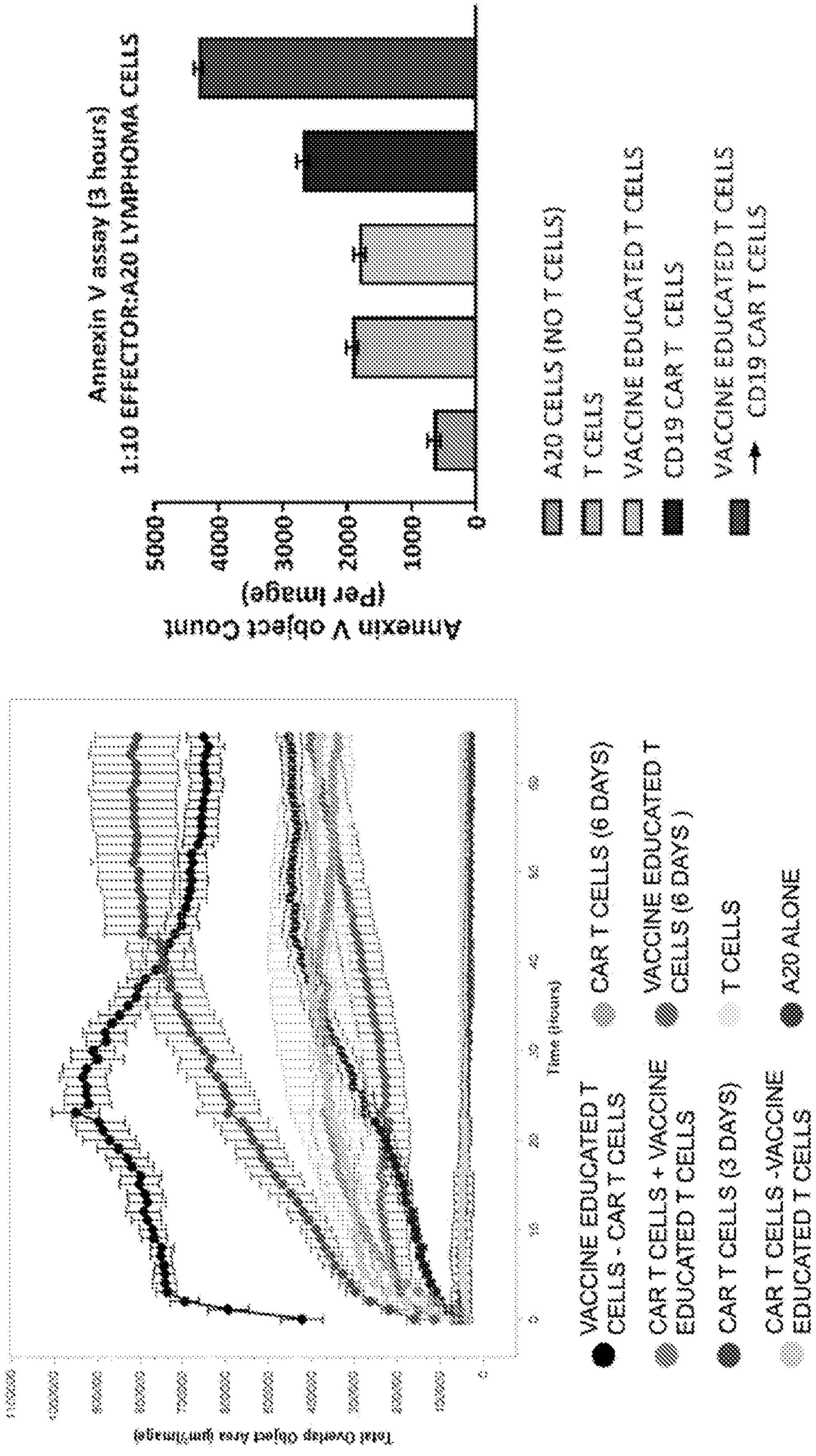
FIG. 25 shows increased caspase 3/7, annexin V activated apoptosis, and cytotoxic T lymphocyte-mediated killing of sequentially vaccine educated—transduced T cells and CAR-T cells and vaccine educated T cells in combination.
Figure 25:
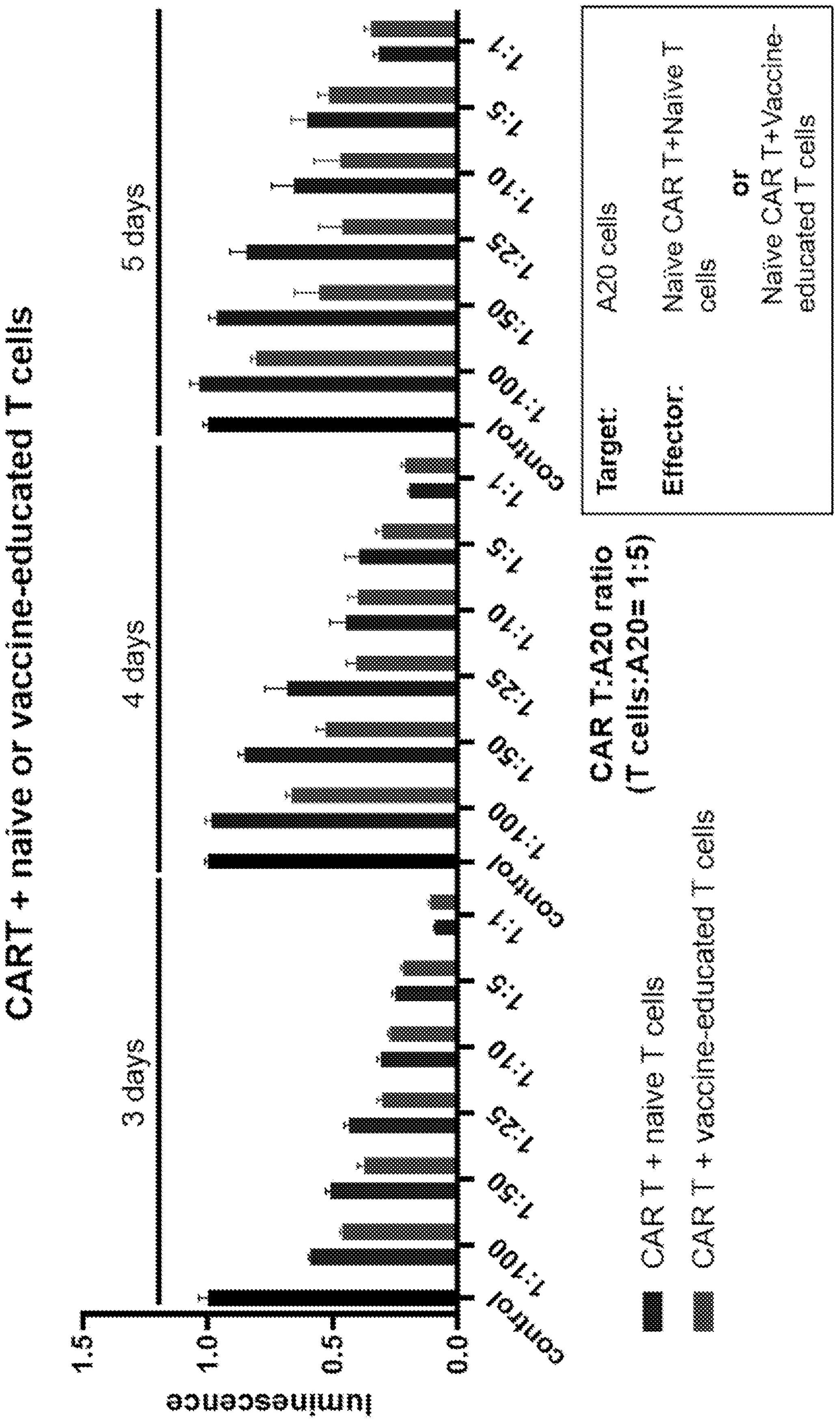
Figure 26:
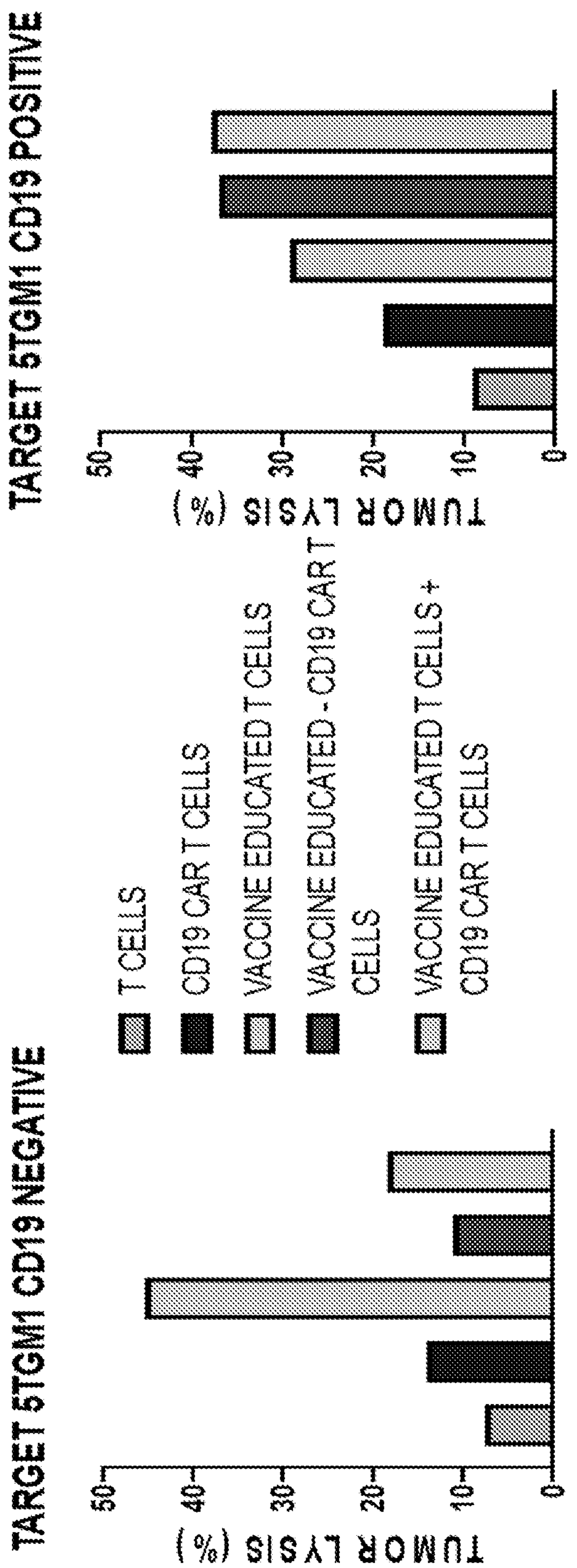
FIG. 26 shows the synergic effect of the combination of CAR-T cells and vaccine educated T cells is based upon on the CAR-T cells function antigen dependent.
Figure 27:
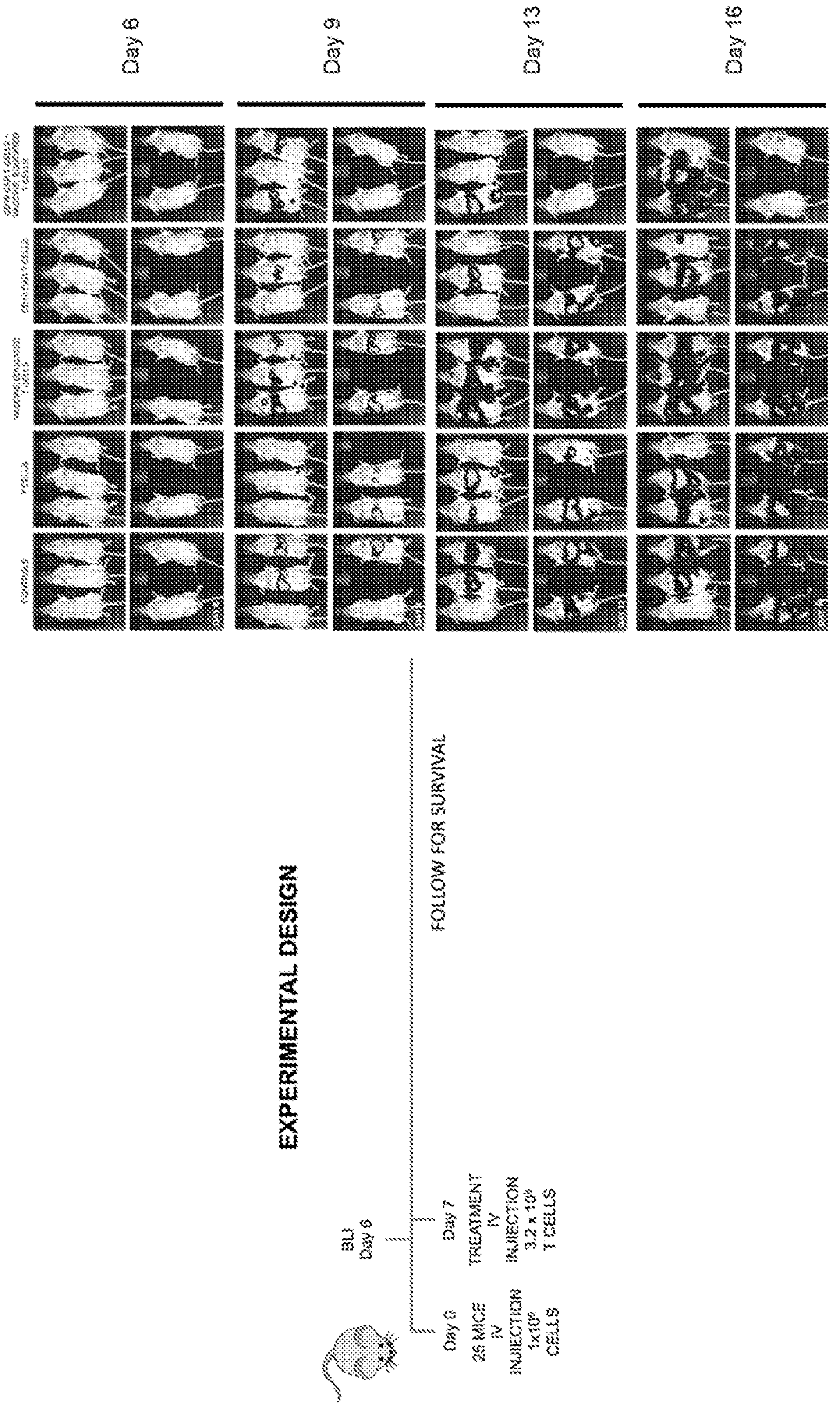
FIG. 27 shows combination treatment with CAR-T cells and vaccine educated T cells reduce tumor burden and slow progression in A20 lymphoma model
Figure 28:
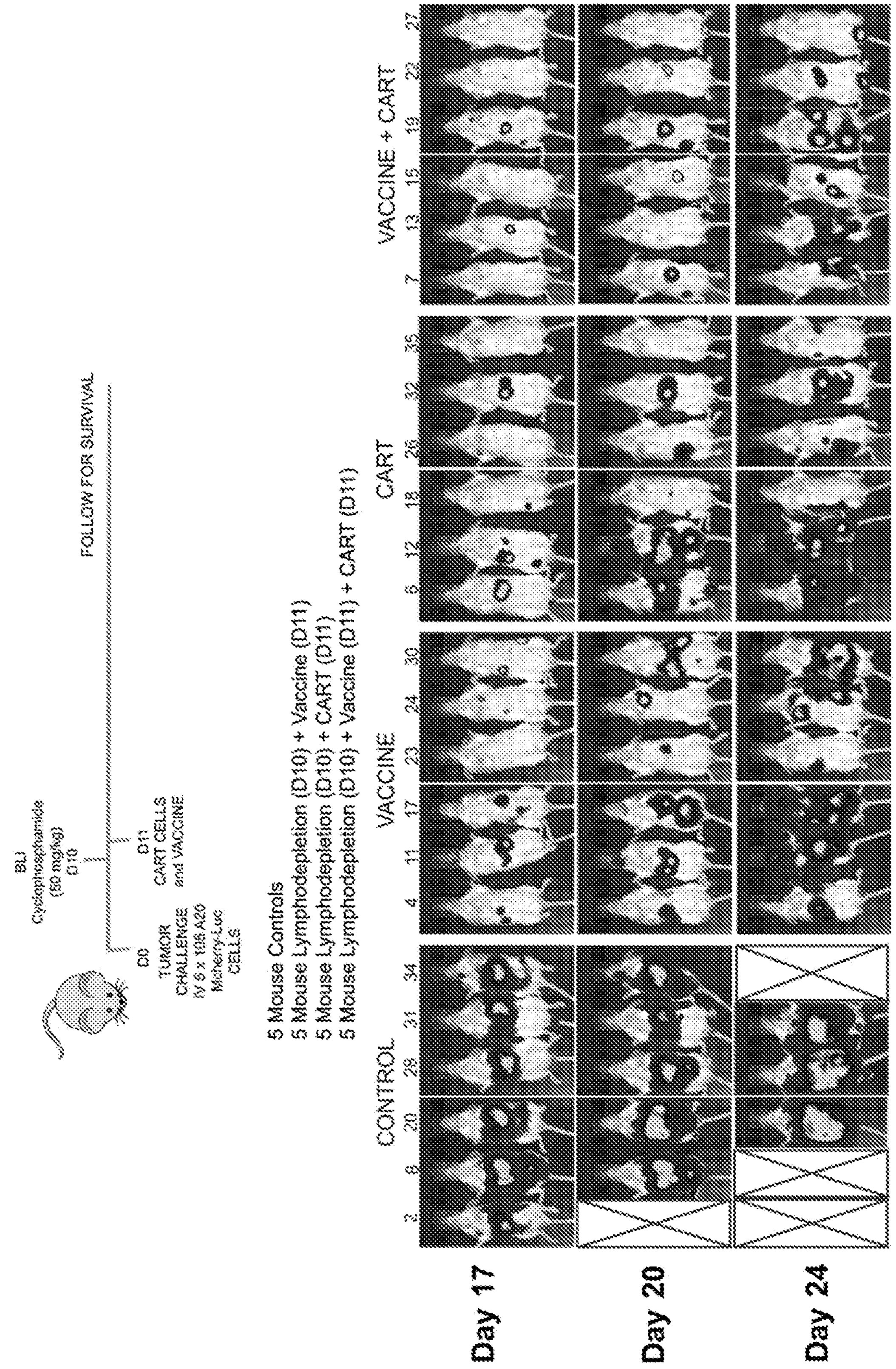
FIG. 28 shows active vaccination in combination with CAR-T cells treatment reduce tumor burden and slow progression in A20 lymphoma model
Figure 29:
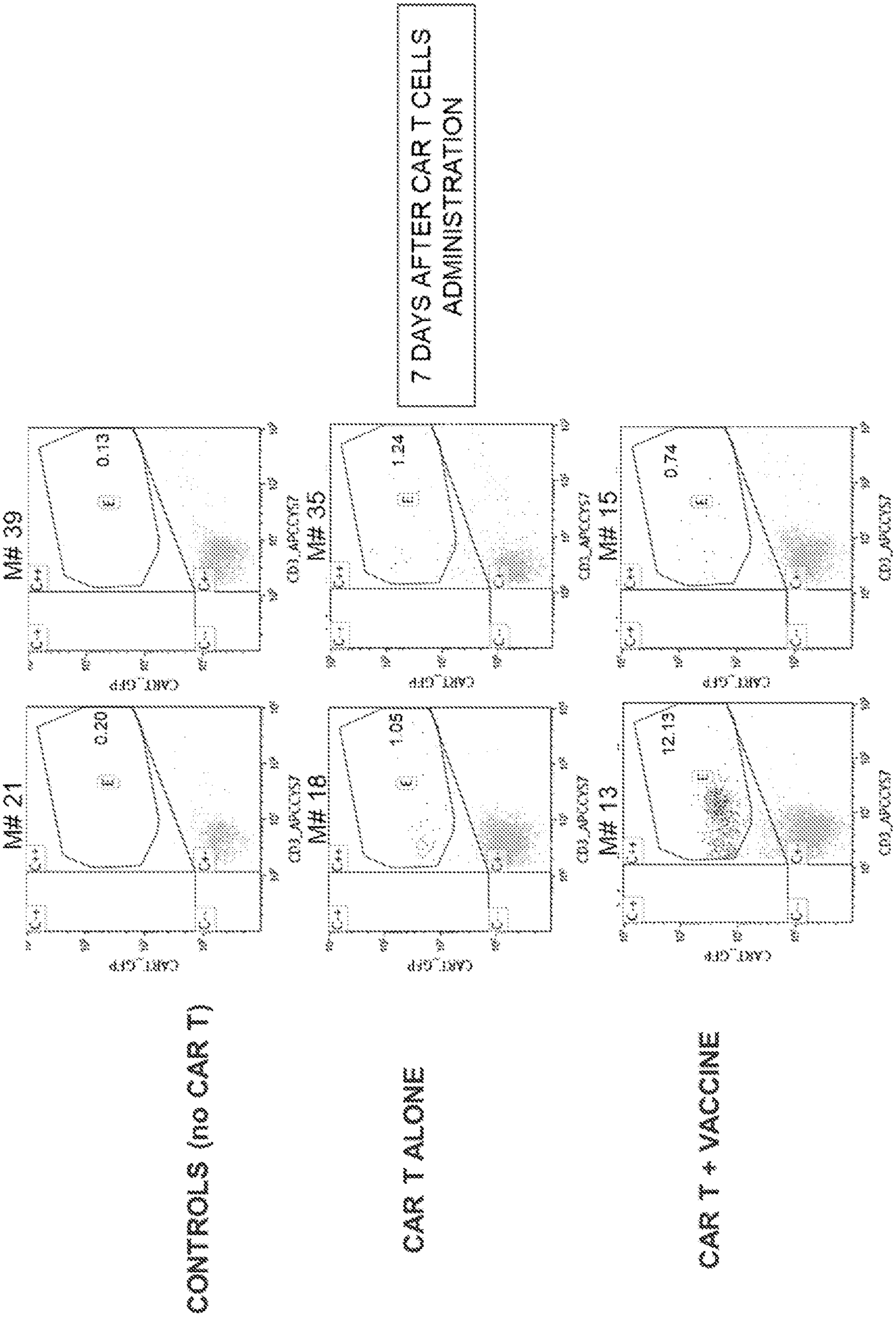
FIG. 29 shows vaccine administration increases GFP tagged CAR-T cells in mice peripheral blood
Figure 30:
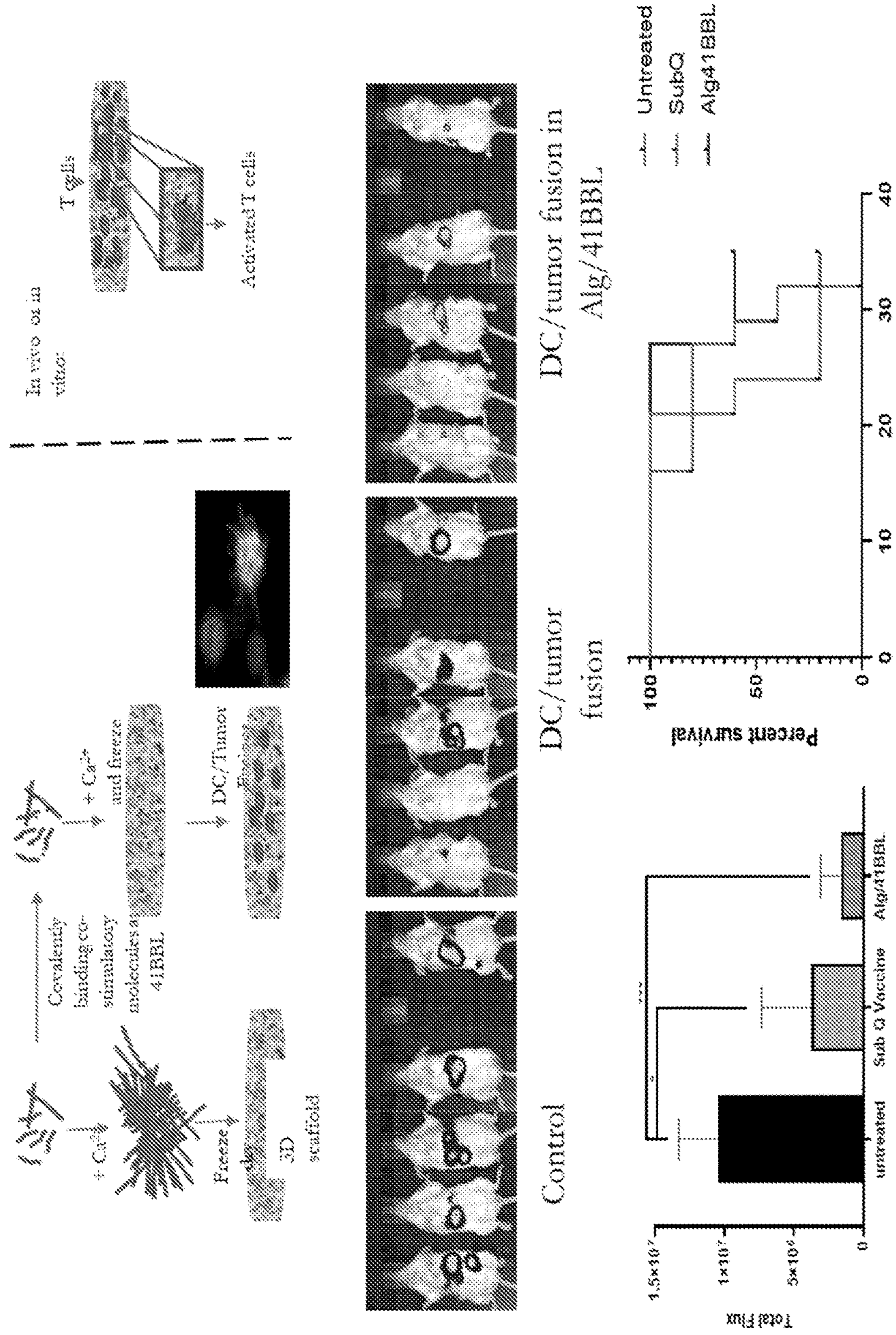
FIG. 30 shows Second Generation Cellular Cancer Vaccines: Creating an Artificial Lymph Node. Alginate, a sugar polymer, is crosslinked using calcium ions to form a hydrogel that can be freeze dried to get a 3D scaffold with connected pores that fit in size to cell plating. By carbodiimide chemistry we can covalently bind costimulatory molecules and following cross linking and freeze dry receive a scaffold that is embedded with molecules that promote T cell activation when introduced to antigens in the context of WIC. In confocal picture is shown mature DC within an Alginate scaffold. On the right: The Alg/RGD/41BBL scaffold can serve as a supporting microenvironment for the co-culture of T cells and fusion vaccine in vitro or in vivo when T cells enter the scaffold.
Figure 31:
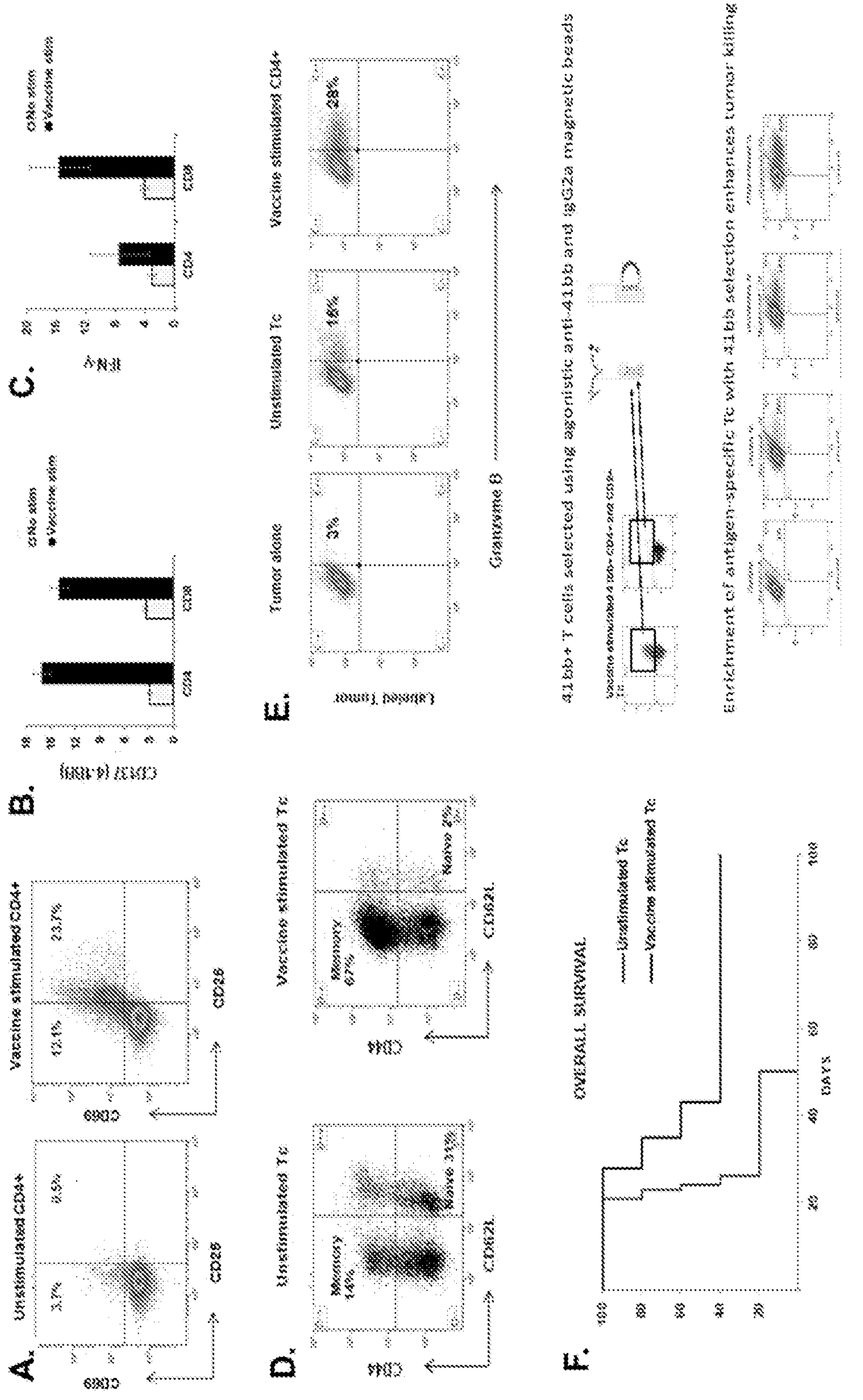
FIG. 31A-FIG. 31F show Vaccine Educated T cells as Adoptive Immunotherapy.
Figure 32:
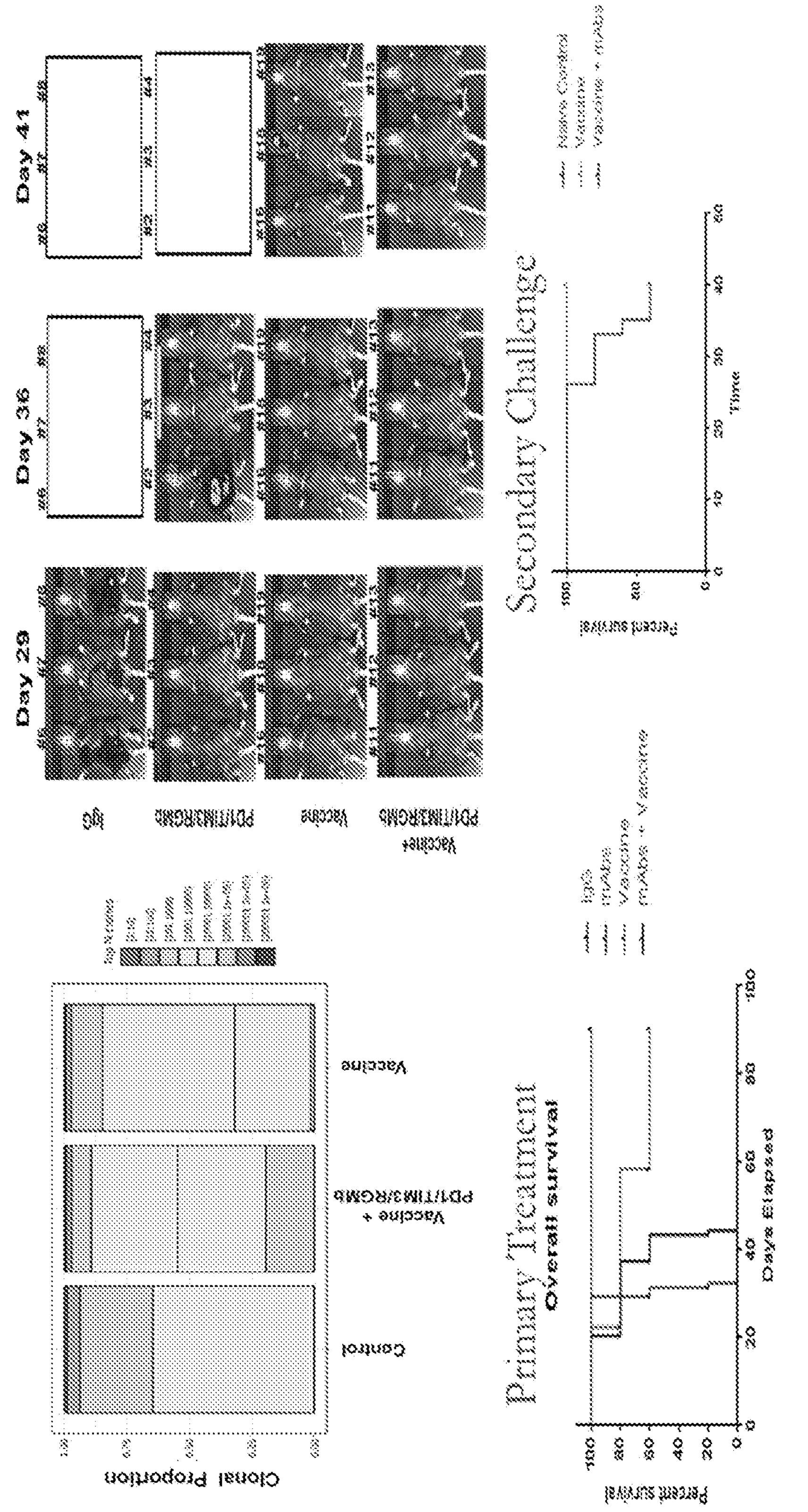
FIG. 32 shows Vaccination in Conjunction with Checkpoint Inhibition.
Figure 33:
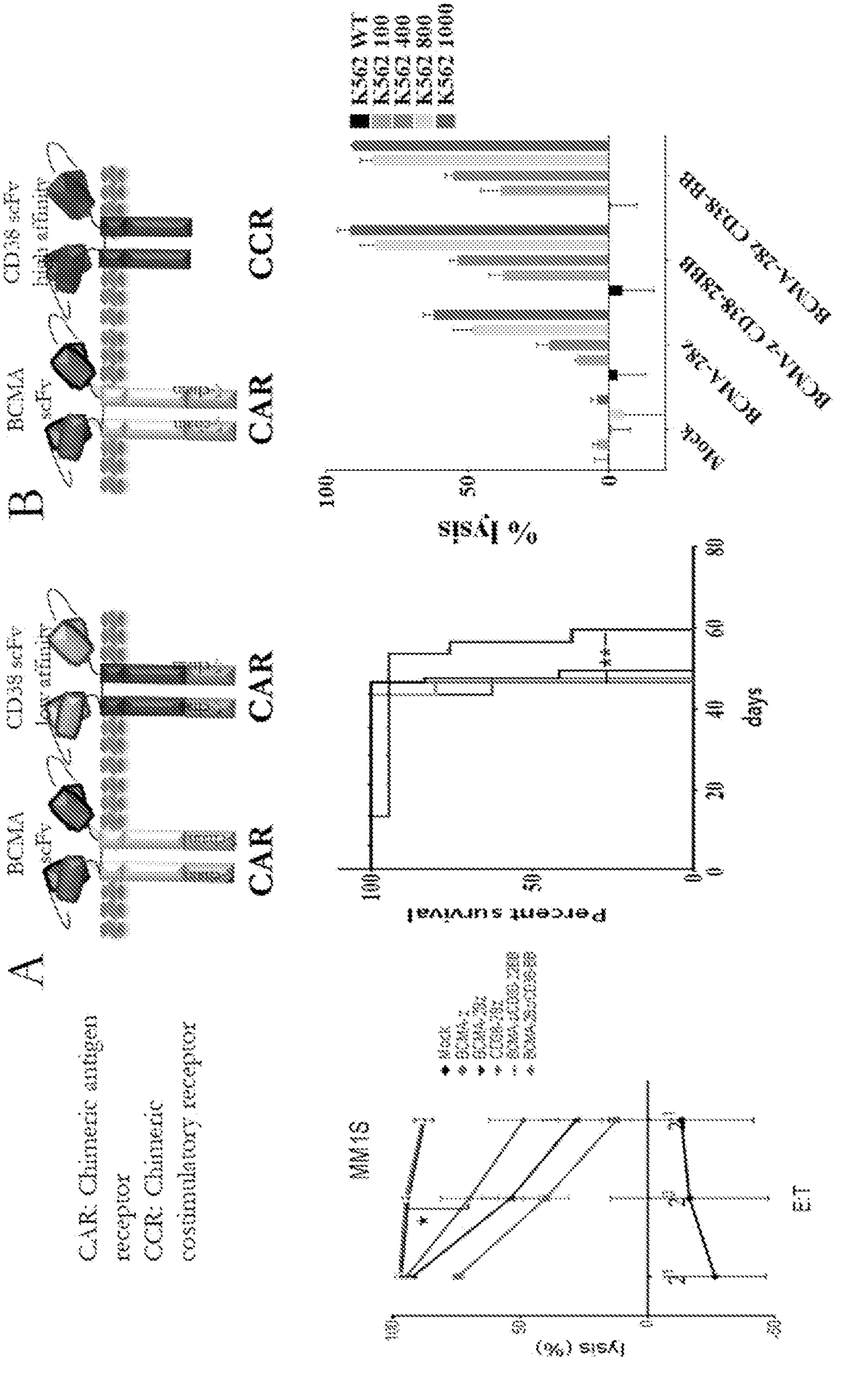
FIG. 33A and FIG. 33B show Combining Costimulatory Chimeric Receptor to Address Tolerance and Prevent Antigen Escape.
Figure 34:
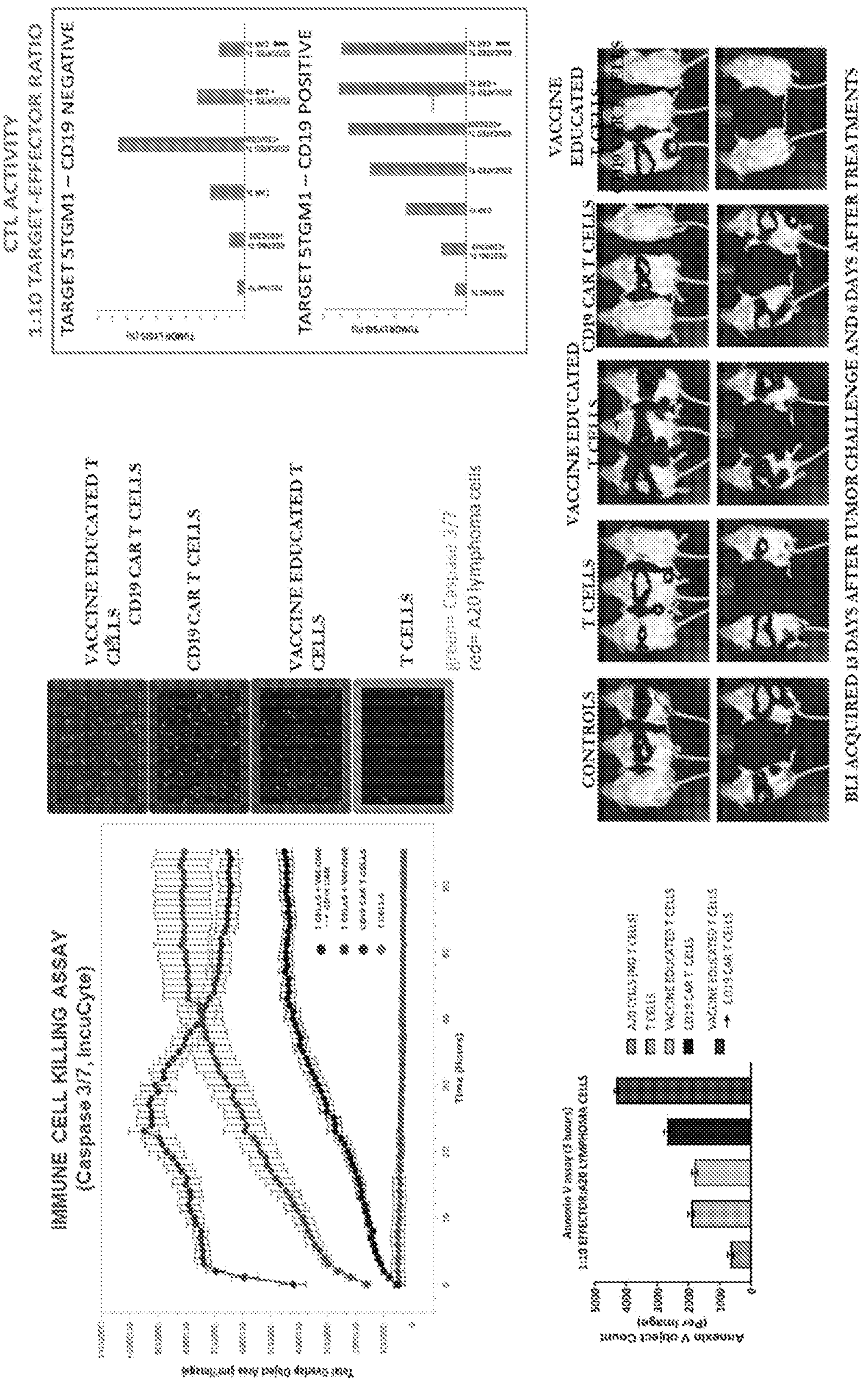
FIG. 34 shows Vaccination in the Conjunction with CAR T cells.

Vaccination with DC/AML Fusion Vaccine in Combination with Checkpoint Blockade Results in Greater Clonal T Cell Diversity The effect of vaccination alone or in conjunction with checkpoint blockade on the T cell repertoire was interrogated by clonotypic analysis using targeted TCR profiling studies. The diversity index and rarefaction analysis demonstrated that vaccination resulted in the selective expansion of clonal populations and enhanced diversity of the T cell repertoire compared to peripheral blood samples derived from untreated control mice (FIG. 7A,B). Remarkably, diversity was significantly further expanded by sequential therapy with DC/AML fusions and combined checkpoint blockade suggesting the expansion of vaccine educated cells with tumor specificity. The clone tracking analysis of top TCR clones indicated that multiple TCR clones are significantly modulated (absolute FC>2) after vaccine treatment (FIG. 7C). Interestingly, a subset of these vaccine modulated TCR clones depicted further enhanced up or down-regulation on combined therapy indicating synergistic impact of vaccine and checkpoint therapy in building anti-tumor immunity (FIG. 7C). In summary, combinational therapy with vaccination and checkpoint blockade resulted in the selective further expansion of vaccine-educated cells creating a further pattern of enhanced clonal dominance.

Discussion

Greater understanding of the mutational landscape in AML has resulted in better prognostication and the development of targeted therapies in subsets of patients. However, while the use of standard chemotherapy and targeting agents have resulted in enhanced rates of response, curative outcomes remain elusive for the majority of patients. Allogeneic transplantation is curative for a subset of patients due to the graft versus disease effect mediated by alloreactive lymphocytes. This treatment strategy suggested that cellular immune based therapy was capable of fully eradicating malignant hematopoiesis including the primitive stem cell compartment albeit with significant associated toxicity due to concurrent risks for GVHD and infection. There has been significant interest in developing more targeted immune based therapies utilizing effector cells from the patient without the need for transplantation.

A major advance in cancer immunotherapy was the discovery of the role of negative costimulatory factors such as CTLA-4/B7 and the PD-1/PD-L1 pathways in promoting T cell exhaustion in patients with malignancy thereby facilitating immune escape and disease growth. In contrast, blockade of these negative checkpoints has led to dramatic disease regression and improved outcomes in a subset of patients with advanced solid tumors transforming the therapeutic landscape and demonstrating the truly unique potency of immune effector cells'[15]. However, despite the susceptibility to immune based targeting demonstrated with allogeneic transplantation, the efficacy of checkpoint inhibitors has been disappointing in hematologic malignancies including in patients with AML[16]. It has been postulated that the lack of a significant intrinsic T cell response in AML was a likely explanation for why there was an insufficient immune substrate for checkpoint inhibition to be effective.

We have developed a personalized tumor vaccine in which patient derived tumor cells are fused with autologous dendritic cells such that a broad array of tumor antigens including unique neoantigens are presented in the context of DC mediated costimulation[17,18]. In a phase II clinical trial, vaccination was associated with the dramatic and durable expansion of leukemia specific T cells in the peripheral blood and marrow and was associated with more than 70% of patients remaining in remission with a mean follow up of 5 years, despite a mean age of 63 among the study patients[7]. Of note, we demonstrated that prior to vaccination, leukemia specific T cells were nearly absent in the peripheral blood and marrow prior to vaccination. We postulated that DC/tumor fusions would create the necessary expansion of tumor specific T cells that could then be further activated and expanded by the presence of checkpoint inhibition. We hypothesized that vaccination and checkpoint inhibition combined therapy would be synergistic in providing effector cells that maintained a state of activation in the context of the immunosuppressive milieu of the tumor microenvironment.

In the present study, we established an immunocompetent murine AML model in which disease burden could be quantified and tracked by BLI. In this aggressive model, we demonstrated that challenge with syngeneic AML cells resulted in rapid engraftment and death within 30 days. Consistent with the prior clinical experience the introduction of checkpoint inhibition via a mix of antibodies targeting PD-1, TIM3, and RGMb, only modestly slowed disease progression and did not significantly impact survival of animals. Of note, vaccination with syngeneic DC/AML cells 24 hours after tumor challenge, at a state of minimal disease markedly slowed disease progression and resulted in long-term survival in a significant subset of animals. The ideal clinical setting for vaccination in cancer is in low tumor burden states, which is more favorable to allow for priming of the immune system and induction of long-term memory. This has been demonstrated in subset analyses from several trials of cancer vaccines in which vaccine effectiveness was notably higher in patients with minimal or no residual disease[19].

Remarkably, the combination of vaccine and checkpoint inhibition was uniquely capable of eradicating disease and producing long-term survival in all of the animals. In addition, animals treated with the combination of vaccination and checkpoint inhibition were protected from leukemia engraftment after re-challenge with an otherwise lethal dose of leukemia cells consistent with generation of a memory response with long-term efficacy. Therapeutic efficacy of vaccine and combined checkpoint blockade was largely reproduced by PD-1 blockade alone with FV while TIM3 blockade alone with FV enhanced initial vaccine response but resulted in only a subset of animals demonstrating resistance to tumor re-challenge.

To further elucidate the immunologic mechanism responsible for these observations, we studied the impact of therapy on leukemia specific T cell immunity in each of the cohorts of animals. Consistent with the underlying hypothesis, the use of checkpoint inhibition did not increase the relative prevalence of leukemia specific T cells above the untreated animals challenged with tumor cells. Of note, while vaccination with DC/AML fusions resulted in the expansion of leukemia specific T cells in the peripheral blood and spleen, these levels were nearly doubled when animals were treated with the combination of vaccination and checkpoint inhibition. This demonstrated an important concept that while checkpoint blockade was not capable of inducing primary leukemia specific immunity as a single modality, further expansion of vaccine educated T cells was observed. Moreover, assessment of antigen specific anti-tumor immunity revealed a significant increase in the frequency of survivin specific T cells as demonstrated by increase in CD8+/survivin pentamer+ T cells following vaccination and checkpoint inhibition compared to controls. Interestingly, no change was observed in the frequency of CMV specific T cells suggesting tumor specific nature of T cell activation and expansion.

The nature of the immune response following vaccination and checkpoint blockade was further interrogated by scRNA-Seq assessment which demonstrated comparatively increased activation of signaling pathways regulating cell viability, proliferation and survival amongst effector and memory T cells, and downregulation in apoptosis regulating genes. The presence of functional memory T cells have been shown to be a critical immune subset predictive of more durable response following immunotherapy[21]. Furthermore, signaling pathway analysis within CD8 and CD4 memory T cell compartments demonstrated significant upregulation of crucial pathways such as CD28 and TCR signaling, as well as mTOR signaling, known to be important in memory T cell differentiation 22 following vaccination compared to untreated controls. Interestingly, this effect was further upregulated following the addition of checkpoint blockade. Analysis of signaling in effector CD8/Nkg7 T cells showed significant upregulation of NF-κB, mTOR, CD28 and ICOS after vaccination consistent with induction of inflammatory phenotype[23-26]. Combination of vaccine and checkpoint blockade further enhanced the activation of these signaling pathways.

In the context of enhanced expansion of tumor reactive lymphocyte and activation of T cell receptor signaling pathways, we subsequently quantified the effect of vaccination in combination with checkpoint blockade on T cell diversity repertoire. Vaccination with DC/AML fusions resulted in enhanced clonal diversity and the oligoclonal expansion of specific TCR sequences consistent with vaccine mediated targeting of tumor associated epitopes. Importantly the addition of checkpoint inhibitors further enhanced this response, promoting clonal diversity consistent with the selective expansion of the vaccine educated clones. This finding supports the hypothesis that sequential expansion of vaccine educated lymphocytes followed by checkpoint blockade would selectively promote vaccine mediated tumor specific immune responses. It has been previously demonstrated that antigen specific activation of T cells is associated with upregulation of PD-1 expression following chemotherapy amongst patients treated for AML[27], potentially offering a selectively timed target for PD-1 blockade. Based on this premise, checkpoint blockade in the context of vaccination may amplify the tumor specific response in preference to nonspecific activation of autoreactive clones. While a similar amplification of vaccine induced autoimmunity is possible, there was no significant evidence of this in the vaccinated patients or the animals treated with the combination. We have now initiated a clinical trial of DC/tumor vaccination in combination with PD-1 blockade in which therapeutic efficacy and toxicity will be assessed.

REFERENCES

1. Ding L, Ley T J, Larson D E, et al. Clonal evolution in relapsed acute myeloid leukaemia revealed by whole-genome sequencing. *Nature.* 2012; 481(7382):506-510. doi:10.1038/nature10738
2. Champlin R. Reduced intensity allogeneic hematopoietic transplantation is an established standard of care for treatment of older patients with acute myeloid leukemia. *Best Pract Res Clin Haematol.* 2013; 26(3):297-300. doi:10.1016/j.beha.2013.10.011
3. Petersen S L. Alloreactivity as therapeutic principle in the treatment of hematologic malignancies. Studies of clinical and immunologic aspects of allogeneic hematopoietic cell transplantation with nonmyeloablative conditioning. *Dan Med Bull.* 2007; 54(2):112-139.
4. Zarour H M. Reversing T-cell Dysfunction and Exhaustion in Cancer. *Clin Cancer Res.* 2016; 22(8):1856-1864. doi:10.1158/1078-0432.CCR-15-1849
5. Luksza M, Riaz N, Makarov V, et al. A neoantigen fitness model predicts tumour response to checkpoint blockade immunotherapy. *Nature.* 2017; 551(7681):517-520. doi:10.1038/nature24473
6. Daver N, Garcia-Manero G, Basu S, et al. Efficacy, Safety, and Biomarkers of Response to Azacitidine and Nivolumab in Relapsed/Refractory Acute Myeloid Leukemia: A Nonrandomized, Open-Label, Phase I I Study. *Cancer Discov.* 2019; 9(3):370-383. doi:10.1158/2159-8290.CD-18-0774
7. Mahoney K M, Rennert P D, Freeman G J. Combination cancer immunotherapy and new immunomodulatory targets. *Nat Rev Drug Discov.* 2015; 14(8):561-584. doi:10.1038/nrd4591
8. Zhou Q, Munger M E, Veenstra R G, et al. Coexpression of Tim-3 and PD-1 identifies a CD8+ T-cell exhaustion phenotype in mice with disseminated acute myelogenous leukemia. *Blood.* 2011; 117(17):4501-4510. doi:10.1182/blood-2010-10-310425
9. Sakuishi K, Apetoh L, Sullivan J M, Blazar B R, Kuchroo V K, Anderson A C. Targeting Tim-3 and PD-1 pathways to reverse T cell exhaustion and restore anti-tumor immunity. *J Exp Med.* 2010; 207(10):2187-2194. doi:10.1084/jem.20100643
10. Kikushige Y, Miyamoto T, Yuda J, et al. A TIM-3/Gal-9 Autocrine Stimulatory Loop Drives Self-Renewal of Human Myeloid Leukemia Stem Cells and Leukemic Progression. *Cell Stem Cell.* 2015; 17(3):341-352. doi:10.1016/j.stem.2015.07.011
11. Severyn C J, Shinde U, Rotwein P. Molecular biology, genetics and biochemistry of the repulsive guidance molecule family. *Biochem J.* 2009; 422(3):393-403. doi:10.1042/BJ20090978
12. Raymond A, Liu B, Liang H, et al. A role for BMP-induced homeobox gene MIXL1 in acute myelogenous leukemia and identification of type I BMP receptor as a potential target for therapy. *Oncotarget.* 2014; 5(24):12675-12693. doi:10.18632/oncotarget.2564
13. Nahas M R, Stroopinsky D, Rosenblatt J, et al. Hypomethylating agent alters the immune microenvironment in acute myeloid leukaemia (AML) and enhances the immunogenicity of a dendritic cell/AML vaccine. *Br J Haematol.* 2019; 185(4):679-690. doi:10.1111/bjh.15818
14. Butler A, Hoffman P, Smibert P, Papalexi E, Satija R. Integrating single-cell transcriptomic data across different conditions, technologies, and species. *Nat Biotechnol.* 2018; 36(5):411-420. doi:10.1038/nbt.4096
15. Brahmer J R, Tykodi S S, Chow L Q M, et al. Safety and activity of anti-PD-L1 antibody in patients with advanced cancer. *N Engl J Med.* 2012; 366(26):2455-2465. doi:10.1056/NEJMoa1200694
16. Stahl M, Goldberg A D. Immune Checkpoint Inhibitors in Acute Myeloid Leukemia: Novel Combinations and Therapeutic Targets. *Curr Oncol Rep.* 2019; 21(4):37. doi:10.1007/s11912-019-0781-7
17. Rosenblatt J, Avivi I, Vasir B, et al. Vaccination with dendritic cell/tumor fusions following autologous stem cell transplant induces immunologic and clinical responses in multiple myeloma patients. *Clin Cancer Res.* 2013; 19(13):3640-3648. doi:10.1158/1078-0432.CCR-13-0282
18. Rosenblatt J, Vasir B, Uhl L, et al. Vaccination with dendritic cell/tumor fusion cells results in cellular and humoral antitumor immune responses in patients with multiple myeloma. *Blood.* 2011; 117(2):393-402. doi:10.1182/blood-2010-04-277137
19. Hale D F, Vreeland T J, Peoples G E. Arming the Immune System Through Vaccination to Prevent Cancer Recurrence. *American Society of Clinical Oncology Educational Book.* 2016; (36):e159-e167. doi:10.1200/EDBK_158946
20. Opzoomer J W, Sosnowska D, Anstee J E, Spicer J F, Arnold J N. Cytotoxic Chemotherapy as an Immune Stimulus: A Molecular Perspective on Turning Up the Immunological Heat on Cancer. *Front Immunol.* 2019; 10. doi:10.3389/fimmu.2019.01654
21. Zuazo M, Arasanz H, Fernández-Hinojal G, et al. Functional systemic CD4 immunity is required for clinical responses to PD-L1/PD-1 blockade therapy. *EMBO Mol Med.* 2019; 11(7):e10293. doi:10.15252/emmm.201910293
22. Araki K, Turner A P, Shaffer V O, et al. mTOR regulates memory CD8 T-cell differentiation. *Nature.* 2009; 460(7251):108-112. doi:10.1038/nature08155
23. Liu T, Zhang L, Joo D, Sun S-C. NF-κB signaling in inflammation. *Signal Transduct Target Ther.* 2017; 2. doi:10.1038/sigtrans.2017.23
24. Peter C, Waldmann H, Cobbold S P. mTOR signalling and metabolic regulation of T cell differentiation. *Curr Opin Immunol.* 2010; 22(5):655-661. doi:10.1016/j.coi.2010.08.010
25. Thompson C B, Lindsten T, Ledbetter J A, et al. CD28 activation pathway regulates the production of multiple T-cell-derived lymphokines/cytokines. *Proc Natl Acad Sci USA.* 1989; 86(4):1333-1337. doi:10.1073/pnas.86.4.1333
26. Dong C, Juedes A E, Temann U A, et al. ICOS co-stimulatory receptor is essential for T-cell activation and function. *Nature.* 2001; 409(6816):97-101. doi:10.1038/35051100
27. Sehgal A, Whiteside T L, Boyiadzis M. Programmed death-1 checkpoint blockade in acute myeloid leukemia. *Expert Opin Biol Ther.* 2015; 15(8):1191-1203. doi:10.1517/14712598.2015.1051028

Example 2: T Cells Educated by DC/AML Fusions in the Context of 4-1BB Costimulation as a Potent Strategy for Adoptive Cellular Therapy Introduction Our group has developed a novel vaccine using patient-derived acute myeloid leukemia (AML) cells and autologous dendritic cells (DCs), capable of presenting a broad array of leukemia antigens. In a phase I/II clinical trial DC/AML vaccination led to an expansion of leukemia-specific T cells. We hypothesized that the fusion vaccine offered a unique platform for ex vivo expansion of functionally potent leukemia specific T cells with broad specificity targeting shared and tumor specific neoantigens. We postulated that incorporating 4-1BB (CD137) mediated co-stimulation would further enhance activation of antigen specific T cells and the development of a crucial memory response as well as promote survival and persistence. Here we describe therapeutic exploration of the use of 4-1BB to augment vaccine-educated T cells for adoptive cellular therapy in an immunocompetent murine model.

Methods

DC/AML fusion vaccine was generated using DCs obtained from C57BL/6J mice and syngeneic C1498 AML cells as previously described. T cells were obtained from splenocytes after magnetic bead isolation and cultured with irradiated DC/AML fusion vaccine in the presence of IL-15 and IL-7. Following co-culture, 4-1BB positive T cells were ligated using agonistic 4-1BB antibody (3H3 clone, BioXCell) and further selected with RatIgG2a magnetic beads (Easy Sep). Subsequently T cells were expanded with anti-CD3/CD28 activation beads (Dynabeads). In vivo, mice underwent retro-orbital inoculation with C1498 and vaccination with irradiated fusion cells the following day. Agonistic mouse anti-4-1BB antibody was injected intraperitoneally on day 4 and day 7. In addition, C1498 cells were transduced with Mcherry/luciferase and a reproducible model of disease progression was established.

Results

DC/fusion stimulated T cells showed increased immune activation as measured by multichannel flow cytometric analysis. Compared to unstimulated T cells, there was 5-fold increase in CD4+CD25+CD69+, and a 10-fold and 7-fold increase in 4-1BB and intracellular IFNγ expression on CD8+ cells respectively. Following agonistic 4-1BB ligation and bead isolation, the proliferation rate was increased in the 4-1BB positive fraction as compared to both 4-1BB negative cells and unstimulated T cells. In addition, the 4-1BB positive fraction demonstrated increased cytotoxicity, as measured by a CTL assay detecting granzyme B with 1:10 tumor to effector cells. A shift from naïve to memory T cell phenotype was also observed. Following D C/fusion stimulation, CD44+CD62L− cells comprised 67% of CD8+ cells versus 20% without stimulation, the latter reflecting the effect of cytokines alone. Following 4-1BB ligation and anti-CD3/CD28 bead expansion, this phenotype was retained with the CD4+ and CD8+ effector memory and central memory compartments comprising the majority of T cells. Such findings are significant as presence of memory T cell populations are a critical component for successful adoptive cell transfer.

The effect of agonistic 4-1BB antibody following vaccination was evaluated in vivo in an aggressive immunocompetent murine AML model. The combination of DC/AML fusion vaccine with 4-1BB antibody was associated with increased long-term survival (>120 days) of 40% versus 20% of mice treated with vaccine alone while all controls required euthanasia by 40 days.

Conclusion

In the current study we have demonstrated the ability of DC/AML fusion vaccine to stimulate T cells ex-vivo as demonstrated by both early-activation (CD25,CD69), upregulation of antigen-specific markers (CD137) and cytokine secretion. Further enhancement of the cellular product using agonistic 4-1BB ligation and isolation simultaneously enriches for antigen-activated cells, as demonstrated by more potent cytotoxicity, as well as promoting memory phenotype and survival. Use of 4-1BB ligation for antigen-specific selection while providing an agonistic co-stimulatory signal is a potentially novel approach for development of non-engineered T cells. Ongoing experiments evaluating the efficacy of 4-1BB selected vaccine educated T cells using bioluminescence monitoring will be reported as well as in vitro use of patient-derived T cells.

Example 3: Potent Synergy Between Combination of Chimeric Antigen Receptor (CAR) Therapy Targeting C D19 in Conjunction with Dendritic Cell (DC)/Tumor Fusion Vaccine in Hematological Malignancies Introduction CAR T cells have demonstrated unique potency for tumor cytoreduction and the potential for durable response in patients with advanced hematological malignancies. However, disease relapse remains a significant concern due to the emergence of antigen negative variants, tolerization of CAR T cell populations and lack of T cell persistence. We have developed a personalized cancer vaccine in which patient derived tumor cells are fused with autologous dendritic cells such that a broad array of tumor antigens is expressed in the context of DC mediated co-stimulation. Vaccination of patients with acute leukemia and multiple myeloma has been associated with the durable expansion of tumor specific lymphocytes in the bone marrow and peripheral blood, targeting of residual disease, and durable remission. We postulated that vaccination with DC/tumor fusions would enhance CAR T cell efficacy through the expansion of T cell clonal populations targeting tumor cells via the native TCR and the vaccine mediated enhancement of T cell activation and persistence. In addition, ex vivo engineered CAR T cells provide a substrate of functionally competent T cells with cytoreductive capacity in the setting of advanced disease. In the present study, we examined the potential synergy between CAR T cells targeting CD19 and syngeneic DC/tumor fusions.

Methods/Results

CAR T cells and DC/tumor fusions were studied in the context of a murine A20 lymphoma model. CD19 CAR T cells were established through retroviral transduction of a CD19 CAR construct expressing CD28 and 41BBL syngeneic DC/A20 fusions were generated as previously described. Vaccine stimulated T cells were generated by coculturing splenocyte derived T cells with syngeneic DC/A20 fusion cells over a period of three days in a 10:1 ratio in the presence of low dose IL2.

While CD19 CAR T cells effectively lysed a subset of A20 cells in a CTL, the addition of vaccine educated T cells increased the percentage of tumor cells undergoing CTL mediated lysis (20% vs 34%). We subsequently examined the interaction of vaccine and CAR T cells ex vivo using the IncuCyte S3 Live-Cell Analysis System which allows for live cell visualization of lysis of A20 cells over time. We studied the impact of combining vaccine educated and CAR T cells as well as an individual T cell population that underwent sequential vaccine mediated stimulation followed by transduction with the CD19 CAR. While vaccine educated and CAR T cells demonstrated potent lysis of A20 cells over time, coculture with either combined vaccine educated and CAR T cells or sequentially vaccine educated and transduced T cells demonstrated the highest levels of cytotoxicity that was maintained over time (1786 and 2338 signal overlap count per image at 23 hours compared to 123 of the control). Enhanced lysis by combined vaccine stimulation and CAR T cells was similarly demonstrated in another tumor cell line, 5TGM1, a multiple myeloma cell line transduced to express CD19. Cytotoxic killing of the 5TGM1-CD19 cells was most pronounced when combining vaccine educated and CAR T cells as compared to CAR T cells alone (33% vs 14%). Consistent with the broad targeting of vaccine educated as compared to the CAR T cell population, wild type 5TGM1 cells were recognized by the DC/tumor fusion stimulated cells in contrast to CAR T cells alone (40% vs. 8%).

We subsequently examined the capacity of vaccine educated T cells in conjunction with CAR T cells to target A20 cells in an immunocompetent murine model. Mice were challenged with 1×10(6) A20 Mcherry-Luc and lymphoma engraftment was demonstrated at Day 7. Animals were then treated with 3×10(6) T cells consisting of CAR T cells, vaccine educated T cells or the combination. Serial bioluminescence imaging demonstrated greatest reduction in tumor burden using combined CAR T and vaccine educated T cells with 4/5 animals without BLI evidence of disease at day 13 after tumor challenge.

Conclusions

In in vitro and immunocompetent murine models, we have demonstrated that combined therapy with T cells stimulated by DC/tumor fusions and CAR T cells exhibited potent lysis of murine lymphoma and myeloma cells as compared to the efficacy of CAR T cells or vaccine educated T cells alone. These findings suggest potent synergy between these modalities that may overcome recognized pathways of resistance including the broadening of the tumor specific response and vaccine mediated activation of CAR T cell populations.

Example 4: Development of Novel Second Generation D C/Tumor Fusion Vaccine in Lymphoma Introduction We have pioneered a personalized cancer vaccine in which patient derived tumor cells are fused with autologous dendritic cells (DCs) such that a broad array of shared and neo-tumor antigens is presented in the context of DC mediated co-stimulation, limiting the risk of antigen escape. In clinical trials of patients with hematologic malignancies, vaccination with DC/tumor fusions induced an expansion of tumor-specific T cells, and resulted in prolonged remissions in a subset of patients. In the current study, we have developed a novel second generation vaccine, whereby a DC/lymphoma fusion vaccine is presented in the context of a unique biomatrix that expresses high levels of the 41BB costimulatory molecule, to further accentuate T cell activation and prevent the establishment of tumor tolerance. In this study, we demonstrate efficacy of DC/lymphoma fusion cell vaccination in a preclinical lymphoma model, and show enhanced potency of the second-generation vaccine.

Methods/Results

We first demonstrated the potency of the DC/tumor fusion vaccine in generating anti-tumor immunity in the A20 lymphoma model. Murine D C/A20 fusions were generated from bone marrow derived mononuclear cells cultured with GM-CSF and IL-4 then fused to syngeneic A20 lymphoma cells. DC/A20 fusion cells effectively induced tumor specific immunity as manifested by potent lysis of A20 T cells in vitro as compared to unstimulated T cells in a standard CTL assay. Consistent with this observation, vaccination with DC/A20 fusions effectively induced lymphoma specific immunity in an immunocompetent murine model. Balb/C mice (30 animals) underwent IV inoculation with 750,000 syngeneic, luciferase and mCherry transduced, A20 cells. 24 hours after tumor cells challenge, 15 mice were treated subcutaneously with $10^5$ DC/A20 fusions. Tumor burden was detected using BLI imaging. 10 days post inoculation, within the untreated cohort all 15/15 mice had detectable tumor whereas within the treated group, 5 mice did not demonstrate any evidence of disease and 5 mice demonstrated minimal disease.

We subsequently demonstrated that patient derived autologous DC/lymphoma fusions stimulated T cell mediated lysis of primary lymphoma cells. DC were generated from patient derived peripheral blood mononuclear cells cultured with GM-CSF and IL-4 and matured with TNFa. Primary lymphoma cells were isolated from resected tumor and fused with DC at a ratio of 10:1. Fusion stimulated T cells potently lysed autologous tumor cells as compared to unstimulated T cells (25.7% as compared to 12.66%) in a standard CTL assay.

To further enhance vaccine potency, we developed a biomatrix substrate expressing the costimulatory molecule 41BB. Using carbodiimide chemistry we covalently bonded RGD peptide and 41BBL protein to an alginate (Alg)-based scaffold. The Alg/RGD/41BBL scaffold can serve as a supporting microenvironment for the co-culture of T cells and fusion vaccine. We cultured syngeneic T cells with DC/A20 fusion vaccine within a scaffold with or without bound 41BBL and examined the T cells cytotoxicity by a CTL assay as described above. Vaccine mediated stimulation of T cells in the context of the Alg/RGD/41BBL scaffold demonstrated higher levels of tumor lysis as compared to the percent T cells cultured within an Alg/RGD scaffold (22.95% and 13.95% respectively).

Conclusion

In the current study we assessed the efficacy of the DC/Lymphoma fusion vaccine to elicit a tumor specific immune response. We succeeded in demonstrating the capacity of DC/Lymphoma fusion vaccine to generate tumor specific T cell cytotoxicity in vitro as well as in vivo in an immunocompetent murine model. Accordingly, we presented patient derived primary tumor results supporting the applicable nature of the DC/Lymphoma vaccine in lymphoma patients. In addition, we developed a second-generation fusion vaccine comprised of the original DC/Tumor vaccine presented to the T cells in an Alg/RGD/41BBL scaffold acting as a nurturing microenvironment for T cell immune specific response against the tumor cells. Our initial results exhibit promising potential and an in vivo experiment with the second-generation fusion vaccine is ongoing.

Example 5: Development of Novel Second Generation D C/Tumor Fusion Vaccine in Lymphoma Tumors evade the immune system through various mechanisms including decreased stimulatory receptors, defective antigen presentation, and T cell tolerance. T cells require co-stimulatory signals for optimal proliferation, differentiation, and survival making co-stimulation necessary to induce productive immune responses. Latest tumor immunotherapy address the disruption of the immune synapse and try to overcome by therapy directed against co-stimulatory and co-inhibitory markers in the tumor microenvironment (as checkpoints) or by cellular therapy (CAR-T).

Relevant schematics and results are provided in FIG. 8 through FIG. 20.

Conclusions

41BBL bound to the alginate scaffold increased immune response to tumor by increased T cell activation. We are expanding the search for the ideal co-stimulatory composition to enable T cell education by the fusion vaccine and proliferation in vivo as well as in vitro (T cell therapy). Anchoring the molecules to the scaffold enables presentation to the cells in a more "nature inspired" way. Therefore the Alginate based scaffold may serve as a platform to test the different co-stimulatory molecules and their effect on the T cell population.

Example 6: Potent Synergy Between Combination of Chimeric Antigen Receptor (CAR) Therapy Targeting C D19 in Conjunction with Dendritic Cell (DC)/Tumor Fusion Vaccine in Hematological Malignancies Combining Vaccine and CAR T Cell Therapy CAR T cells are highly potent but relapse remains due to antigen negative variants, tolerization of the T cell response, and extinguishing of the CAR T population. DC Fusion Vaccine induces expansion of native T cells with broad anti-tumor response targeting neoantigens but limited by effector cell function. DC Fusion Vaccine may enhance CAR T cell potency by broadening the tumor specific response via the native TCR and promote persistence due to physiologic stimulation and re-expansion.

Relevant schematics and results are provided in FIG. 21 through FIG. 29.

Conclusions

CAR-T cells and vaccine educated T cells (sequential) and in combination show increased cytotoxic killing capability. Combination treatment with CAR-T cells and vaccine educated T cells or active vaccination reduce tumor burden and slow progression in A20 lymphoma model. Moreover, vaccine educated T cells+CD19 CAR T cells more effectively target A20 murine lymphoma cells as compared to CAR T cells and naïve T cells in vitro as measured by reduced bioluminescence labeling of tumor cell populations.

Vaccine administration seem to increase CAR-T cells in treated mice peripheral blood.

Example 7: Designing the Optimal Vaccine and Adoptive T Cell Therapy

Studies were undertaken for Second Generation Cellular Cancer Vaccines: Creating an Artificial Lymph Node, for using Vaccine Educated T cells as Adoptive Immunotherapy, for Vaccination in Conjunction with Checkpoint Inhibition, for Combining Costimulatory Chimeric Receptor to Address Tolerance and Prevent Antigen Escape, and for Vaccination in the Conjunction with CAR T cells. Relevant schematics and results are provided in FIG. 30 through FIG. 34.

Figure 35:
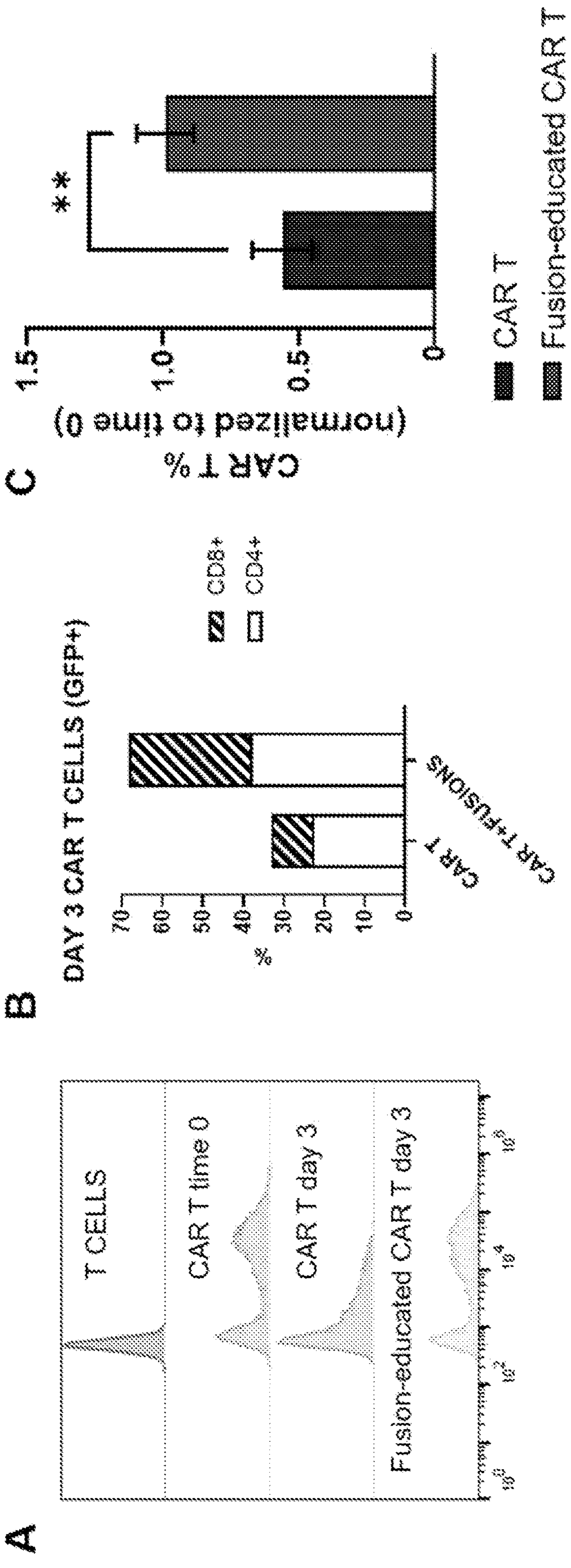
FIG. 35A-35C show that in vitro co-culture of CAR-T cells and DC/A20 vaccine improves CAR-T expansion in vitro.
Figure 36:
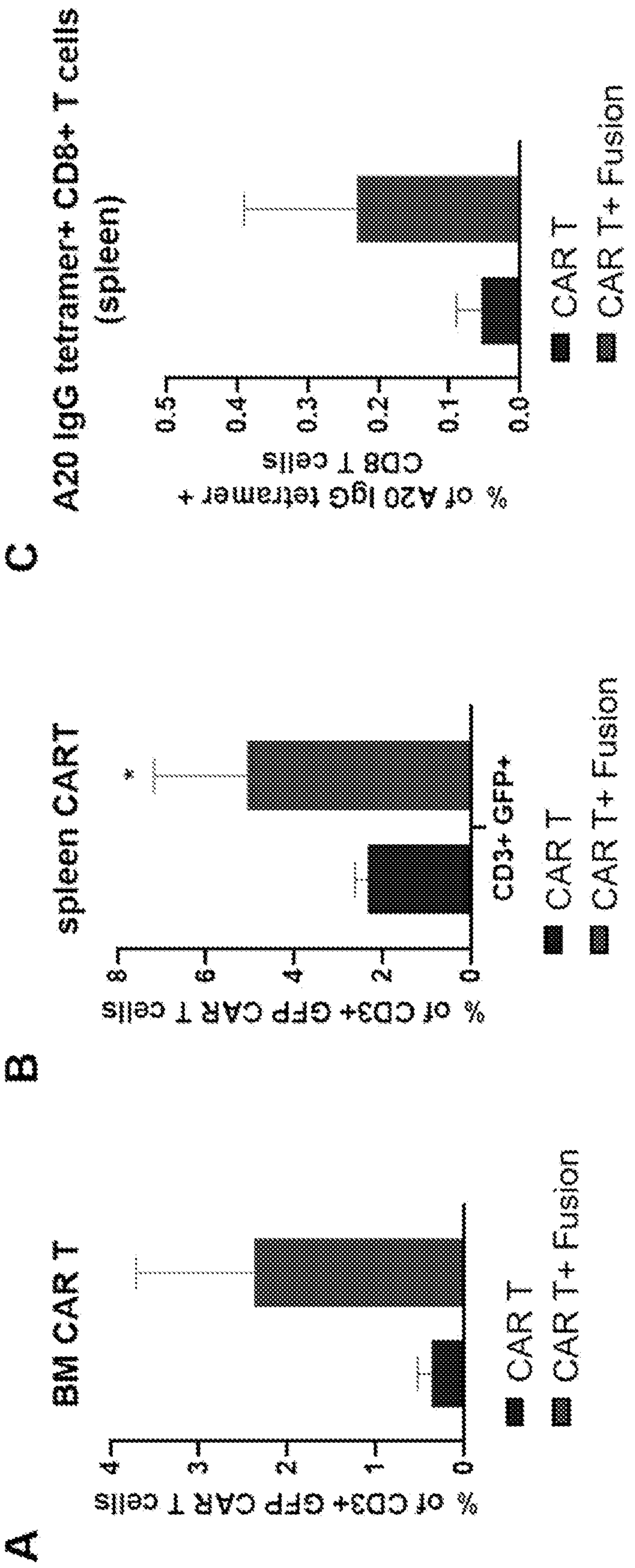
FIG. 36A-36C show that in vivo DC/tumor fusion vaccination increases persistence of CAR T cells in vivo. B-cell lymphoma was induced in BALB/c mice by tail vein injection of A20 cells. The mice were lymphodepleted and treated with m19BBz-GFP CAR-T. The mice were then subcutaneously injected with the DC/A20 fusion vaccine or with PBS (CAR T, control group).
Figure 37:
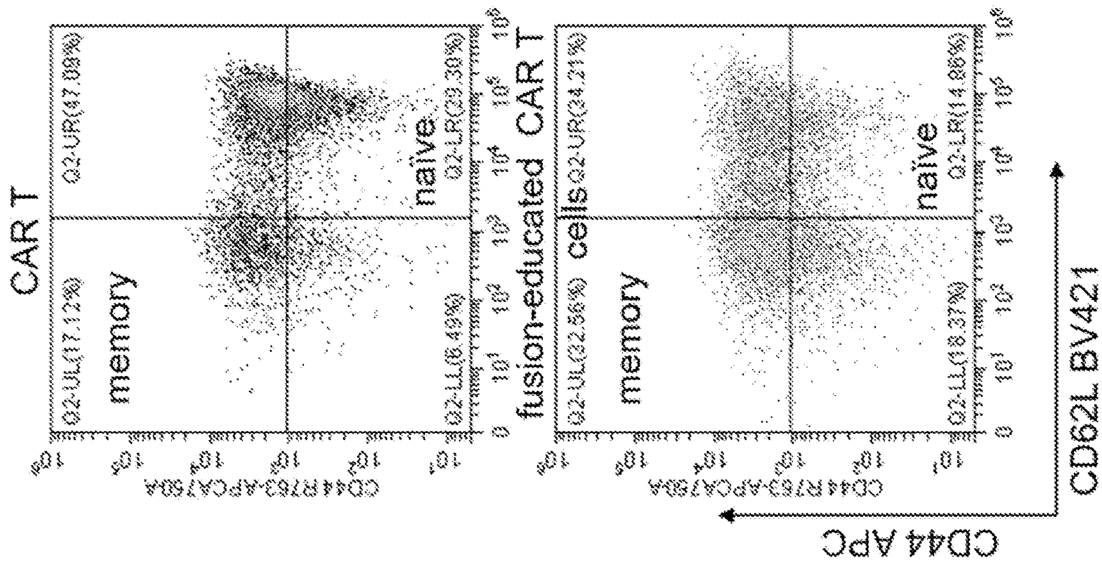
FIG. 37 shows that in vitro co-culture of CAR-T cells and DC/A20 vaccine induces a memory-like CAR-T phenotype. T cells transduced with the m19BBz-GFP CAR were co-cultured in the presence (fusions-educated CAR T cells) or the absence (CAR T cells) of the DC/A20 vaccine for 3 days. Cells were stained with the indicated antibodies and flow cytometry was performed to assess the % of memory (CD62L−CD44+) and naïve (CD62L+CD44−) T cells. In vitro co-culture of CAR-T cells and DC/A20 vaccine induced a memory-like CAR-T phenotype and strongly improved CAR-T persistence.

Moreover, further analyses were performed in order to further confirm that vaccine can improve CAR-T expansion in vitro, increase the persistence of CAR-T cells in vivo, and induce a memory-like CAR-T phenotype as demonstrated in, for example, representative FIG. 35 through FIG. 37.

INCORPORATION BY REFERENCE

All publications, patents, and patent applications mentioned herein are hereby incorporated by reference in their entirety as if each individual publication, patent or patent application was specifically and individually indicated to be incorporated by reference. In case of conflict, the present application, including any definitions herein, will control.

Also incorporated by reference in their entirety are any polynucleotide and polypeptide sequences which reference an accession number correlating to an entry in a public database, such as those maintained by The Institute for Genomic Research (TIGR) on the world wide web and/or the National Center for Biotechnology Information (NCBI) on the world wide web.

EQUIVALENTS

Those skilled in the art will recognize, or be able to ascertain using no more than routine experimentation, many equivalents to the specific embodiments of the present invention described herein. Such equivalents are intended to be encompassed by the following claims.

What is claimed is:

1. A method of treating a lymphoma in a subject, the method comprising administering to the subject a T-cell composition, wherein the T-cell composition comprises Chimeric Antigen Receptor T (CAR-T) cells and educated T cells, wherein the educated T cells are obtained by co-culturing T cells with a fusion cell at a ratio of 10:1 T cells to fusion cells for 3 days in the presence of interleukin-2 (IL-2), wherein the fusion cell comprises a fusion of a dendritic cell and a lymphoma cell, and wherein the cells target an antigen expressed by the lymphoma.

2. The method of claim 1, wherein the method further comprises administering an agonistic 4-1BB antibody or an antigen-binding fragment thereof.

3. The method of claim 1, wherein the educated T cells are obtained by co-culturing T cells with a biomatrix in conjunction with the fusion cell, wherein the biomatrix comprises alginate, RGD peptide, and 4-1BBL.

4. The method of claim 1, wherein the CAR-T cells are directed against CD-19 or BCMA.

5. The method of claim 1, wherein the lymphoma comprises multiple myeloma.

6. The method of claim 1, wherein the CAR-T cells comprise educated CAR-T cells.

7. The method of claim 6, wherein the educated CAR-T cells are obtained by transducing educated T cells with a CAR.

8. The method of claim 1, wherein the T-cell composition is obtained by combining a population of CAR-T cells with a separate population of educated T cells.

9. The method of claim 1, wherein the dendritic cell is autologous to the subject.

10. The method of claim 1, wherein the lymphoma tumor cell is obtained or derived from the subject.

11. The method of claim 1, wherein the fusion cell vaccine is gamma irradiated.

* * * * *